(12) United States Patent
Yamamoto

(10) Patent No.: US 10,328,109 B2
(45) Date of Patent: Jun. 25, 2019

(54) TARGETED ADENOVIRUSES AND METHODS OF MAKING, ISOLATING, AND USING

(71) Applicant: REGENTS OF THE UNIVERSITY OF MINNESOTA, Minneapolis, MN (US)

(72) Inventor: Masato Yamamoto, Golden Valley, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 15/306,217

(22) PCT Filed: Apr. 24, 2015

(86) PCT No.: PCT/US2015/027554
§ 371 (c)(1),
(2) Date: Oct. 24, 2016

(87) PCT Pub. No.: WO2015/164769
PCT Pub. Date: Oct. 29, 2015

(65) Prior Publication Data
US 2017/0119830 A1    May 4, 2017

Related U.S. Application Data

(60) Provisional application No. 61/984,602, filed on Apr. 25, 2014.

(51) Int. Cl.
| | | |
|---|---|---|
| *A61K 35/761* | (2015.01) | |
| *C12N 7/00* | (2006.01) | |
| *G01N 33/574* | (2006.01) | |
| *C07K 14/005* | (2006.01) | |
| *C12N 15/86* | (2006.01) | |

(52) U.S. Cl.
CPC .......... *A61K 35/761* (2013.01); *C07K 14/005* (2013.01); *C12N 7/00* (2013.01); *C12N 15/86* (2013.01); *G01N 33/57492* (2013.01); *C12N 2710/10321* (2013.01); *C12N 2710/10322* (2013.01); *C12N 2710/10332* (2013.01); *C12N 2710/10345* (2013.01); *C12N 2710/10351* (2013.01)

(58) Field of Classification Search
CPC ........ A61K 35/761; C12N 2710/10321; C12N 2710/10332; C12N 7/00; C12N 15/8616; G01N 33/57492

See application file for complete search history.

(56) References Cited

U.S. PATENT DOCUMENTS

| | | | |
|---|---|---|---|
| 2004/0038205 A1 | 2/2004 | Van Raaij | |
| 2012/0264192 A1* | 10/2012 | Yamamoto | C12N 15/1034 435/235.1 |
| 2017/0119830 A1 | 5/2017 | Yamamoto | |

FOREIGN PATENT DOCUMENTS

| | | |
|---|---|---|
| WO | WO 2009/037329 A2 | 3/2009 |
| WO | WO 2015/164769 A1 | 10/2015 |

OTHER PUBLICATIONS

Nishimoto et al 2009, Gene Therapy 16:669-680.*
Miura et al 2007, Gene-therapy 14{1448-1460.*
Nishimoto et al 2012, PLOS One 7:1-9.*
International Patent Application No. PCT/US2015/027554, filed Apr. 24, 2015; International Preliminary Report on Patentability dated Nov. 3, 2016; 10 pgs.
International Patent Application No. PCT/US2015/027554, filed Apr. 24, 2015; International Search Report and Written Opinion dated Oct. 14, 2015; 17 pgs.
Berk, "Virology," vol. 2, Edn. 5. (eds. D. Knipe & P. Howley) (Lipponcott Williams & Wilkins, Philadelphia; 2007).): 2357-2394.
Dhar, "Pre-existing immunity and passive immunity to adenovirus 5 prevents toxicity caused by an oncolytic adenovirus vector in the Syrian hamster model," 2009 *Mol Ther.*, 17:1724-1732.
Gou, "Establishment of clonal colony-forming assay for propagation of pancreatic cancer cells with stem cell properties," 2007 *Pancreas*, 34:429-435.
Miura, "Direct selection of targeted adenovirus vectors by random peptide display on the fiber knob" 2007 *Gene-therapy*, 14:1448-1460.
Miura, "Infectivity-selective Oncolytic Adenovirus Developed by High-throughput Screening of Adenovirus-formatted Library," 2013, *Mol Ther*, 21(1):139-148.
Miura, "431. Efficient Systemic Treatment with Fiber-Redesigned Oncolytic Adenovirus in Pancreatic Cancer In Vivo Model" May 2015 *Mol. Ther.*, 23(S1):S170.
Miura, "Systemic treatment of fiber-redesigned oncolytic adenovirus eliminates tumors in Vivo" Abstract. May 2014 Molecular Therapy 22 (Supplement 1, #176); S67.
Miura, "Abstract 724: Systemic injection of fiber-redesigned oncolytic adenorvirus eliminates tumors in vivo" AACR Annual Meeting 2014; Apr. 5-9, 2014; San Diego, CA.
Nishimoto, "Oncolytic virus therapy for pancreatic cancer using the adenovirus library displaying random peptides on the fiber knob" 2009 *Gene Therapy*, 16(5):669-680.
Nishimoto, "Development of Peritoneal Tumor-Targeting Vector by In Vivo Screening with a Random Peptide-Displaying Adenovirus Library" 2012 *PLOS One* 7:1-9.
Palmer, "Improved system for helper-dependent adenoviral vector production," 2003 *Mol Ther.*, 8:846-852.

(Continued)

*Primary Examiner* — Robert M Kelly
(74) *Attorney, Agent, or Firm* — Mueting, Raasch & Gebhardt, PA

(57) ABSTRACT

Described herein is an adenovirus comprising an AB-loop comprising a targeting motif and methods of making and using the adenovirus. The targeting motif of the adenovirus can selectively bind to a tumor cell. The targeting motif of the adenovirus can selectively bind to cell markers and/or cell surface antigens including, for example, CD 133.

3 Claims, 49 Drawing Sheets

Specification includes a Sequence Listing.

(56) References Cited

OTHER PUBLICATIONS

Rao, "Establishment of a human colorectal cancer cell line P6C with stem cell properties and resistance to chemotherapeutic drugs," 2013, *Acta Pharmacol Sin*, 34:93-804.

Ricci-Vitiani, "Identification and expansion of human colon-cancer-initiating cells," Jan. 2007 *Nature*, 445:111-115.

Sato, "309. The isolation of CD133-targeted adenovirus by screening with a fiber-modified adenovirus library" Abstract. May 2014 *Molecular Therapy* 22 (Suppl 1); S119.

Tsuruta, "A Fiber-Modified Mesothelin Promoter-Based Conditionally Replicating Adenovirus for Treatment of Ovarian Cancer," 2008 *Clin Cancer Res*, 14:3582-3588.

Von Seggern, "Adenovirus Vector Pseudotyping in Fiber-Expressing Cell Lines: Improved Transduction of Epstein-Barr Virus-Transformed B Cell," 2000 *J Virol.*, 74(1):354-362.

Yamamoto, "Development of a novel efficient method to construct an adenovirus library displaying random peptides on the fiber knob" Mar. 2014 *Molecular Pharmaceutics*, 11(3):1069-1074.

\* cited by examiner

*Figure 2b*

Wild-type HI-loop sequence:
5'-GAC ACA ACT CCA AGT GCA-3' (SEQ ID NO:51)
    D   T   T   P   S   A (SEQ ID NO:52)

Background shuttle plasmid of HI-loop fiber-modified library:
             Csp45I      SpeI
5'-GAC ACA ACT TTC GAA A ACT AGT CCA AGT GCA-3' (SEQ ID NO:53)
    D   T   T   F   E   N   *   S   K   C (SEQ ID NO:54)

HI-loop random mutation fiber-modified library:
           Csp45I                                         SpeI
5'-GAC ACA ACT TTC GAA NNK NNK NNK NNK NNK NNK NNK NNK ACT AGT CCA AGT GCA-3' (SEQ ID NO:55)
    D   T   T   F   E   N   X   X   X   X   X   X   X   T   S   P   S   A (SEQ ID NO:56)
                                      Random library
                                     NNK (N=A,G,C K=G,T)

Random 7 amino acids library in HI-loop pBHIΔCAR-lib

*Figure 2c*

CAR-binding domains

Wild-type AB-loop sequence

5'- ACA CCA GCT CCA TCT CCT AAC TGT AGA CTA AAT GCA GAG GAA -3' (SEQ ID NO:57)
    T   P   A   P   S   P   N   C   R   L   N   A   E   K (SEQ ID NO:58)

Random mutations library

5'- ACA CCA GCT CCA TCT CCT AAC NNK NNK NNK NNK NNK NNK NNK -3' (SEQ ID NO:59)
    T   P   A   P   S   P   N   X   X   X   X   X   X   X (SEQ ID NO:60)
                                    Random library
                                 NNK (N=A,G,C,T K=G,T)

Random 7 amino acids library in AB-loop pMLAB-lib

▶ loxP site in ΔE3    |||| mutation in AB-loop (CAR-binding ablated)

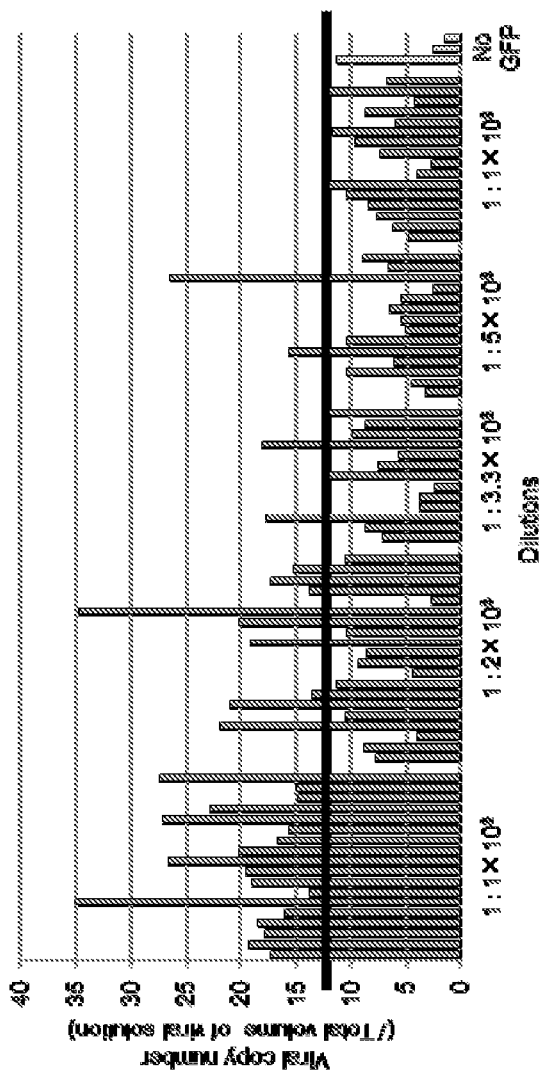
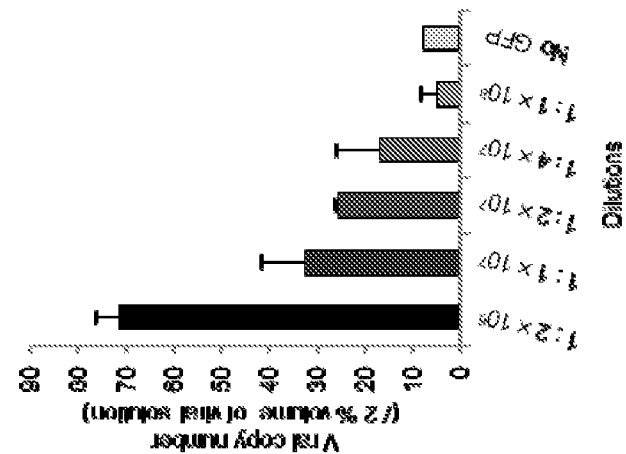
Figure 8a
Figure 8b

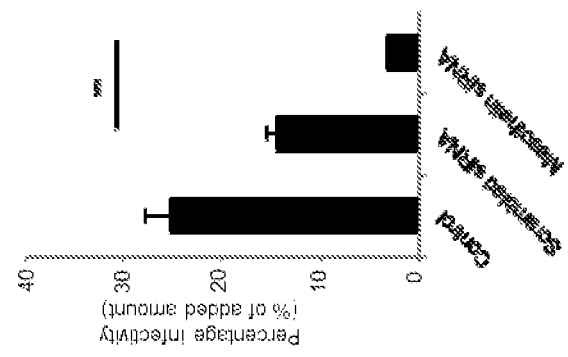
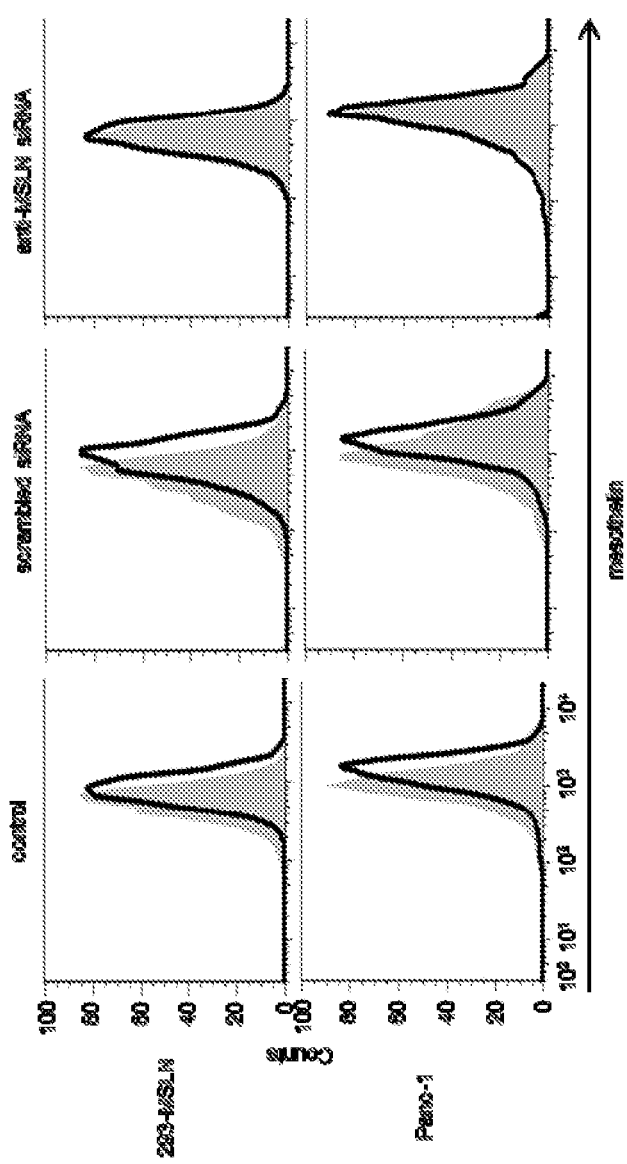
Figure 11a
Figure 11b

*Figure 23*
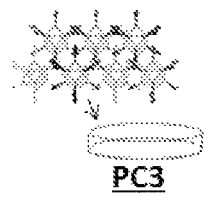
*Figure 24*
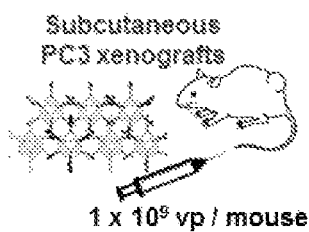
Sacrifice at 5, 10 days
after i.v.
DNA extraction from
tumor
Make single clone
and sequencing

*Figure 43*

(10vp/cells, Day 18)

*Figure 45*

| | 1vp/cells, 5hr. | | | | | | |
|---|---|---|---|---|---|---|---|
| | | Injected cell number | | | | | |
| | | Day 7 | | | Day 14 | | |
| | Cell name | $1 \times 10^5$ cells | $1 \times 10^4$ cells | | $1 \times 10^5$ cells | $1 \times 10^4$ cells | |
| CD133(+) | LoVo (-) | 75% (3/4) | 50% (2/4) | | 100% (4/4) | 75% (3/4) | |
| CD133(+) | LoVo +virus | 0% (0/4) | 0% (0/4) | | 0% (0/4) | 0% (0/4) | |
| CD133(-) | LS (-) | 75% (3/4) | 25% (1/4) | | 100% (4/4) | 75% (3/4) | |
| CD133(-) | LS +virus | 25% (1/4) | 25% (1/4) | | 75% (3/4) | 50% (2/4) | |

SEQUENCE LISTING

<160> NUMBER OF SEQ ID NOS: 114

<210> SEQ ID NO 1
<211> LENGTH: 93
<212> TYPE: DNA
<213> ORGANISM: artificial
<220> FEATURE:
<223> OTHER INFORMATION: synthetic degenerate oligonucleotide
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 1
aacggtacac aggaaacagg agacacaact ttcgaannkn nknnknnknn knnknnkact    60
agtccaagtg catactctat gtcattttca tgg                                93

<210> SEQ ID NO 2
<211> LENGTH: 24
<212> TYPE: DNA
<213> ORGANISM: artificial
<220> FEATURE:
<223> OTHER INFORMATION: synthetic oligonucleotide primer

<400> SEQUENCE: 2
gaaacaggag acacaacttt cgaa                                          24

<210> SEQ ID NO 3
<211> LENGTH: 24
<212> TYPE: DNA
<213> ORGANISM: artificial
<220> FEATURE:
<223> OTHER INFORMATION: synthetic oligonucleotide primer

<400> SEQUENCE: 3
catagagtat gcacttggac tagt                                          24

<210> SEQ ID NO 4
<211> LENGTH: 99
<212> TYPE: DNA
<213> ORGANISM: artificial
<220> FEATURE:
<223> OTHER INFORMATION: synthetic degenerate oligonucleotide
<220> FEATURE:
<221> NAME/KEY: misc_feature
<222> LOCATION: (40)..(41)
<223> OTHER INFORMATION: n is a, c, g, or t

```
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 4
aagctaactt tgtggaccac accagctcca tctcctaacn nknnknnknn knnknnknnk      60
gatgctaaac tcactttggt cttaacaaaa tgtggcagt                            99

<210> SEQ ID NO 5
<211> LENGTH: 20
<212> TYPE: DNA
<213> ORGANISM: artificial
<220> FEATURE:
<223> OTHER INFORMATION: synthetic oligonucleotide primer

<400> SEQUENCE: 5
aagctaactt tgtggaccac                                                 20

<210> SEQ ID NO 6
<211> LENGTH: 20
<212> TYPE: DNA
<213> ORGANISM: artificial
<220> FEATURE:
<223> OTHER INFORMATION: synthetic oligonucleotide primer

<400> SEQUENCE: 6
actgccacat tttgttaaga                                                 20

<210> SEQ ID NO 7
<211> LENGTH: 24
<212> TYPE: DNA
<213> ORGANISM: artificial
<220> FEATURE:
<223> OTHER INFORMATION: synthetic oligonucleotide primer

<400> SEQUENCE: 7
aattgctagc cctgcaaaca tcag                                            24

<210> SEQ ID NO 8
<211> LENGTH: 21
<212> TYPE: DNA
<213> ORGANISM: artificial
<220> FEATURE:
<223> OTHER INFORMATION: synthetic oligonucleotide primer

<400> SEQUENCE: 8
ggtccacaaa gttagcttat c                                               21
```

-continued

```
<210> SEQ ID NO 9
<211> LENGTH: 21
<212> TYPE: DNA
<213> ORGANISM: artificial
<220> FEATURE:
<223> OTHER INFORMATION: synthetic oligonucleotide primer

<400> SEQUENCE: 9
ttaacaaaat gtggcagtca a                                              21

<210> SEQ ID NO 10
<211> LENGTH: 28
<212> TYPE: DNA
<213> ORGANISM: artificial
<220> FEATURE:
<223> OTHER INFORMATION: synthetic oligonucleotide primer

<400> SEQUENCE: 10
aattcaattg aaaaataaac acgttgaa                                       28

<210> SEQ ID NO 11
<211> LENGTH: 21
<212> TYPE: DNA
<213> ORGANISM: artificial
<220> FEATURE:
<223> OTHER INFORMATION: nucleotide sequence of AB-loop fiber-modified
      adenovirus clone

<400> SEQUENCE: 11
gttactatta atcggtctgc g                                              21

<210> SEQ ID NO 12
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 12

Val Thr Ile Asn Arg Ser Ala
1               5

<210> SEQ ID NO 13
<211> LENGTH: 21
<212> TYPE: DNA
<213> ORGANISM: artificial
<220> FEATURE:
<223> OTHER INFORMATION: nucleotide sequence of AB-loop fiber-modified
      adenovirus clone

<400> SEQUENCE: 13
actcatcttt ctatttatgc t                                              21

<210> SEQ ID NO 14
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 14

Thr His Leu Ser Ile Tyr Ala
1               5
```

```
<210> SEQ ID NO 15
<211> LENGTH: 20
<212> TYPE: DNA
<213> ORGANISM: artificial
<220> FEATURE:
<223> OTHER INFORMATION: synthetic oligonucleotide primer

<400> SEQUENCE: 15
tgaccctgaa gttcatctgc                                               20

<210> SEQ ID NO 16
<211> LENGTH: 20
<212> TYPE: DNA
<213> ORGANISM: artificial
<220> FEATURE:
<223> OTHER INFORMATION: synthetic oligonucleotide primer

<400> SEQUENCE: 16
gaagtcgtgc tgcttcatgt                                               20

<210> SEQ ID NO 17
<211> LENGTH: 24
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: conjugated to a 6-carboxyfluorescein (6FAM)
      fluorophore
<220> FEATURE:
<221> NAME/KEY: misc_feature
<222> LOCATION: (24)..(24)
<223> OTHER INFORMATION: conjugated to a carboxytetramethylrhodamine
      (TAMRA) fluorophore

<400> SEQUENCE: 17
accctcgtga ccaccctgac ctac                                          24

<210> SEQ ID NO 18
<211> LENGTH: 18
<212> TYPE: DNA
<213> ORGANISM: artificial
<220> FEATURE:
<223> OTHER INFORMATION: synthetic oligonucleotide primer

<400> SEQUENCE: 18
ggagtgcgcc gagacaac                                                 18

<210> SEQ ID NO 19
<211> LENGTH: 19
<212> TYPE: DNA
<213> ORGANISM: artificial
<220> FEATURE:
<223> OTHER INFORMATION: synthetic oligonucleotide primer

<400> SEQUENCE: 19
actacgtccg gcgttccat                                                19

<210> SEQ ID NO 20
<211> LENGTH: 20
<212> TYPE: DNA
<213> ORGANISM: artificial
<220> FEATURE:
<223> OTHER INFORMATION: synthetic oligonucleotide primer

<400> SEQUENCE: 20
```
aagctaactt tgtggaccac                                              20

<210> SEQ ID NO 21
<211> LENGTH: 20
<212> TYPE: DNA
<213> ORGANISM: artificial
<220> FEATURE:
<223> OTHER INFORMATION: synthetic oligonucleotide primer

<400> SEQUENCE: 21
actgccacat tttgttaaga                                              20

<210> SEQ ID NO 22
<211> LENGTH: 24
<212> TYPE: DNA
<213> ORGANISM: artificial
<220> FEATURE:
<223> OTHER INFORMATION: synthetic oligonucleotide primer

<400> SEQUENCE: 22
gaaacaggag acacaacttt cgaa                                         24

<210> SEQ ID NO 23
<211> LENGTH: 24
<212> TYPE: DNA
<213> ORGANISM: artificial
<220> FEATURE:
<223> OTHER INFORMATION: synthetic oligonucleotide primer

<400> SEQUENCE: 23
actagtccaa gtgcatactc tatg                                         24

<210> SEQ ID NO 24
<211> LENGTH: 16
<212> TYPE: DNA
<213> ORGANISM: artificial
<220> FEATURE:
<223> OTHER INFORMATION: synthetic oligonucleotide primer

<400> SEQUENCE: 24
gtaaaacgac ggccag                                                  16

<210> SEQ ID NO 25
<211> LENGTH: 17
<212> TYPE: DNA
<213> ORGANISM: artificial
<220> FEATURE:
<223> OTHER INFORMATION: synthetic oligonucleotide primer

<400> SEQUENCE: 25
caggaaacag ctatgac                                                 17

<210> SEQ ID NO 26
<211> LENGTH: 4
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 26

Ala Ala Trp Val
1

<210> SEQ ID NO 27
<211> LENGTH: 7

```
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 27

Ala Met Tyr Ser Thr Leu Tyr
1               5

<210> SEQ ID NO 28
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (6)..(6)
<223> OTHER INFORMATION: Xaa can be any naturally occurring amino acid

<400> SEQUENCE: 28

Asp Ala Arg Val Asp Xaa Asp
1               5

<210> SEQ ID NO 29
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 29

Phe Leu Ala Phe Cys Phe Ala
1               5

<210> SEQ ID NO 30
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 30

Ile His Ser Ala Leu Arg Ala
1               5

<210> SEQ ID NO 31
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Ile Arg Val Trp Lys Xaa Ile
1               5

<210> SEQ ID NO 32
<211> LENGTH: 7
<212> TYPE: PRT
```

```
<213> ORGANISM: artificial
<220> FEATURE:
<223> OTHER INFORMATION: amino acid sequence of AB-loop fiber-modified
      adenovirus clone

<400> SEQUENCE: 32

Ile Tyr Tyr Thr Ile Ser Thr
1               5

<210> SEQ ID NO 33
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 33

Asn Arg Arg Thr Ile Leu Met
1               5

<210> SEQ ID NO 34
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 34

Pro Gly Ala Gly Trp Arg Pro
1               5

<210> SEQ ID NO 35
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 35

Arg Asn Asn Asp Asp Thr Leu
1               5

<210> SEQ ID NO 36
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 36

Arg Val Ser Arg Asn Arg Leu
1               5

<210> SEQ ID NO 37
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 37

Ser Glu Arg Gly Asp Trp Ala
1               5
```

```
<210> SEQ ID NO 38
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 38

Val Glu Val Gly Gly Gly Trp
1               5

<210> SEQ ID NO 39
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 39

Trp Gly Ala Val Phe Gly Gly
1               5

<210> SEQ ID NO 40
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 40

Trp His His Cys Pro Tyr Ser
1               5

<210> SEQ ID NO 41
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 41

Cys Ser Leu Asn Gly Gly Gly
1               5

<210> SEQ ID NO 42
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 42

Glu Gly Arg Arg Val Gly Gly
1               5

<210> SEQ ID NO 43
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
```

```
<400> SEQUENCE: 43

Glu Thr Ser Ser Leu Leu Phe
1               5

<210> SEQ ID NO 44
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 44

Gly Gly Arg Glu Lys Lys Asp
1               5

<210> SEQ ID NO 45
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 45

Asn Lys Ala His Phe Gly Asn
1               5

<210> SEQ ID NO 46
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 46

Ser Ser Ile Leu Trp Ile Gly
1               5

<210> SEQ ID NO 47
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 47

Thr Gly Ala Cys Ser Trp Ser
1               5

<210> SEQ ID NO 48
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 48

Val Gly Ala Trp Thr Gly Arg
1               5

<210> SEQ ID NO 49
<211> LENGTH: 7
```

```
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 49

Val Tyr Pro Thr His Gly Lys
1               5

<210> SEQ ID NO 50
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 50

Val Thr Ile Asp Arg Ser Ala
1               5

<210> SEQ ID NO 51
<211> LENGTH: 18
<212> TYPE: DNA
<213> ORGANISM: artificial
<220> FEATURE:
<223> OTHER INFORMATION: nucleotide sequence of wild type HI-loop

<400> SEQUENCE: 51
gacacaactc caagtgca                                                    18

<210> SEQ ID NO 52
<211> LENGTH: 6
<212> TYPE: PRT
<213> ORGANISM: artificial
<220> FEATURE:
<223> OTHER INFORMATION: amino acid sequence of wild type HI-loop

<400> SEQUENCE: 52

Asp Thr Thr Pro Ser Ala
1               5

<210> SEQ ID NO 53
<211> LENGTH: 31
<212> TYPE: DNA
<213> ORGANISM: artificial
<220> FEATURE:
<223> OTHER INFORMATION: nucleotide sequence from background shuttle
      plasmid of HI-loop fiber-modified library

<400> SEQUENCE: 53
gacacaactt tcgaaaacta gtccaagtgc a                                     31

<210> SEQ ID NO 54
<211> LENGTH: 10
<212> TYPE: PRT
<213> ORGANISM: artificial
<220> FEATURE:
<223> OTHER INFORMATION: amino acid sequence from background shuttle
      plasmid of HI-loop fiber-modified library
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Asp Thr Thr Phe Glu Asn Xaa Ser Lys Cys
```

<210> SEQ ID NO 55
<211> LENGTH: 54
<212> TYPE: DNA
<213> ORGANISM: artificial
<220> FEATURE:
<223> OTHER INFORMATION: nucleotide sequence from HI-loop random
      mutation fiber-modified library
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 55
gacacaactt tcgaannknn knnknnknnk nnknnknnka ctagtccaag tgca      54

<210> SEQ ID NO 56
<211> LENGTH: 18
<212> TYPE: PRT
<213> ORGANISM: artificial
<220> FEATURE:
<223> OTHER INFORMATION: amino acid sequence from HI-loop random
      mutation fiber-modified library
<220> FEATURE:
<221> NAME/KEY: misc_feature
<222> LOCATION: (7)..(13)
<223> OTHER INFORMATION: Xaa can be any naturally occurring amino acid

<400> SEQUENCE: 56

Asp Thr Thr Phe Glu Asn Xaa Xaa Xaa Xaa Xaa Xaa Xaa Thr Ser Pro
1               5                   10                  15

Ser Ala

<210> SEQ ID NO 57
<211> LENGTH: 42
<212> TYPE: DNA
<213> ORGANISM: artificial
<220> FEATURE:
<223> OTHER INFORMATION: nucleotide sequence of wild type AB-loop

<400> SEQUENCE: 57
acaccagctc catctcctaa ctgtagacta aatgcagagg aa      42

```
<210> SEQ ID NO 58
<211> LENGTH: 14
<212> TYPE: PRT
<213> ORGANISM: artificial
<220> FEATURE:
<223> OTHER INFORMATION: amino acid sequence of wild type AB-loop

<400> SEQUENCE: 58

Thr Pro Ala Pro Ser Pro Asn Cys Arg Leu Asn Ala Glu Lys
1               5                   10

<210> SEQ ID NO 59
<211> LENGTH: 42
<212> TYPE: DNA
<213> ORGANISM: artificial
<220> FEATURE:
<223> OTHER INFORMATION: nucleotide sequence from AB-loop random
      mutation fiber-modified library
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 59
acaccagctc catctcctaa cnnknnknnk nnknnknnkn nk                     42

<210> SEQ ID NO 60
<211> LENGTH: 14
<212> TYPE: PRT
<213> ORGANISM: artificial
<220> FEATURE:
<223> OTHER INFORMATION: amino acid sequence from AB-loop random
      mutation fiber-modified library
<220> FEATURE:
<221> NAME/KEY: misc_feature
<222> LOCATION: (8)..(14)
<223> OTHER INFORMATION: Xaa can be any naturally occurring amino acid

<400> SEQUENCE: 60

Thr Pro Ala Pro Ser Pro Asn Xaa Xaa Xaa Xaa Xaa Xaa Xaa
1               5                   10

<210> SEQ ID NO 61
<211> LENGTH: 7
<212> TYPE: PRT
<213> ORGANISM: artificial
<220> FEATURE:
<223> OTHER INFORMATION: amino acid sequence of AB-loop fiber-modified
``` adenovirus clone

<400> SEQUENCE: 61

Ala Leu Ser Ser Thr Leu Asp
1               5

<210> SEQ ID NO 62
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (3)..(3)
<223> OTHER INFORMATION: Xaa can be any naturally occurring amino acid

<400> SEQUENCE: 62

Asn Lys Xaa Cys Asn Lys Arg
1               5

<210> SEQ ID NO 63
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 63

Phe Val Met Phe Val Asn Pro
1               5

<210> SEQ ID NO 64
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 64

Ala Cys Ala His Gly Asp Gly
1               5

<210> SEQ ID NO 65
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 65

Thr Thr Thr His Gln Thr Thr
1               5

<210> SEQ ID NO 66
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 66

Ile Gln Leu Gln Gly Cys Asn

```
<210> SEQ ID NO 67
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 67

Ile Arg Asn His Met Lys Asp
1               5

<210> SEQ ID NO 68
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 68

Ile Gln Leu Gln Gly Arg Asn
1               5

<210> SEQ ID NO 69
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 69

Thr Lys Leu Gln Ser Gly Glu
1               5

<210> SEQ ID NO 70
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 70

Val Gln Ala Gly Thr Gln Pro
1               5

<210> SEQ ID NO 71
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 71

Asn Asp Ser Lys Thr Trp Ser
1               5

<210> SEQ ID NO 72
<211> LENGTH: 6
<212> TYPE: PRT
<213> ORGANISM: artificial
<220> FEATURE:
<223> OTHER INFORMATION: amino acid sequence of AB-loop fiber-modified
``` adenovirus clone

<400> SEQUENCE: 72

Pro Gly Trp Tyr Ser Tyr
1               5

<210> SEQ ID NO 73
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 73

Gly Pro Cys Pro Arg Leu Lys
1               5

<210> SEQ ID NO 74
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 74

Val Thr Gly Tyr Leu Tyr Leu
1               5

<210> SEQ ID NO 75
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 75

Ala Gly Gly Gly Gly Gly Lys
1               5

<210> SEQ ID NO 76
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (4)..(4)
<223> OTHER INFORMATION: Xaa can be any naturally occurring amino acid

<400> SEQUENCE: 76

Gly His Arg Xaa Val Val Arg
1               5

<210> SEQ ID NO 77
<211> LENGTH: 5
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 77

Gly Val Leu Asp Gly

<210> SEQ ID NO 78
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 78

Asn Lys His Thr Thr Met Ser
1               5

<210> SEQ ID NO 79
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (2)..(2)
<223> OTHER INFORMATION: Xaa can be any naturally occurring amino acid

<400> SEQUENCE: 79

Ser Xaa Gly His His Pro Thr
1               5

<210> SEQ ID NO 80
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 80

Ser Pro Leu Val Leu Tyr Leu
1               5

<210> SEQ ID NO 81
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 81

Val Lys Lys Ser Asn Asp Ala
1               5

<210> SEQ ID NO 82
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 82

Val Lys Lys Ser Asn Asp Ala
1               5

<210> SEQ ID NO 83
<211> LENGTH: 7

```
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 83

Ala Lys Arg Arg Ala Trp Glu
1               5

<210> SEQ ID NO 84
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 84

Gly Phe Val Phe Leu Val Gly
1               5

<210> SEQ ID NO 85
<211> LENGTH: 6
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 85

Gly Gly Val Asp Glu Glu
1               5

<210> SEQ ID NO 86
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 86

Ser Leu Thr Ala His Leu Ala
1               5

<210> SEQ ID NO 87
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 87

Val Leu Ile Gly Asp Gly Gly
1               5

<210> SEQ ID NO 88
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 88

Val Leu Thr Gly Glu Gly Gly
```

<210> SEQ ID NO 89
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 89

Ala Val Ser Cys Ile Ile Thr
1               5

<210> SEQ ID NO 90
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 90

Val Arg Leu Leu Phe Tyr Ala
1               5

<210> SEQ ID NO 91
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 91

Glu Asn Pro Lys Thr Arg Val
1               5

<210> SEQ ID NO 92
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 92

Phe Arg Leu Leu Phe Tyr Pro
1               5

<210> SEQ ID NO 93
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 93

Ile Met Pro Met Pro Thr Thr
1               5

<210> SEQ ID NO 94
<211> LENGTH: 7
<212> TYPE: PRT
<213> ORGANISM: artificial
<220> FEATURE:
<223> OTHER INFORMATION: amino acid sequence of AB-loop fiber-modified adenovirus clone

<400> SEQUENCE: 94

Val Ser Ile Asn Arg Ser Ala
1               5

<210> SEQ ID NO 95
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 95

Ala Trp Gly Gly Val Val Arg
1               5

<210> SEQ ID NO 96
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 96

Cys Arg Leu Asn Ala Glu Lys
1               5

<210> SEQ ID NO 97
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 97

Phe Gln Arg Gly Asn Cys Asp
1               5

<210> SEQ ID NO 98
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (4)..(4)
<223> OTHER INFORMATION: Xaa can be any naturally occurring amino acid

<400> SEQUENCE: 98

Met Lys Gln Xaa Pro Val Val
1               5

<210> SEQ ID NO 99
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 99

Val Arg Leu Leu Leu Tyr Pro

<210> SEQ ID NO 100
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 100

Tyr Leu Pro Gln Pro Pro Ser
1               5

<210> SEQ ID NO 101
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 101

Val Arg Leu Leu Ser Tyr Pro
1               5

<210> SEQ ID NO 102
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 102

Phe His Arg Gly Asn Cys Asp
1               5

<210> SEQ ID NO 103
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 103

Val Lys Leu Leu Phe Tyr Pro
1               5

<210> SEQ ID NO 104
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 104

Val Arg Leu Leu Phe Ser Pro
1               5

<210> SEQ ID NO 105
<211> LENGTH: 7
<212> TYPE: PRT
<213> ORGANISM: artificial
<220> FEATURE:
<223> OTHER INFORMATION: amino acid sequence of AB-loop fiber-modified adenovirus clone

<400> SEQUENCE: 105

Gly Glu Arg Ser Gly Arg Trp
1               5

<210> SEQ ID NO 106
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 106

Thr Tyr Met Leu Ser Arg Asn
1               5

<210> SEQ ID NO 107
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 107

Val Arg Leu Leu Phe Tyr Pro
1               5

<210> SEQ ID NO 108
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 108

Leu Ser Gly Glu Pro Leu Val
1               5

<210> SEQ ID NO 109
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (6)..(6)
<223> OTHER INFORMATION: Xaa can be any naturally occurring amino acid

<400> SEQUENCE: 109

Gln Asp Val Asn Arg Xaa Gln
1               5

<210> SEQ ID NO 110
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 110

Gly Glu Glu Gly Ser Gly Arg

```
<210> SEQ ID NO 111
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 111

Ala Ser Leu Phe Val Leu Arg
1               5

<210> SEQ ID NO 112
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 112

Ala Met Ile Ala Thr Ala Ala
1               5

<210> SEQ ID NO 113
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 113

Ala Cys Phe Thr Cys Pro Ser
1               5

<210> SEQ ID NO 114
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 114

Leu Asn Trp His Cys Val Gly
1               5
```

TARGETED ADENOVIRUSES AND METHODS OF MAKING, ISOLATING, AND USING

CROSS-REFERENCE TO RELATED APPLICATION

This application is the § 371 U.S. National Stage of International Application No. PCT/US2015/027554, filed 24 Apr. 2015, which claims priority to U.S. Provisional Patent Application Ser. No. 61/984,602, filed Apr. 25, 2014, each of which is incorporated herein by reference.

GOVERNMENT FUNDING

This invention was made with government support under CA168448 awarded by the National Institutes of Health. The government has certain rights in the invention.

BACKGROUND

Adenovirus (Ad) is one of the most frequently used backbone viruses for the development of oncolytic agents by taking advantage of its high in vivo transduction efficiency. However, lack of primary Ad receptor (Coxsackie adenovirus receptor, CAR) expression is observed in a majority of cancer cells.

SUMMARY

Described herein are adenoviruses comprising an AB-loop comprising a targeting motif, wherein the targeting motif selectively binds to a tumor cell.

In some cases, the targeting motif can include at least one of the following amino acid sequences: GERSGRW (SEQ ID NO:105), TYMLSRN (SEQ ID NO:106), VRLLFYP (SEQ ID NO:107), and VTINRSA (SEQ ID NO:12).

In some cases, the targeting motif selectively binds to a prostate cancer cell. In some embodiments, the prostate cancer can include a hormone-refractory, castration-resistant, or androgen receptor-negative prostate cancer cell.

In some cases, the targeting motif selectively binds to a colorectal cancer cell.

In some cases, the targeting motif selectively binds to CD133. In some embodiments, the CD133 is expressed on a cancer stem cell.

In some cases, the targeting motif of the adenovirus selectively binds to a pancreatic cancer cell.

In some cases, the targeting motif selectively binds to mesothelin.

In other aspects, we describe herein a method including administering any of the adenoviruses described above via systemic administration. In some cases, the systemic administration is via intravenous injection.

In another aspect, we describe herein a method that includes administering any of the adenoviruses described above via intratumoral injection.

In further aspects, we describe herein a method that includes identifying adenovirus vector structures useful for systemic targeting including adding a recombinant adenovirus library to a culture of host cells, wherein the host cells overexpress an antigen; collecting crude viral lysate and re-infecting a culture of host cells with adenovirus in the crude viral lysate; and isolating an adenovirus specific to the antigen overexpressed by the host cells.

In some cases, the method further includes one or more additional rounds of collecting crude viral lysate and re-infecting the host cell with adenovirus in the crude viral lysate.

In some cases, the recombinant adenovirus library comprises an order of diversity of at least $1\times10^9$.

In some cases, the recombinant adenovirus library comprises adenoviruses comprising a targeting motif. In some embodiments, the targeting motif is located with the AB-loop region of the adenovirus.

In some cases, the host cell is a cancer cell line. In some embodiments, the cancer cell line is PC-3.

In some cases, the antigen is unknown. In some cases, the antigen is CD133.

In another aspect, we describe herein a method including identifying adenovirus vector structures useful for systemic targeting including introducing an recombinant adenovirus library into a host comprising tumor comprising cells, wherein the cells overexpress an antigen; and isolating an adenovirus specific to the antigen overexpressed by the cells.

In some cases, the host is a mouse. In some embodiments, the mouse is a nude mouse.

In some cases, introducing a recombinant adenovirus library comprises intravenously injecting the recombinant adenovirus library.

In some cases, the recombinant adenovirus library comprises an order of diversity of at least $1\times10^9$.

In some cases, the recombinant adenovirus library comprises adenoviruses comprising a targeting motif. In some embodiments, the targeting motif is located with the AB-loop region of the adenovirus.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 4:
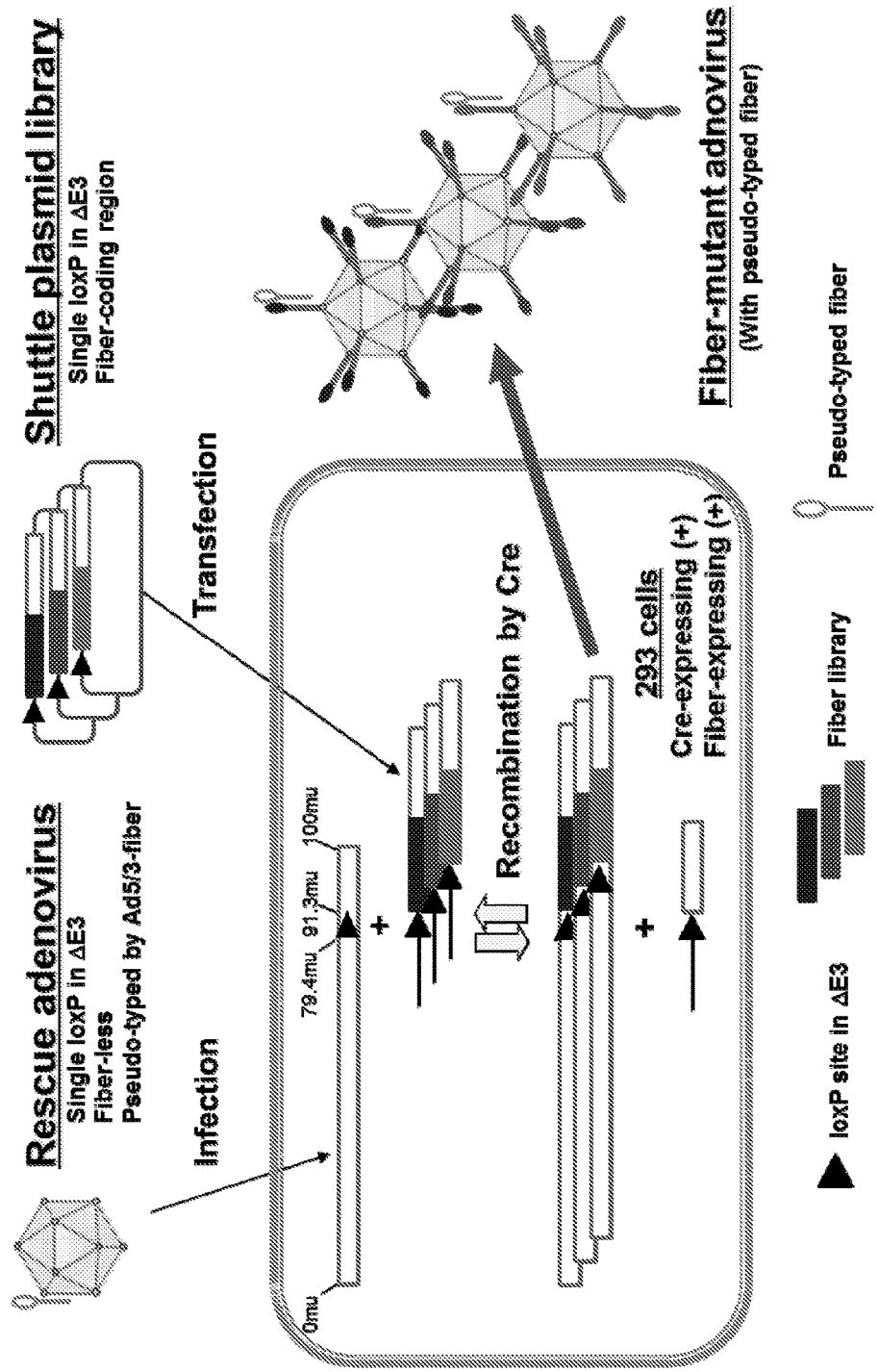
Figure 5A:
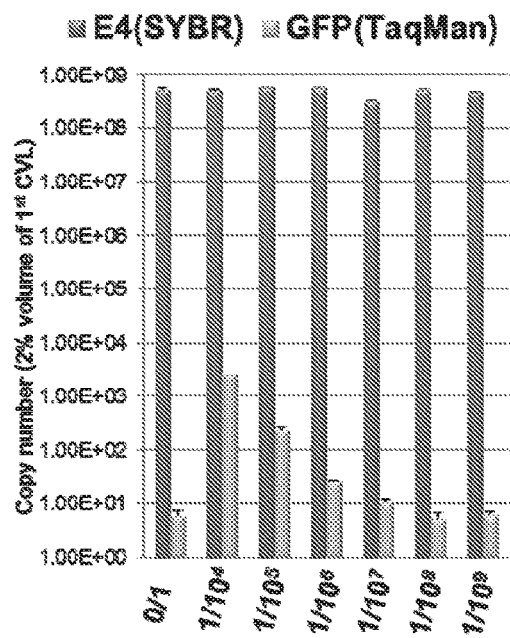
Figure 5B:
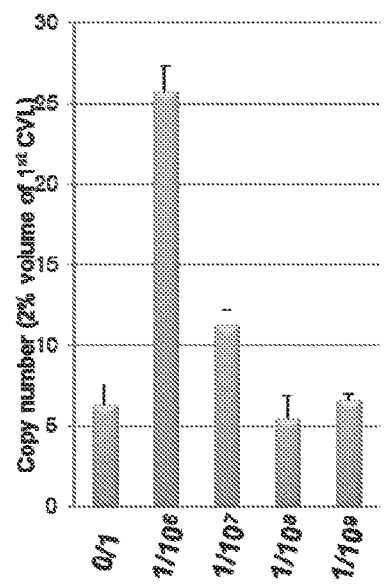
Figure 5C:
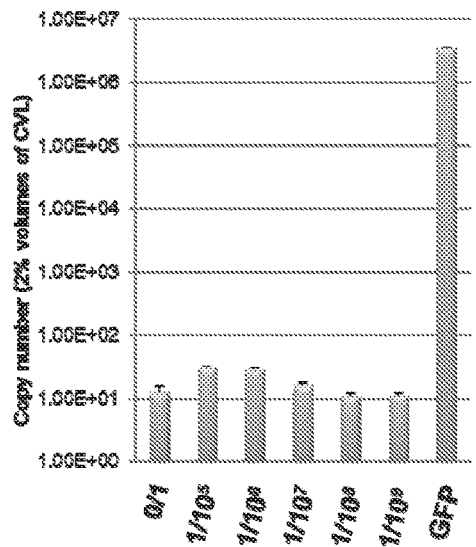
Figure 5D:
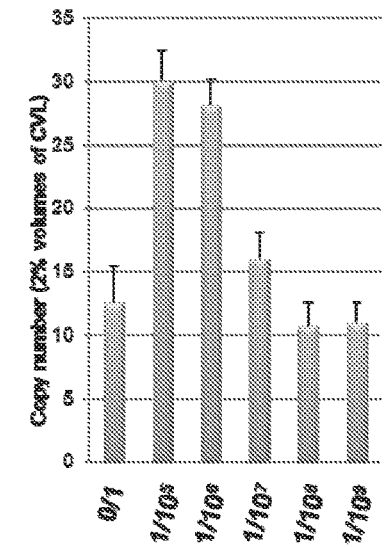

FIG. 4. Strategy for constructing fiber-mutant adenovirus library. The fiber-modified plasmid library was transfected into 293-CRE-69 cells, which had been infected with the rescue virus 24 hours before and 48 hours after the transfection, the first generation of the adenovirus library was produced.

FIG. 5. Efficiency of EGFP-expressing adenovirus production from fiber-modified adenovirus library. Dilution experiments with shuttle plasmid library and shuttle plasmid expressing GFP. (a), (b) HI-loop modified library. The pBHIΔCAR-GFP were mixed with pBHIΔCAR-lib at various ratios (1:1×10$^4$, 1:1×10$^5$, 1:1×10$^6$, 1:1×10$^7$, 1:1×10$^8$, and 1×10$^9$), and transfected with the rescue virus into 293-CRE-69 cells. (c), (d) AB-loop modified library. The pBHIΔCAR-GFP were mixed with pMLAB-lib at various ratios (1:1×10$^4$, 1:1×10$^5$, 1:1×10$^6$, 1:1×10$^7$, 1:1×10$^8$, and 1×10$^9$), and transfected with the rescue virus into 293-CRE-69 cells. The CVL were collected two days after the transfection, 2% volumes of the crude viral lysates were treated with DNaseI, the viral DNA was extracted, and then subjected to quantitative PCR. Total viral copy numbers were determined by SYBRGreen with E4 primers; recombinant viral copy numbers were determined by Taqman Probe for GFP gene. Each bar represents the mean of three experiment±SD. (a), (c) logarithmic scale. (b), (d) actual number.

Figure 6:
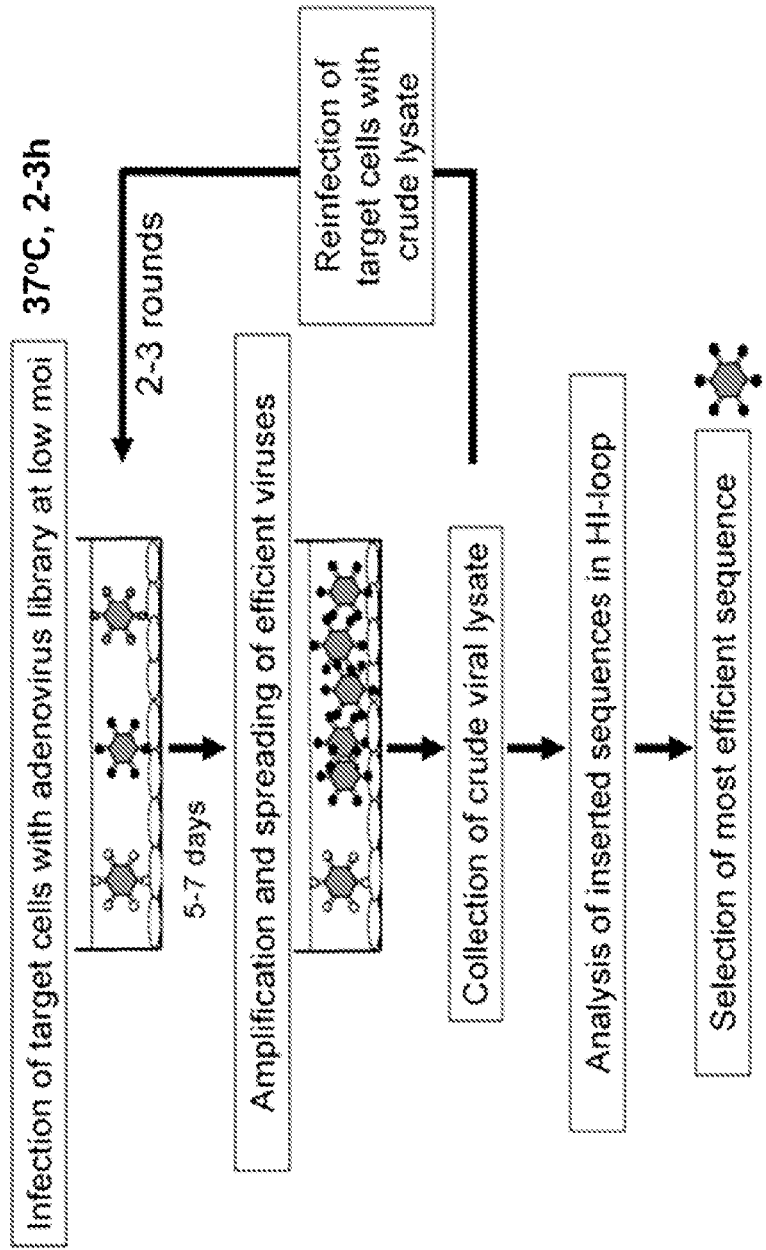

FIG. 6. Screening strategy of adenovirus library. First, the target cells were infected with the adenovirus library at a low multiplicity of infection. Next, the expanded adenoviruses are recovered from the cells and subjected to two or three more rounds of selection. The DNA region containing fiber-mutant of the selected adenoviruses is then analyzed.

FIG. 7. Binding and replication assay of AB-mutants virus pool from the 3$^{rd}$ round screening on Panc1 cells. (a) Viral replication in Panc1 cells. Panc1 cells were infected with 0.1 vp/cell of the AB-mutants virus pool from the third round screening on Panc1 cells at 37° C. for two hours. Cells were harvested on Day 2 and Day 5 after the infection and then subjected to qPCR. 2% volumes of the crude viral lysates were treated with DNaseI, the viral DNA extracted, and then subjected to quantitative PCR, which detected total viral copy numbers by SYBRGreen with E4 primers. (b) Viral binding to Panc1 cells. 100 vp/cell of the AB-mutants virus pool from the third round screening on Panc1 cells at 4° C. for two hours. Cells were harvested immediately after the infection and then subjected to qPCR. 2% volumes of the CVL were treated with DNaseI, the viral DNA extracted, and then subjected to quantitative PCR, which detected total viral copy numbers by SYBRGreen with E4 primers.

FIG. 8. In order to determine diversity, limit-dilution experiments with the shuttle plasmid library mixed with the GFP-coding shuttle plasmid were performed. A small amount of pBΔCAR-GFP was mixed with pMLAB-lib at various ratios, and Ad libraries were generated from the mixtures. The viral DNA was extracted from the viral solution after treatment with DNaseI, and then recombinant viral copy numbers were determined by qPCR for GFP sequence. When 1/20 amount of the viral solution was assessed, the GFP sequence coding virus was detected in a 4×10$^7$ dilution.

Figure 9:
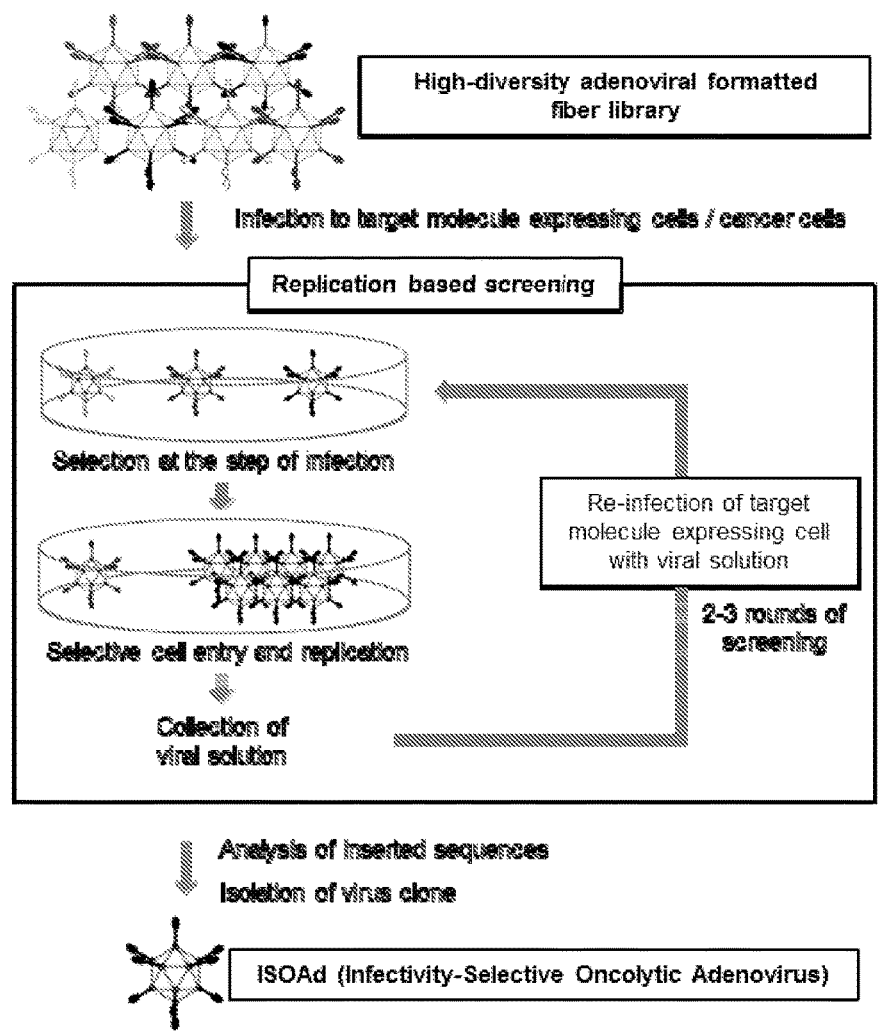

FIG. 9. High-throughput screening of the adenovirus library in the AB-loop for mesothelin (MSLN) expressing cells. (a) Via the replication-based high-throughput screening, the Infectivity-Selective Oncolytic Adenovirus (ISOAd) was isolated from a high diversity Ad library of targeting motifs based on transduction and subsequent replication. First, the target cells were infected with the Ad library at a low multiplicity of infection (MOI). After 5-7 days, the amplified Ads were recovered from the cells and subjected to a few more rounds of re-infection. The viral solution from each round was harvested and the sequences of the targeting motifs were analyzed. (b) The DNA sequences of the AB-loop region of the Ads screened with 293-MSLN cells were amplified by PCR and analyzed after cloning into a plasmid. While the initial library sequence was completely diverse, screening after virus amplification in 293-MSLN cells started to show convergence of the targeting motif sequences as early as the first round of screening. After subsequent rounds of screening, the sequence further converged eventually to a single clone (VTINRSA, SEQ ID NO:12).

FIG. 10. Binding of the isolated adenovirus clone to mesothelin. (a) Binding ability of AdML-VTIN correlated well with mesothelin (MSLN) expression in various cell lines (293, 293-MSLN, Panc-1, A549, MiaPaCa-2, and AsPC-1). Binding of AdML-5WT (control Ad with a wild type fiber) did not correspond to the MSLN level. The isolated total DNA was analyzed by the E4 qPCR to determine the adenoviral copy number bound to the surface of the cells. The level of MSLN expression was determined by flow-cytometry (shown below the graph). (b) Flow-cytometry of cell surface mesothelin. Expression of mesothelin was determined by flow-cytometry. Shaded: without anti-mesothelin antibody, Black-line; with anti-mesothelin antibody. (c) Suppression of MSLN expression with the anti-MSLN siRNA eliminated AdML-VTIN binding to the target cells (: P<0.01, *: P<0.001). (d) Pre-treatment with the anti-MSLN antibody (two hours at 4° C.) significantly reduced binding of AdML-VTIN to the MSLN-positive target cells.

FIG. 11. The inhibition of mesothelin (MSLN) expression with the anti-MSLN siRNA eliminated AdML-VTIN binding to the target cells. (a) Expression of cell surface MSLN was determined by flow-cytometry after the treatment with the anti-MSLN siRNA. Shaded: without anti-MSLN antibody, Black-line: with anti-MSLN antibody. (b) Suppression of MSLN expression with the anti-MSLN siRNA eliminated AdML-VTIN binding to the Panc-1 cells. Mock transfection controls received only the transfection reagent. After the treatment with the siRNA, the binding assay was performed. (**: P<0.01).

FIG. 12. Characterization of the newly isolated adenovirus AdML-VTIN. (a) The analysis of infectivity demonstrated that the MSLN-targeted AdML-VTIN outperformed not only the control Ad with a native fiber (AdML-5WT) but also the infectivity-enhanced Ad with an Ad5/Ad3-fiber (AdMG553) in MSLN strongly-positive Panc-1. In MSLN-intermediately positive A549 cells, the infectivity of AdML-VTIN was as high as that with AdMG553. However, its binding to MSLN-negative MiaPaCa-2 and AsPC-1 cells was significantly lower than other vectors. (b) AdML-VTIN showed exponential amplification selectively in MSLN positive cells (Panc-1 and A549), and the extent of virus burst corresponded with the MSLN level of each cell line.

The result was shown as a virus burst size (vp/cell) (n=3). Mesothelin expression: strong (2+), moderate (+), low (−).

FIG. 13. In vivo anti-tumor effect and viral replication of the infectivity-selective oncolytic adenovirus (ISOAd). (a) The in vivo anti-tumor effect of the mesothelin-targeted AdML-VTIN was analyzed in Panc-1 (MSLN-positive) and MiaPaCa-2 (MSLN-negative) subcutaneous xenografts. AdML-VTIN showed a strong anti-tumor effect only in the MSLN expressing Panc-1 tumors, while the effect of AdML-5WT was not selective. Each symbol represents the mean of tumor volumes±s.e.m. (n=4-8) (*: P<0.05, : P<0.01). (b) Five days after intratumoral injection of the viruses, the expression of an adenoviral late gene product (hexon) was assessed by immunostaining with the anti-hexon polyclonal antibody (counterstained with Hoechst 33342). Staining and sections were performed in at least two independent experiments. Green: adenovirus hexon protein, Blue: nucleus (original magnification: ×100). (c) The viral copy numbers in the DNA isolated from tumor specimens at day 5 were analyzed by qPCR. The result is shown as the adenoviral copy number per 1 ng DNA. (*: P<0.005) Mesothelin expression: strong (2+), moderate (+), low (−).

FIG. 14. In vivo distribution of the novel fiber-modified virus after systemic administration. A) 48 hours after injection. The novel fiber modified virus generated with our novel technique (AdML-VTIN) was injected into the tail vein of the mice. The virus distribution in the tumor and major organs was analyzed by virus DNA qPCR at 48 hours after injection. B) Virus distribution seven days after injection. The tumor distribution of the VTIN virus was more than three orders of magnitude higher than the wild type virus.

Figure 15:
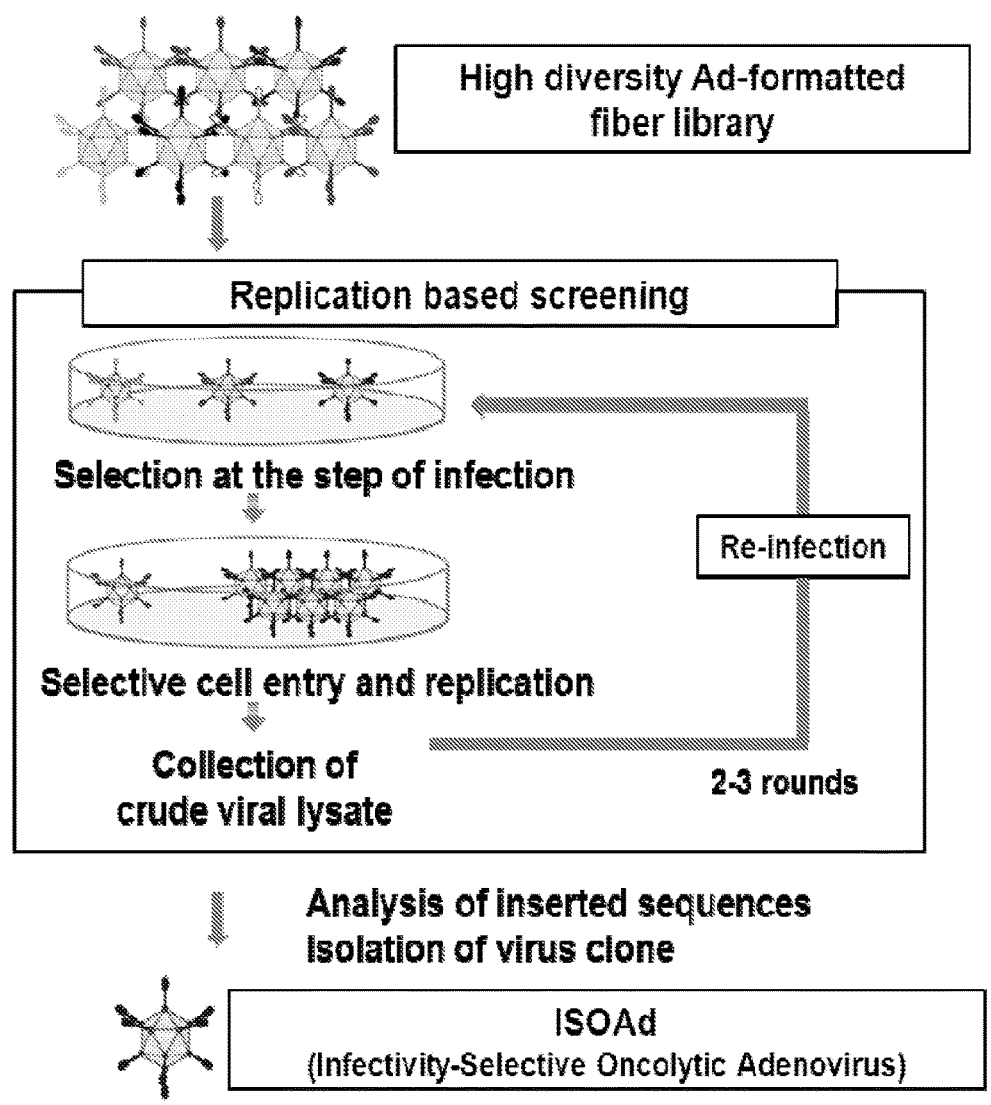

FIG. 15. Screening strategy. First, 293 cells overexpressing CD133 (293-CD133) are infected with the adenovirus library. Next, the expanded adenoviruses are recovered from the cells and subjected to two or three more rounds of selection. The DNA region containing fiber-mutant of the selected adenoviruses is then analyzed.

Figure 16A:
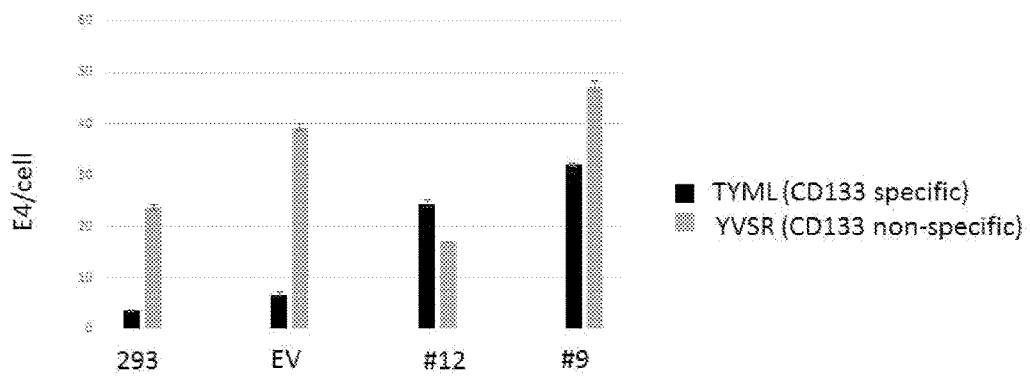
Figure 16B:
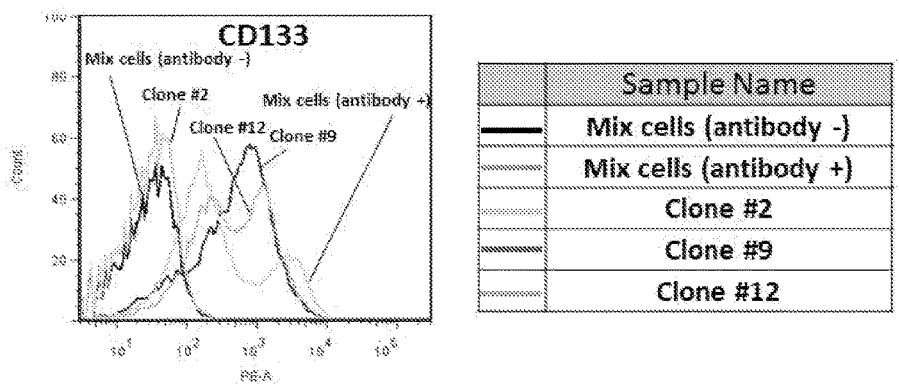

FIG. 16. Selective binding of TYML virus to CD133-overexpressing 293 cells. (a) Adenoviral copy number bound to the surface of the cells was analyzed by E4 qPCR. TYML virus showed higher binding on CD133-overexpressing 293 cells (Clones #9 and #12?) than on non-transfected cells (293) or cells transfected with an empty vector (EV). Virus with a non-selective motif (YVSR) did not show higher binding on CD133-overexpressing cells. (b) Expression of CD133 on 293 cells transfected with CD133 (clones #2, #9, and #12) was measured by staining with PE-labeled anti-CD133 monoclonal antibody (CD133/2 (293C3)-PE) and analyzing by flow cytometry. Mix cells represent a multi-clonal population of CD133-overexpressing 293 cells.

Figure 17:
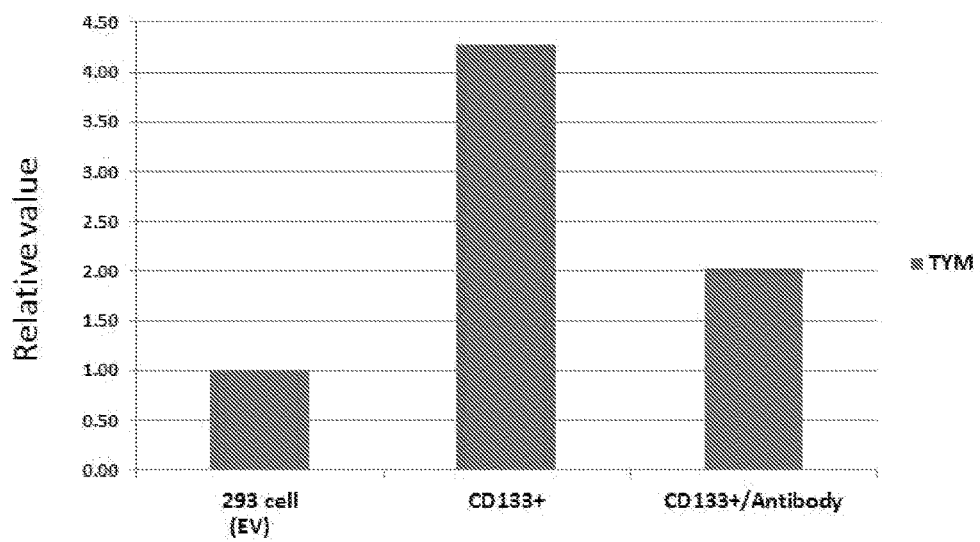

FIG. 17. Blocking of viral binding by anti-CD133 antibody. In order further test selectivity, a binding assay was performed with and without blocking of CD133 by anti-CD133 antibody. TYML virus binds to CD133(+) cells 4 times better than CD133(−) 293 cells, and the anti-CD133 Ab reduced the binding of TYML virus by 50% or more, indicating targeting selectivity of TYML motif to CD133.

Figure 18:
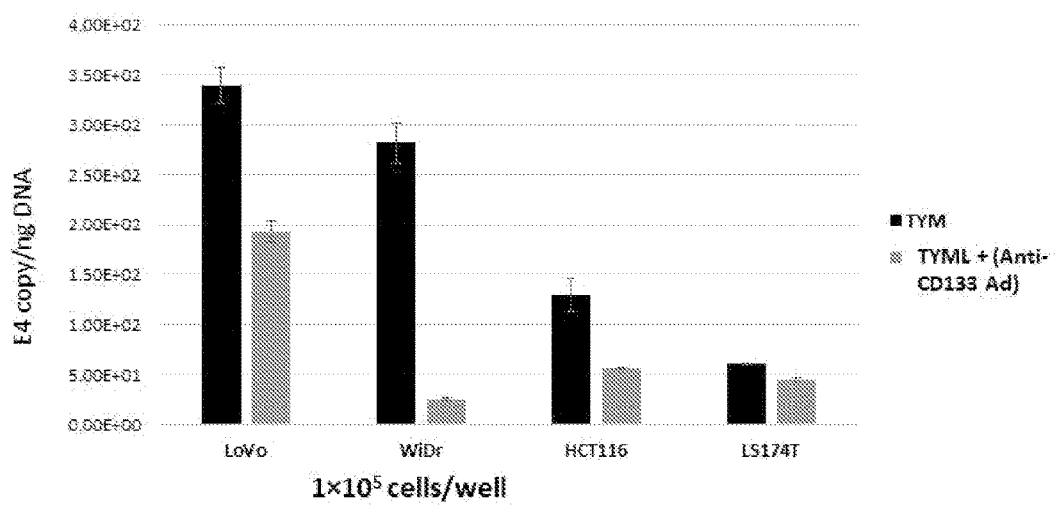

FIG. 18. Binding of TYML virus to colon cancer cells. Colon cancer cell lines expressing CD133 (LoVo, WiDr and HCT116) show good transduction with TYML virus, and pre-incubation with anti-CD133 Ab lower the binding by 45-90%. On the other hand, CD133-negative LS174T shows the least transduction with TYML virus and the binding was not affected by anti-CD133 Ab.

Figure 19:
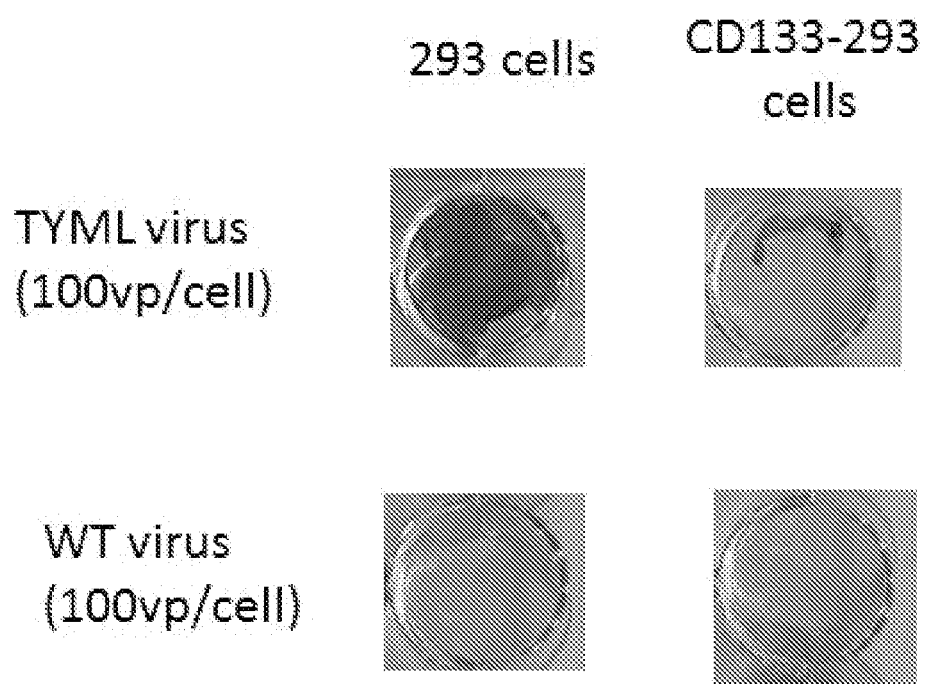

FIG. 19. Selective cytocidal effect of TYML virus. In 293 cells with/without overexpression of CD133 infected with TYML virus and virus with wild type fiber, TYML virus shows strong cytocidal effect only in CD133-overexpressing 293 cells. On the other hand, the virus with wild type fiber eliminated 293 cells regardless of CD133 expression.

Figure 20B:
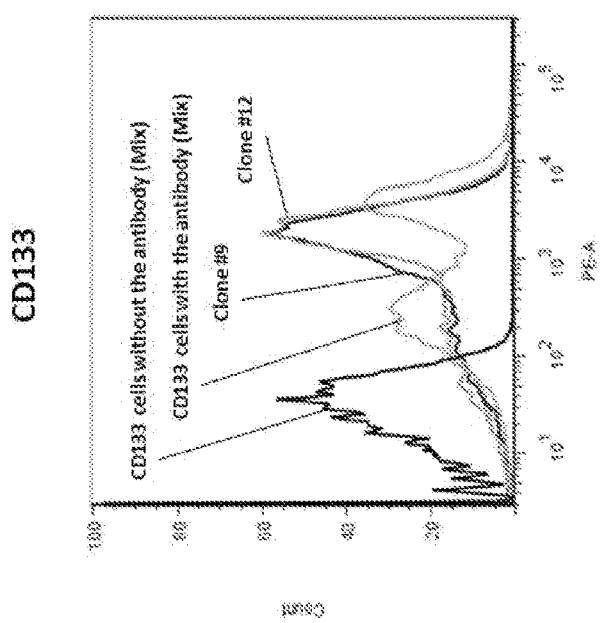
Figure 20A:
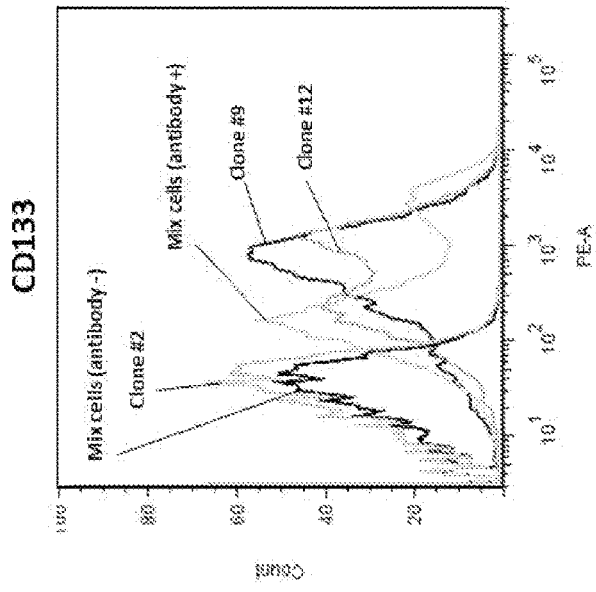

FIG. 20. (a), (b) CD133 expression profiles of 293-derived cell lines used in the experiments. Expression of CD133 was measured by staining with PE-labeled anti-CD133 monoclonal antibody (CD133/2(293C3)-PE) and analyzing by flow cytometry. Mix cells represent a multi-clonal population of CD133-overexpressing 293 cells.

Figure 21:
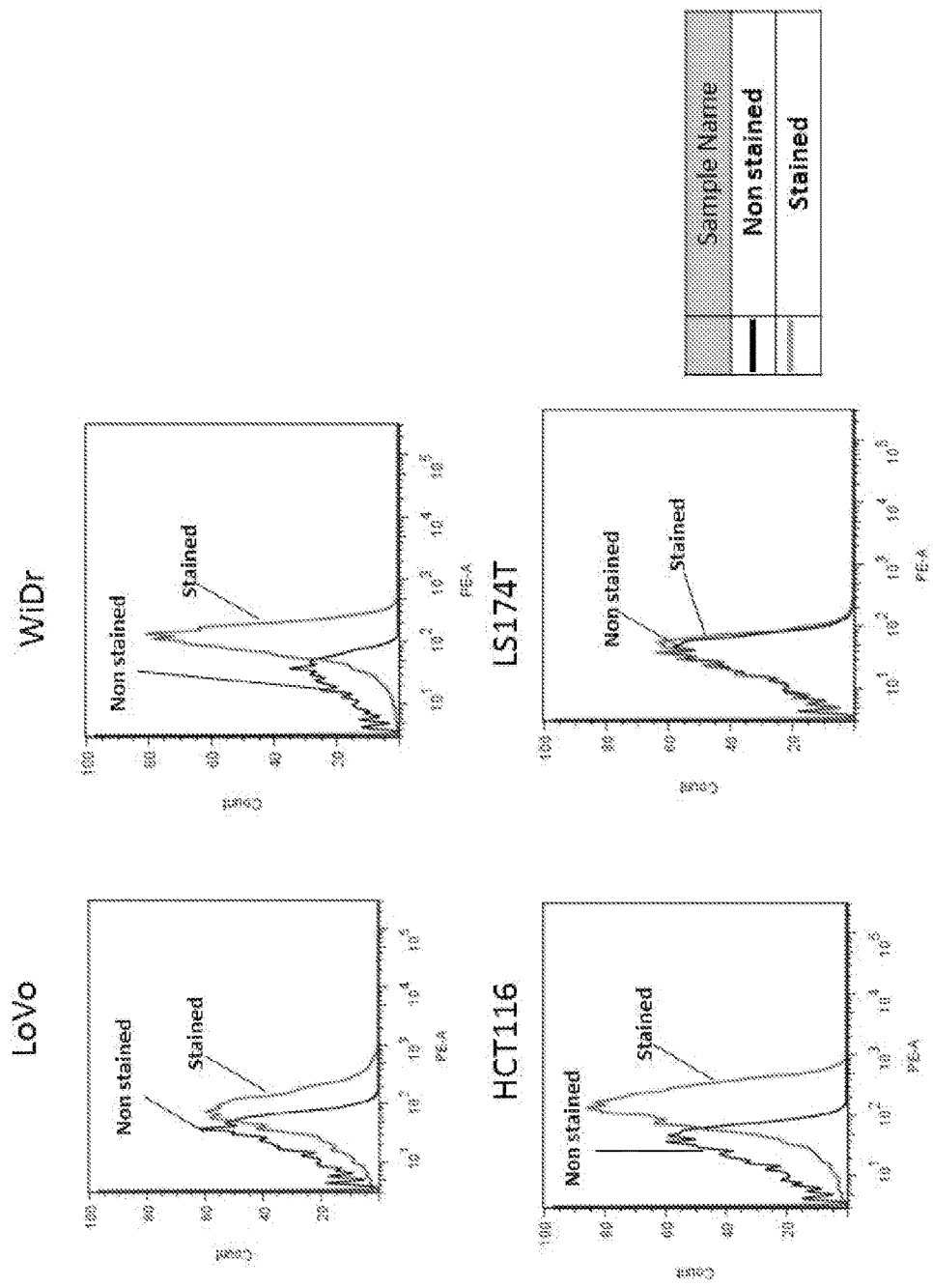

FIG. 21. CD133 expression in colon cancer cell lines.

Figure 22:
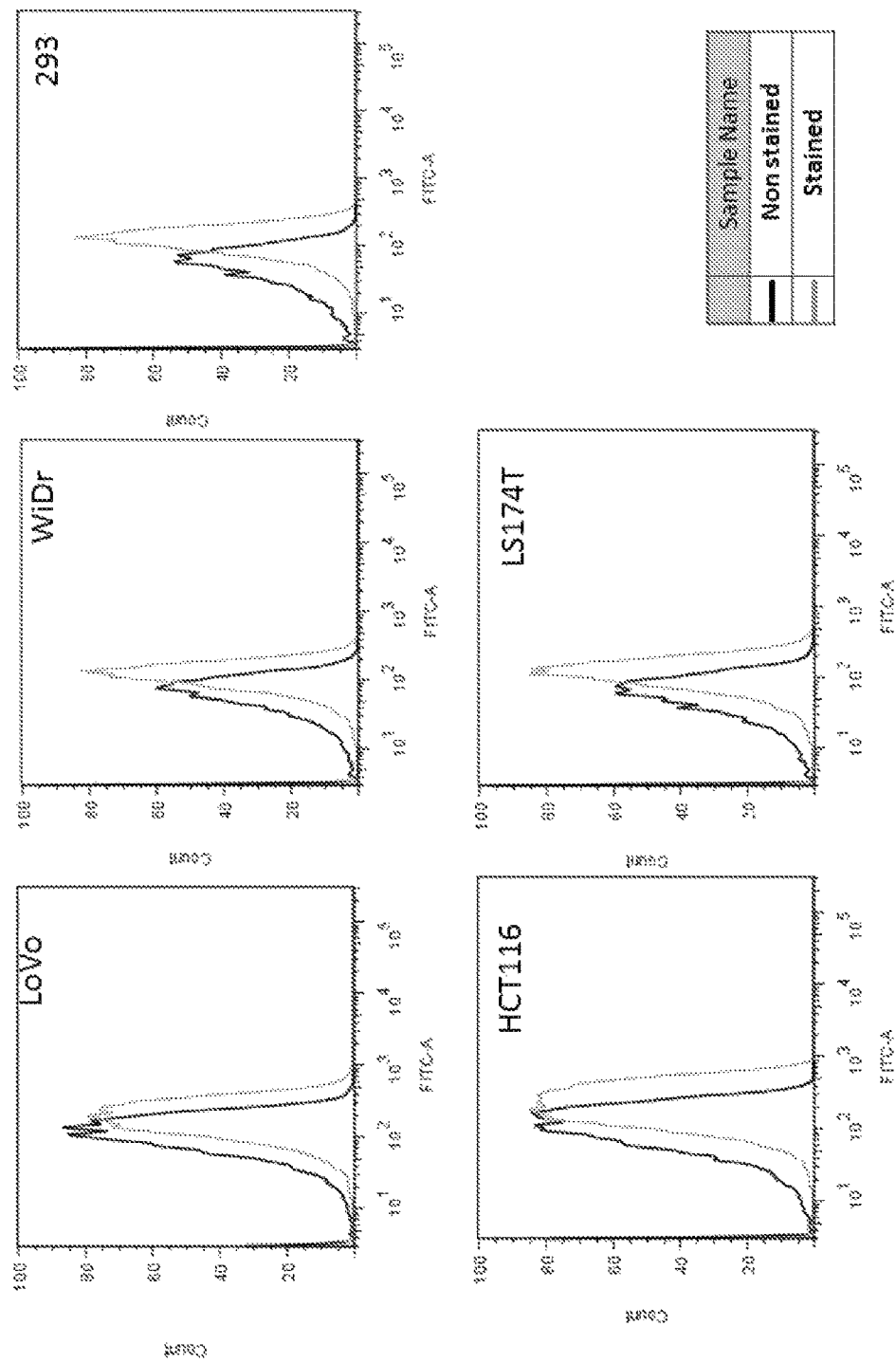

FIG. 22. Coxsackie Adenovirus Receptor (CAR) expression in colon cancer cell lines and 293 cells.

FIG. 23. Schematic of in vitro screening of anti-androgen therapy-resistant cell line.

FIG. 24. In vivo screening strategy with subcutaneous PC3 xenografts. First, a PC3 xenograft was introduced into a nude mouse. Then an adenovirus library was injected intravenously. Either 5 days or 10 after injection of the Ad-library, the mice were sacrificed, DNA was extracted from the tumor, and single clones of adenovirus were isolated and sequenced.

Figure 25:
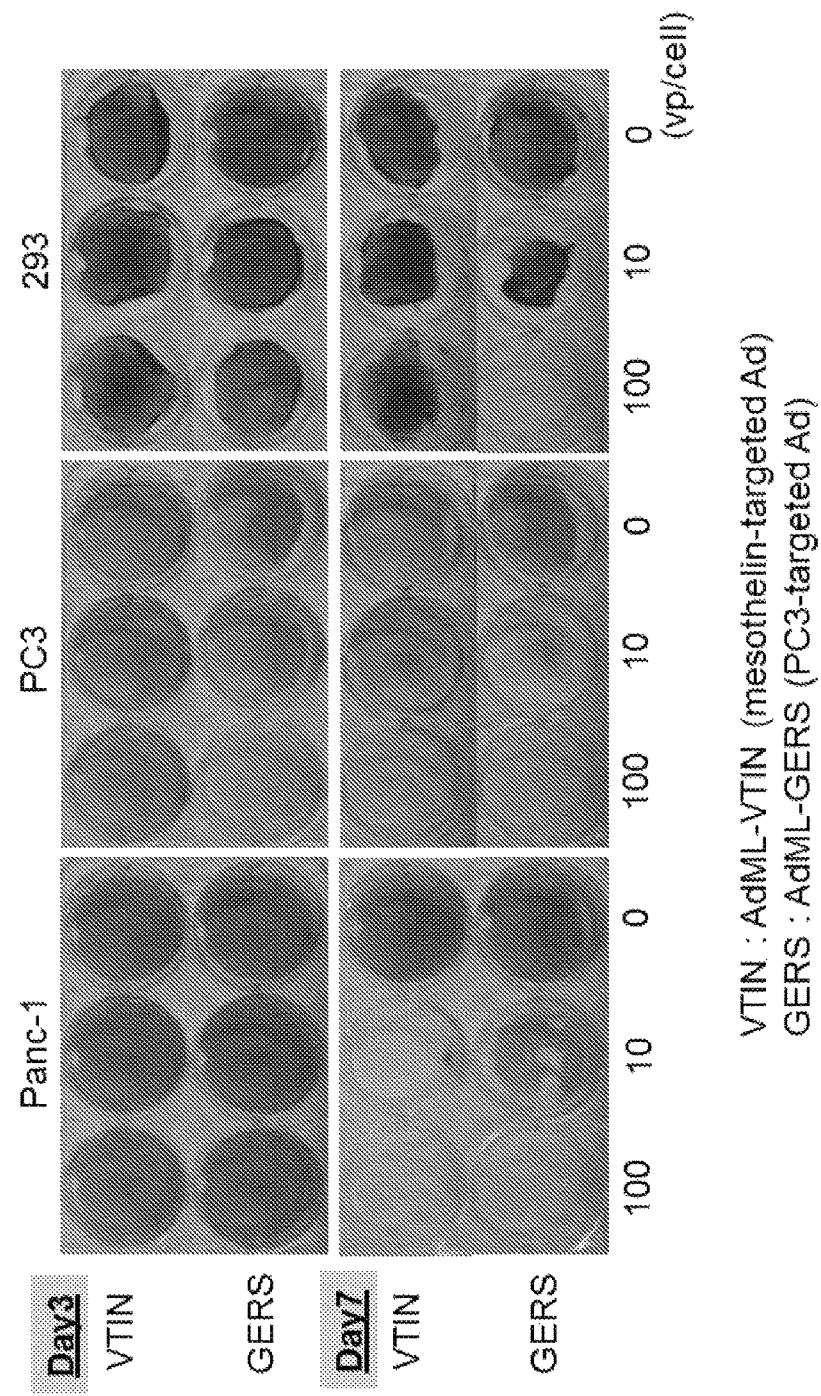

FIG. 25. In vitro testing of GERS-equipped oncolytic adenovirus/Crystal Violet Staining of AdML-VITN and AdML-GERS. When GERS and VTIN(mesothelin targeted) equipped oncolytic adenoviruses were tested for their cytocidal effect in different cells, GERS virus shows enhanced cytocidal effect in PC-3 prostate cancer cells but show no or little effect on panc-1 (pancreatic cancer) cells or 293 cells (transformed embryonic kidney cell).

Figure 26:
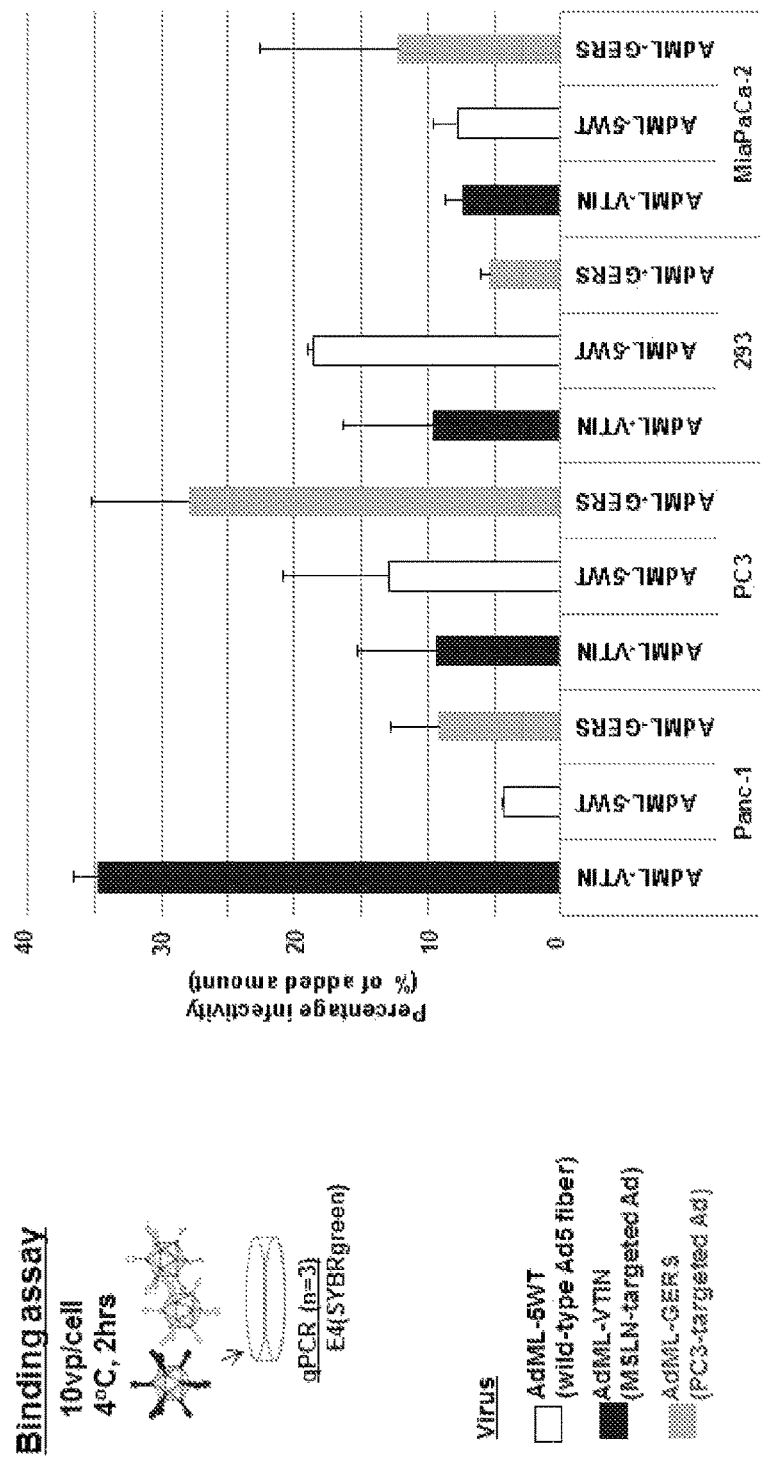

FIG. 26. Selective binding of GERS virus/In vitro binding of AdML-VITN and AdML-GERS. GERS virus was tested for its binding to multiple cell lines. Two hours after inoculation with 10 vp/cell and incubation at 4° C., adenoviral copy number bound to the surface of the cells (Panc-1, PC-3, 293, or MiaPaCa-2) was analyzed by E4 qPCR. GERS virus showed high binding on PC-3 cells compared to other cells, and its binding is stronger than wild type fiber virus or mesothelin-targeted VTIN virus. In mesothelin positive pancreatic cancer cell line (Panc-1) and natural Ad receptor (coxsackie adenovirus receptor, CAR)-abundant cell line (293), VTIN and wild type fiber virus shows best binding. The binding to mesothelin-negative, CAR-negative pancreatic cancer cell line (MiaPaca-2), none of the viruses shows high binding. These data show the selectivity of the GERS equipped virus.

Figure 27:
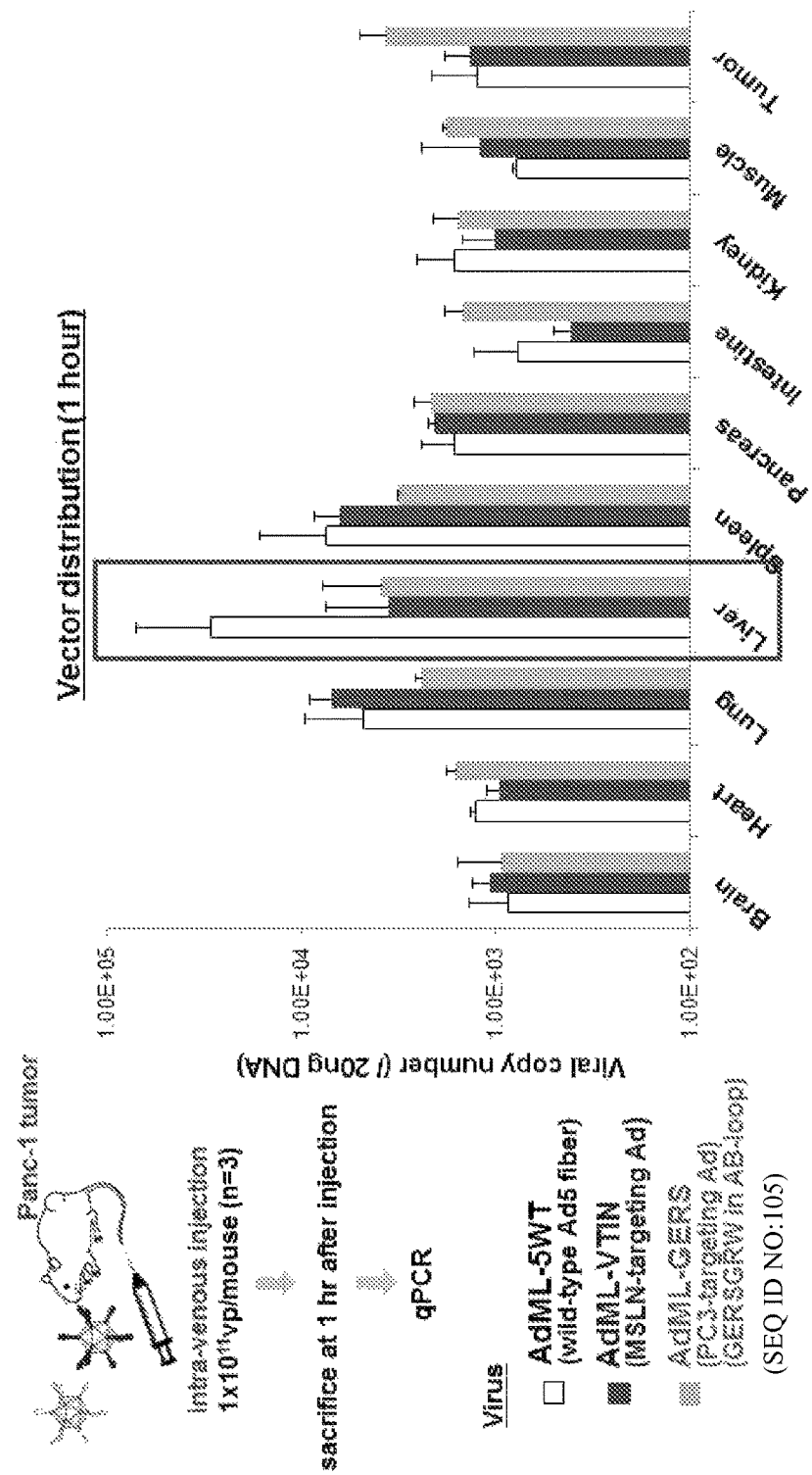

FIG. 27. Systemic persistence of intravenously injected GERS virus. In order to assess systemic persistence, GERS virus ($1\times10^{11}$ vp/mouse) was intravenously injected into Panc-1 subcutaneous tumor-bearing Nude mice. One hour after injection the mice were sacrificed and vector distribution was analyzed by ascertaining viral copy number by qPCR. GERS and VTIN viruses showed more than 1 order reduction of liver sequestration compared to wild type viruses, and GERS virus showed significant reduction of lung sequestration after systemic injection compared to wild-type vector. GERS showed the best intratumoral delivery, which is likely due to lower systemic trapping by the liver and lungs. In this sense, GERS virus possesses beneficial profile for systemic therapy.

Figure 28:
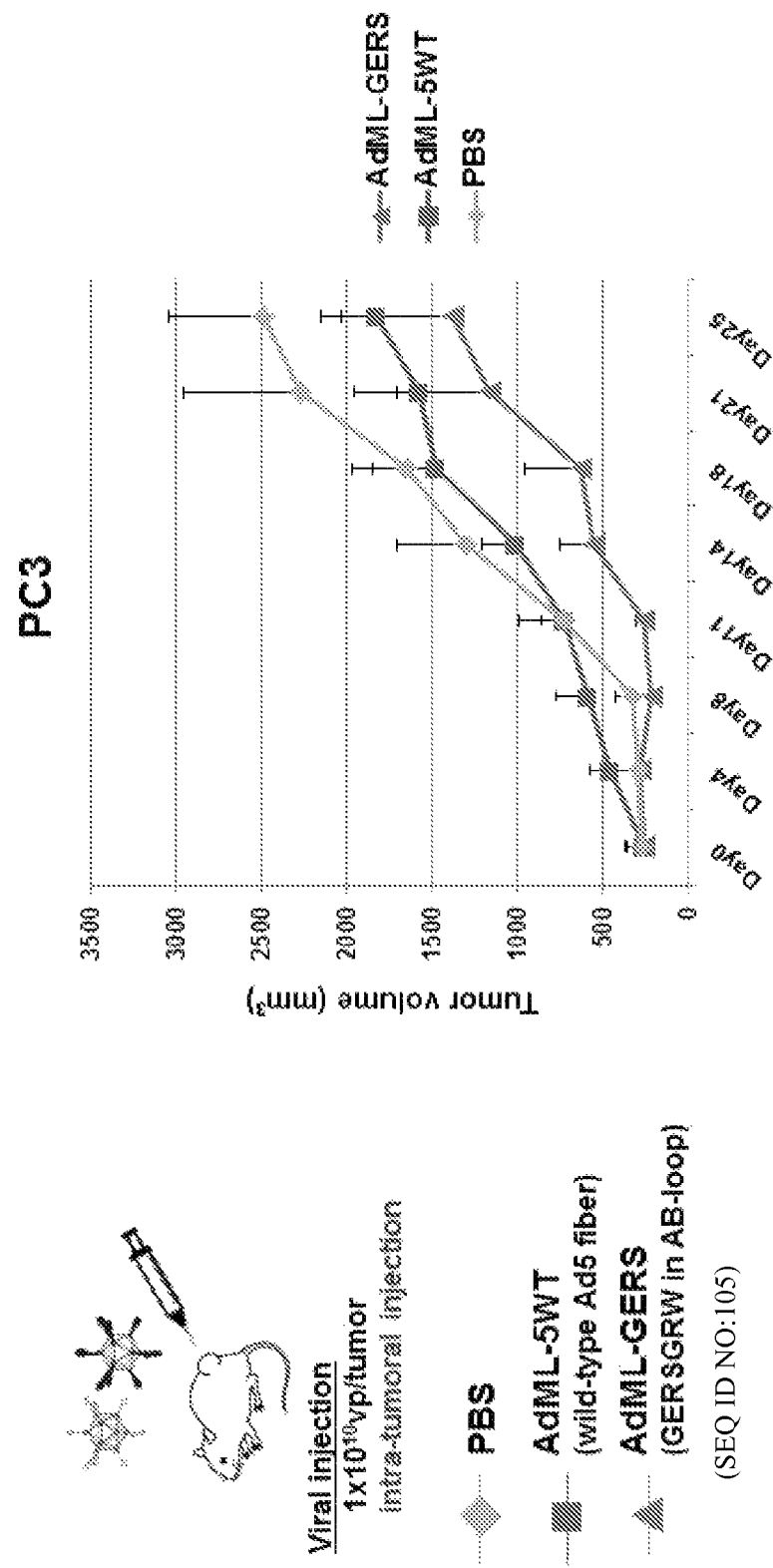

FIG. 28. Antitumor effect of GERS virus after intratumoral injection. Antitumor effect of GERS virus was comparably assessed in PC-3 subcutaneous xenografts. PC-3 subcutaneous xenografts were injected intratumorally with $1\times10^{10}$ vp/tumor. GERS virus showed significant effect compared to PBS group and the group injected with the virus with wild type fiber. (Ad with wild type is known to be usable intratumorally, but not feasible to use in clinic because of non-discretional replication in the human body.) GERS virus showed antitumor effect after intratumoral injection.

Figure 29:
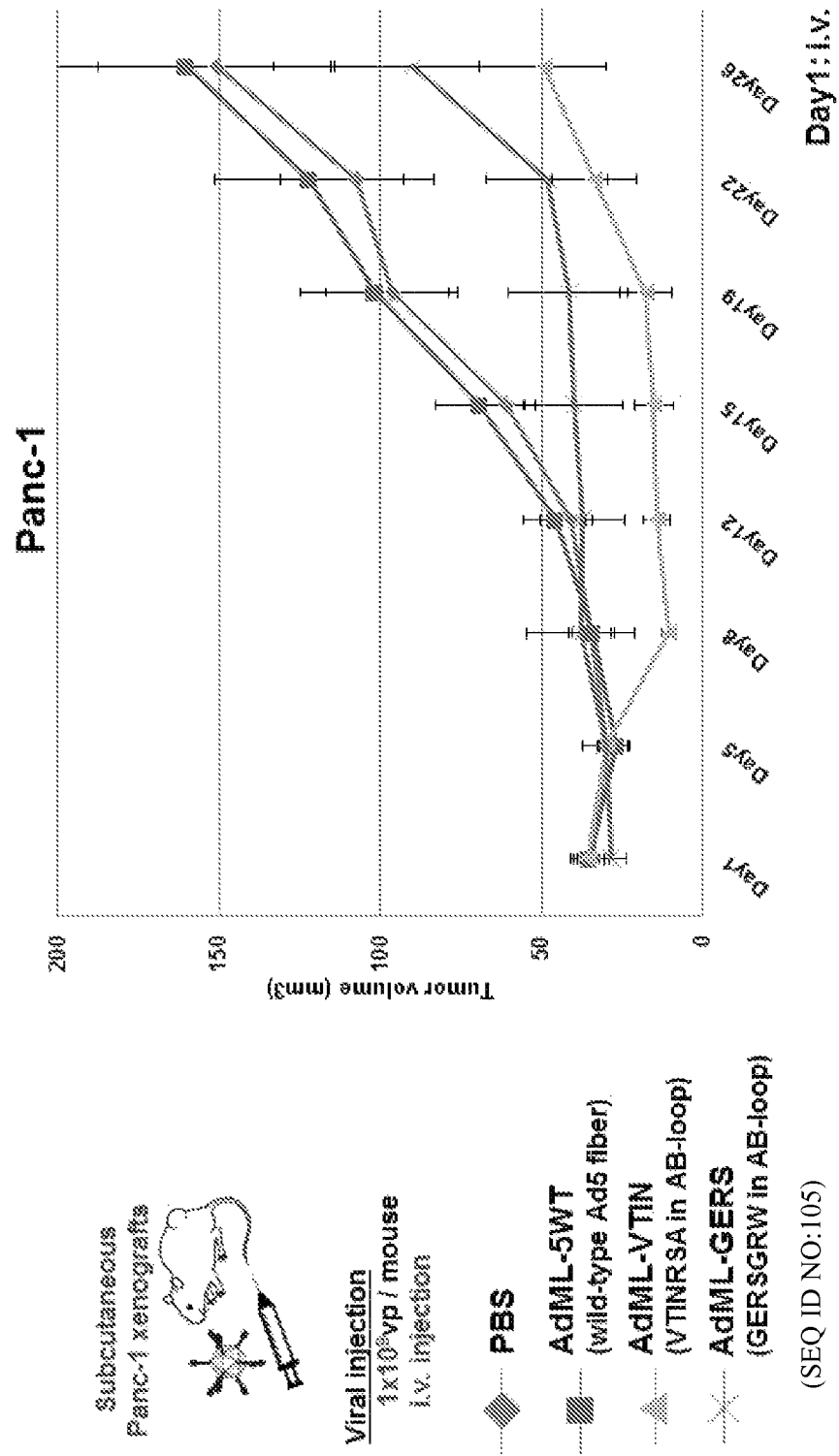

FIG. 29. Antitumor effect of GERS virus after intravenous injection in Panc-1 tumor. AdML-5WT, AdML-VTIN, or AdML-GERS ($1\times10^9$ vp/mouse) or PBS control were intravenously injected into mice having subcutaneous Panc-1 xenografts on day 1, and tumor volume was assessed on days 1 to 26. GERS virus (which is prostate cancer targeted) showed decent antitumor effect even in this pancreatic cancer model. This effect is likely due to the combination of the good distribution profile shown in FIG. 27 and partial cytocidal effect of GERS virus on Panc-1 cells shown in FIG. 25.

Figure 30:
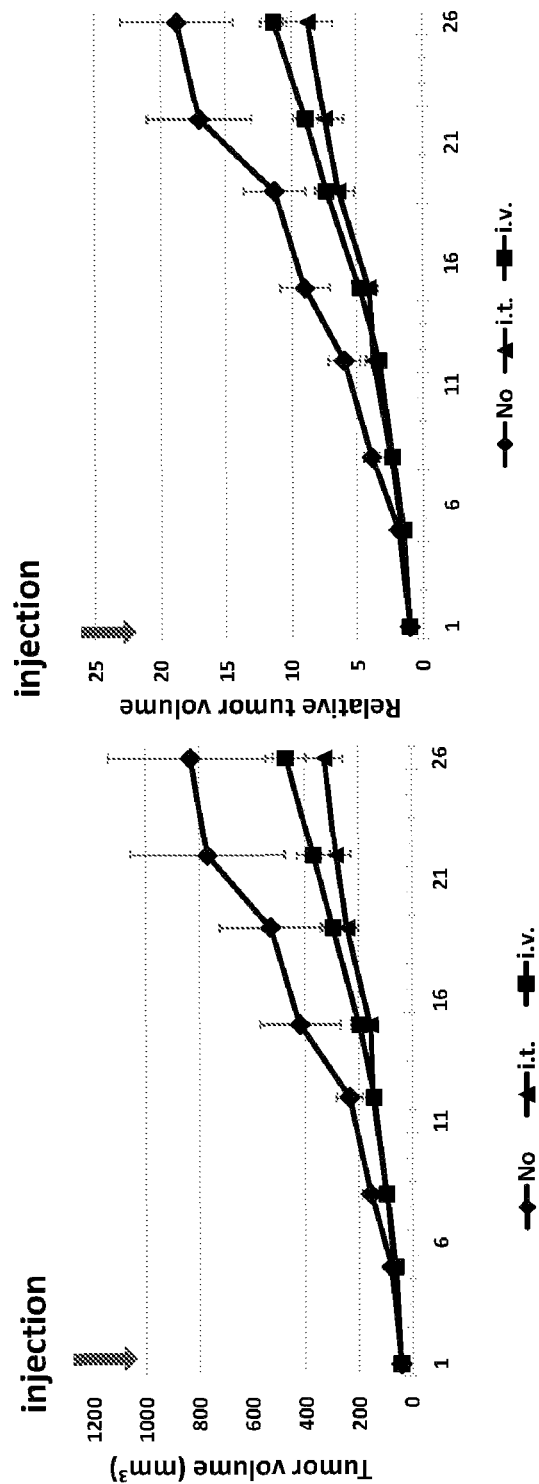

FIG. 30. Treatment Effect of AdML-VTIN for Panc-1 Xenograft (i.t. vs i.v.) (Low Dose: $1.0\times10^9$ vp). In order to analyze the difference of the therapeutic effect of infectivity-selective oncolytic adenovirus (ISOAd), low dose of AdML-VTIN ($1.0\times10^9$ vp/mouse) was injected intratumorally and intravenously into mice bearing MSLN-positive Panc-1 tumors and tumor size was followed. Both i.t. and i.v injected viruses showed significant anti-tumor effect compared to the untreated control. The difference in tumor volume between i.t. and i.v. was statistically insignificant. This difference means that i.v. injection of ISOAd can be as effective as i.t. injection. Relative tumor volume was calculated by using the volume immediately before injection (day 0) as the reference volume. The tumor volume was calculated as width×length/2. (Left panel: the plot of absolute volume. Right panel: the plot of relative volume.)

Figure 31:
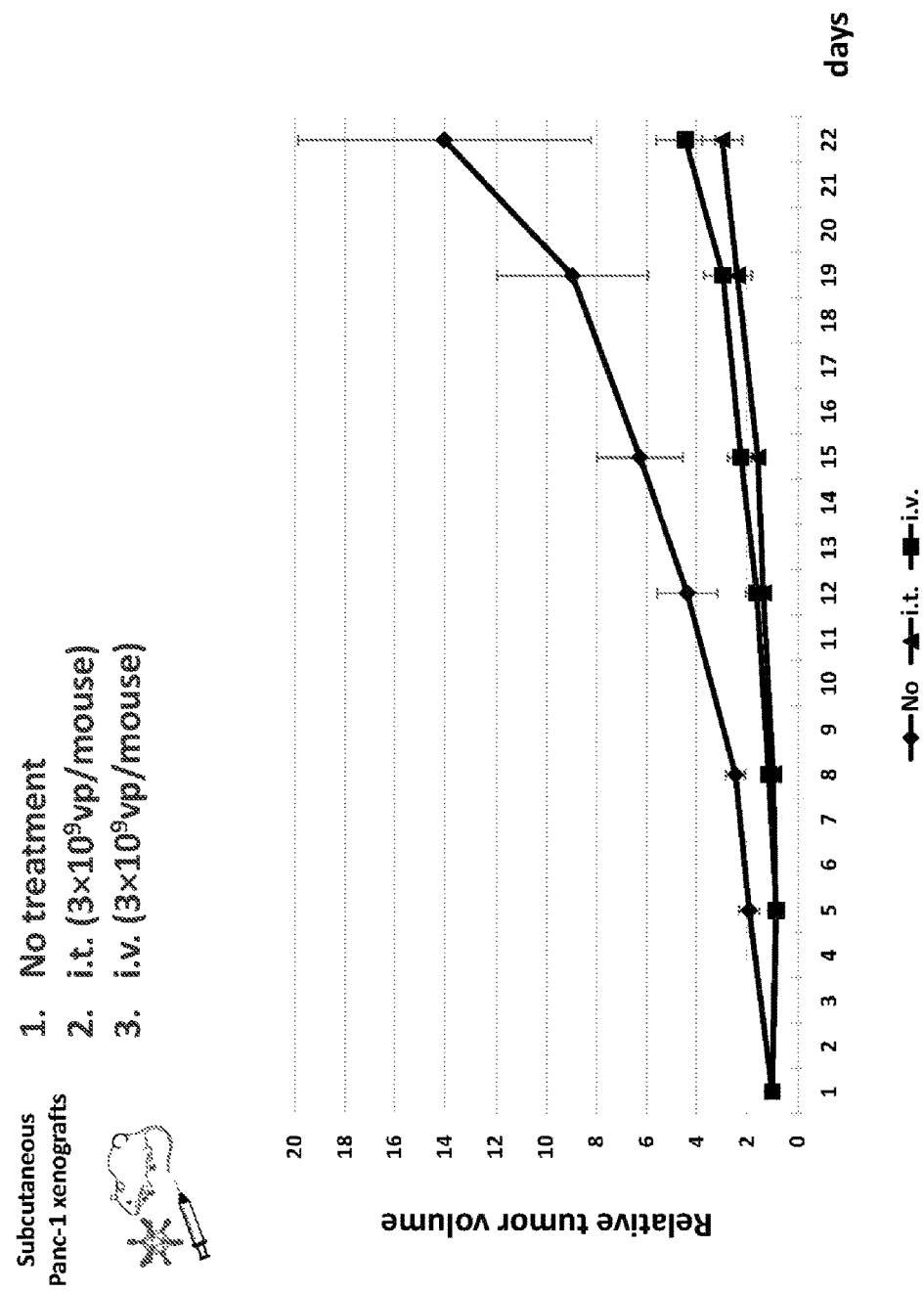

FIG. 31. Treatment Effect of AdML-VTIN for Panc-1 Xenograft (i.t. vs i.v.) (Medium Dose: $3.0\times10^9$ vp). In order to see the dose dependence of the therapeutic effect of infectivity-selective oncolytic adenovirus (ISOAd), 3 times higher dose of AdML-VTIN than administered in FIG. 30 ($3.0\times10^9$ vp/mouse) was injected intratumorally and intravenously into mice bearing MSLN-positive Panc-1 tumors. Both i.t. and i.v injected viruses showed stronger anti-tumor effect compared to the low dose injection in FIG. 30, and the difference in tumor volume observed between i.t. and i.v. was less. These data indicate the dose dependent effect of ISOAd.

Figure 32:
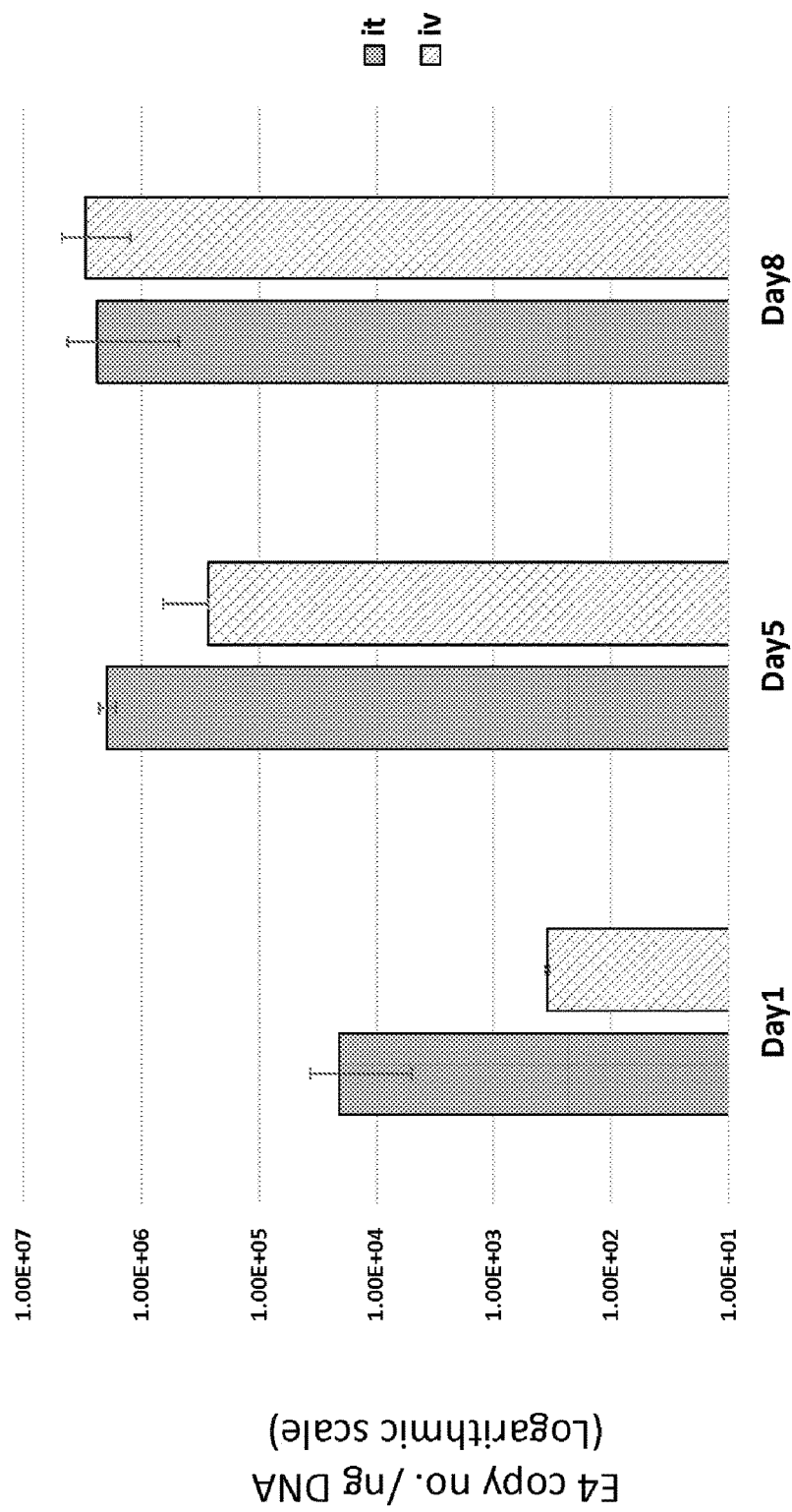

FIG. 32. Virus Copy Number after injection to Panc-1 Xenograft (i.t. vs i.v.) (Medium Dose: $3.0\times10^9$ vp). One, five, and eight days after intratumoral or intravenous injection of mesothelin targeted ISOAd into mice bearing MSLN-positive Panc-1 tumors, the mice were sacrificed and the virus copy number in the tumor was determined by qPCR for E4 regions. At day 1, the virus dose after i.v. injection was more than 1.5 orders lower than that after i.t. injection. However, the viral copy number after i.v. injection increased with time and eventually equaled that seen in i.t. injection (Day 8). These data support the similar therapeutic effects of i.t. and i.v. shown in FIG. 30 and FIG. 31.

Figure 33:
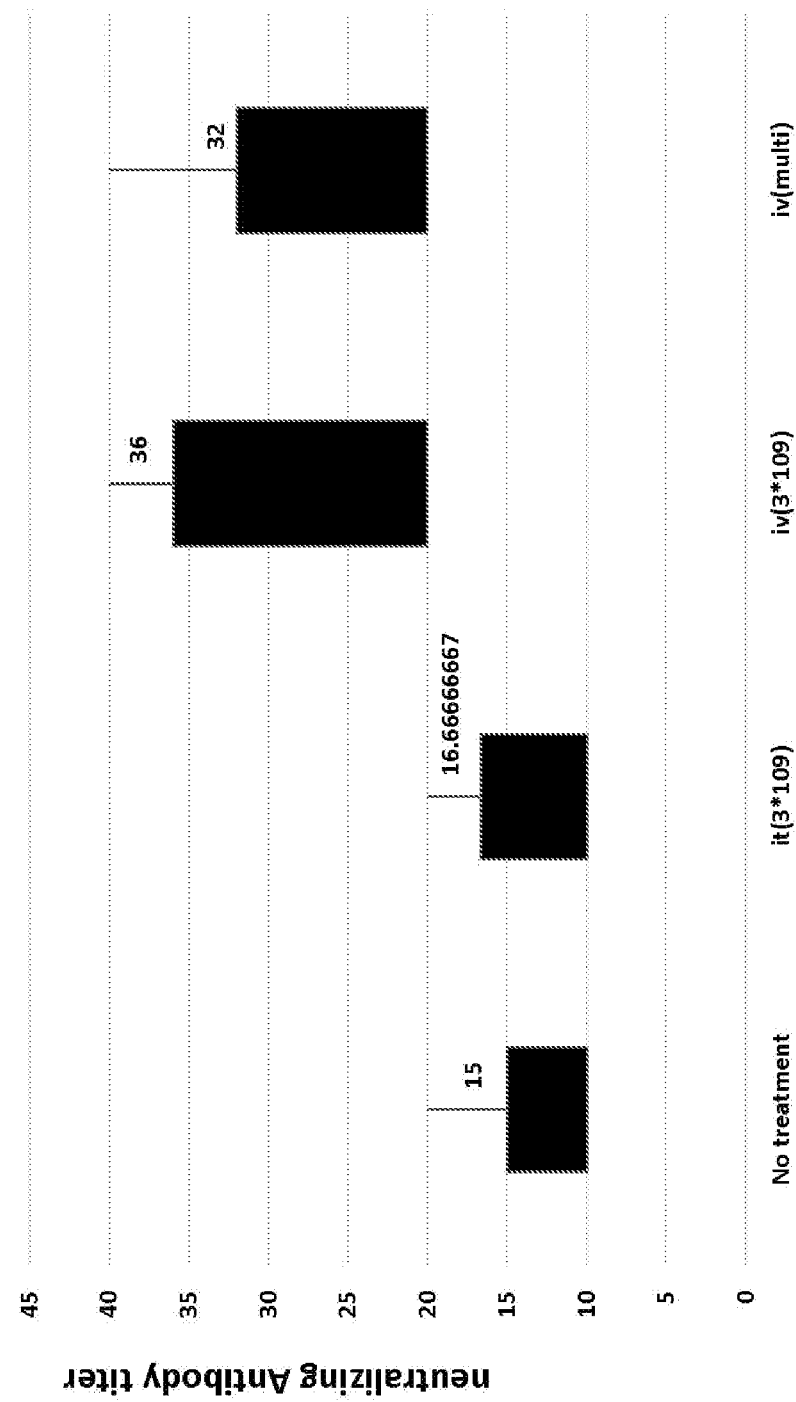

FIG. 33. Neutralizing antibody in AdML-VTIN-treated nude mice. Nude mice are known to produce IgM antibody. The neutralizing Ab titer (the last dilution showing ≥50% infection inhibition) was measured after viral injections. After injection of AdML-VTIN intravenously ($3.0\times10^9$ vp/mouse), the neutralizing Ab titer increased. The level of increase in Ab titer was the same between single injection and multiple injections ($3.0\times10^9$ vp, 4 times). Intratumoral injection did not increase the titer of neutralizing antibodies.

Figure 34:
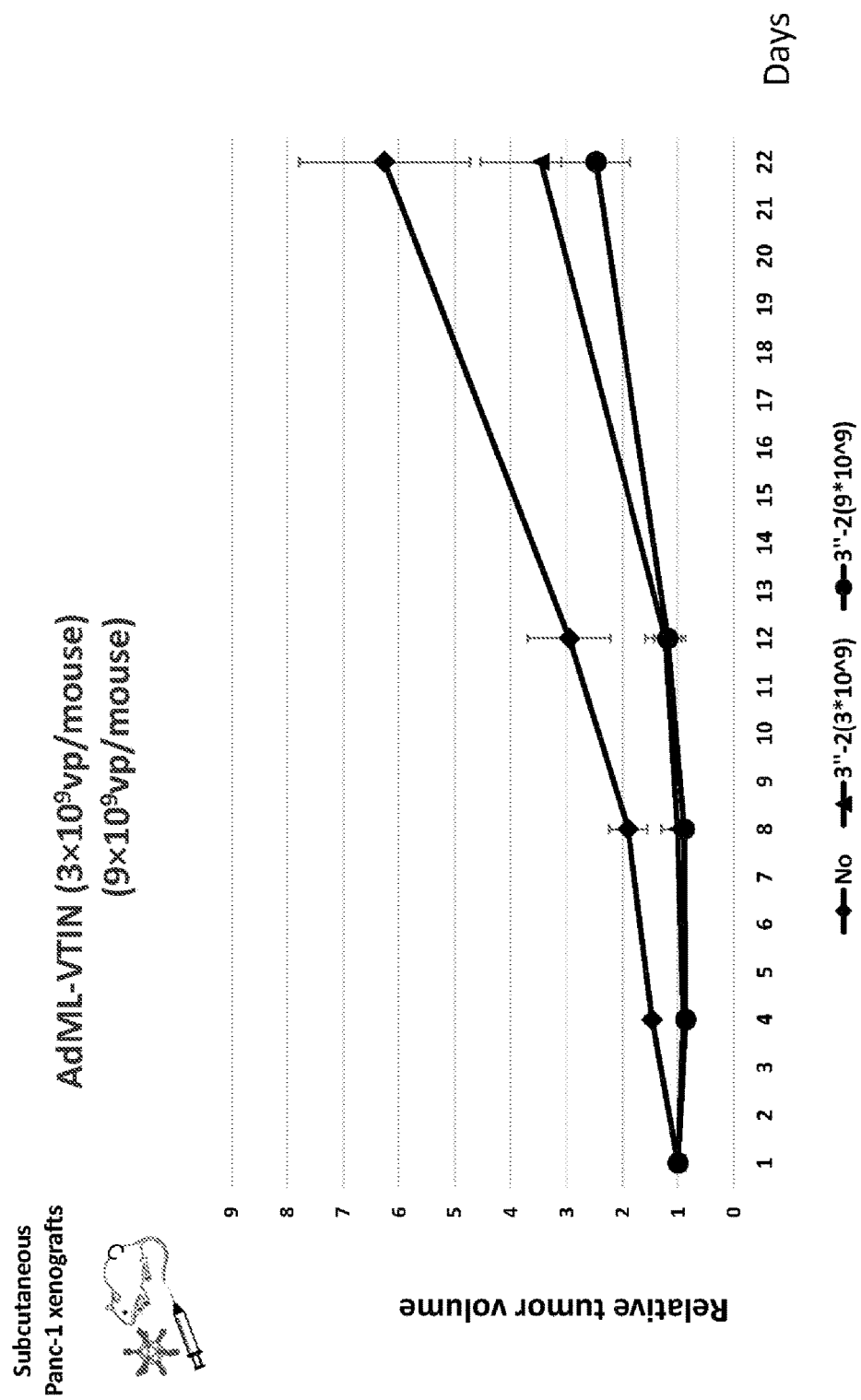

FIG. 34. Treatment Effect of High Dose AdML-VTIN for Panc-1 Xenograft. Higher dose ($9.0\times10^9$ vp/mouse) AdML-VTIN administered i.v. demonstrates further improvement of therapeutic effect. AdML-VTIN ($3.0\times10^9$ vp/mouse or $9.0\times10^9$ vp/mouse) was injected intratumorally and intravenously into mice bearing MSLN-positive Panc-1 tumors, and tumor size was followed. $9.0\times10^9$ vp/mouse AdML-VTIN improved the inhibition of tumor growth but the increase was not significant compared to the inhibition observed with $3.0\times10^9$ vp/mouse AdML-VTIN. The increased effect of high dose AdML-VTIN was significant compared to low dose AdML-VTIN ($1.0\times10^9$ vp), shown in FIG. 30.

Figure 35:
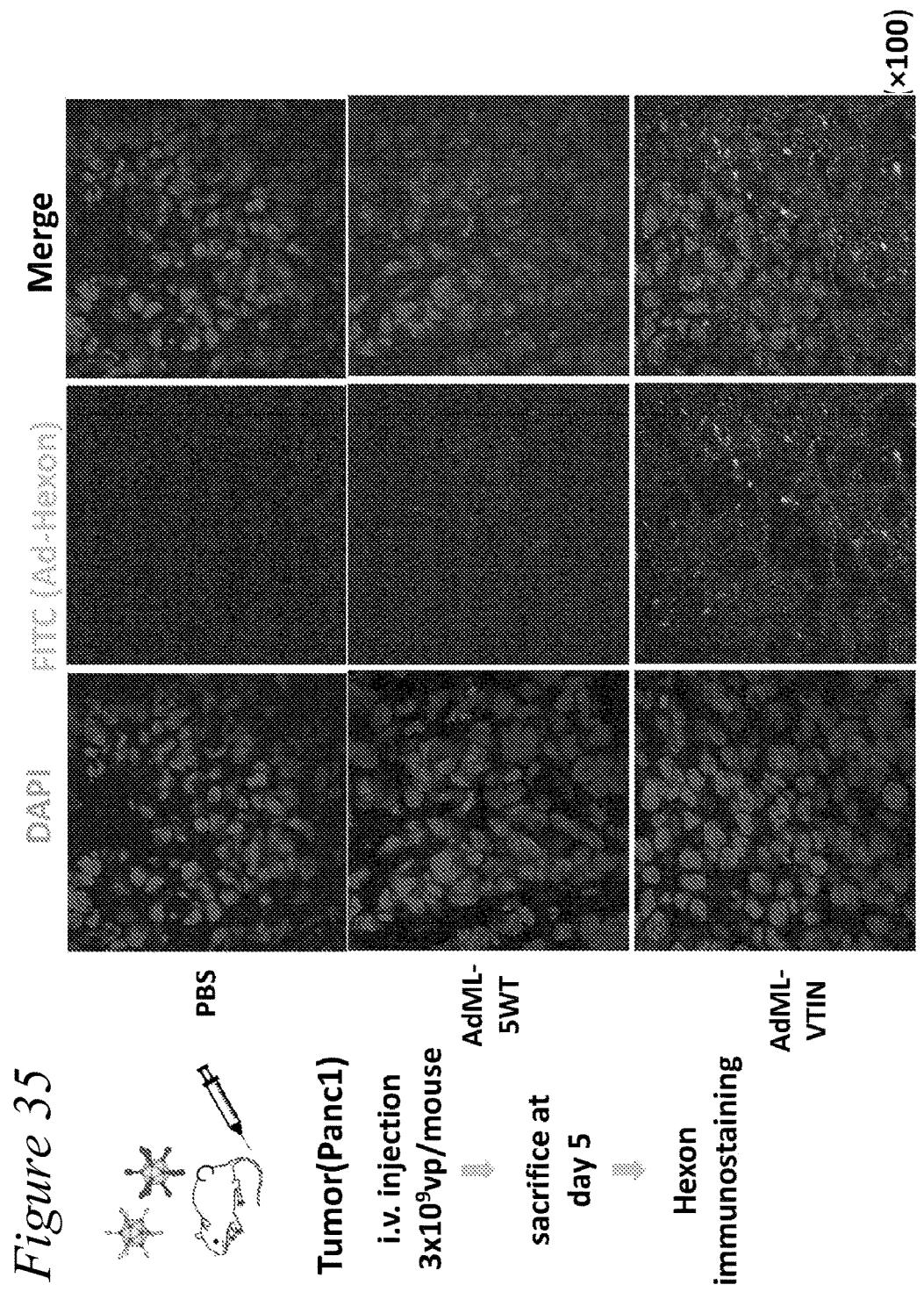

FIG. 35. Hexon immunostaining after i.v. (Day 5). Five days after i.v. injection of AdML-VTIN ($3.0\times10^9$ vp/mouse) into Panc-1 tumor-bearing mice, the tumors were harvested and stained for adenoviral late protein (hexon) in order to assess the existence and replication of the viruses. (Hexon protein is expressed only when the virus is replicating.) AdML-VTIN shows significant hexon expression in the tumor, while the expression with AdML-5WT is very limited. This expression profile indicates that intravenously injected VTIN-equipped virus goes to the target tumor and replicates, an effect that cannot be achieved by non-targeted wild type virus.

Figure 36:
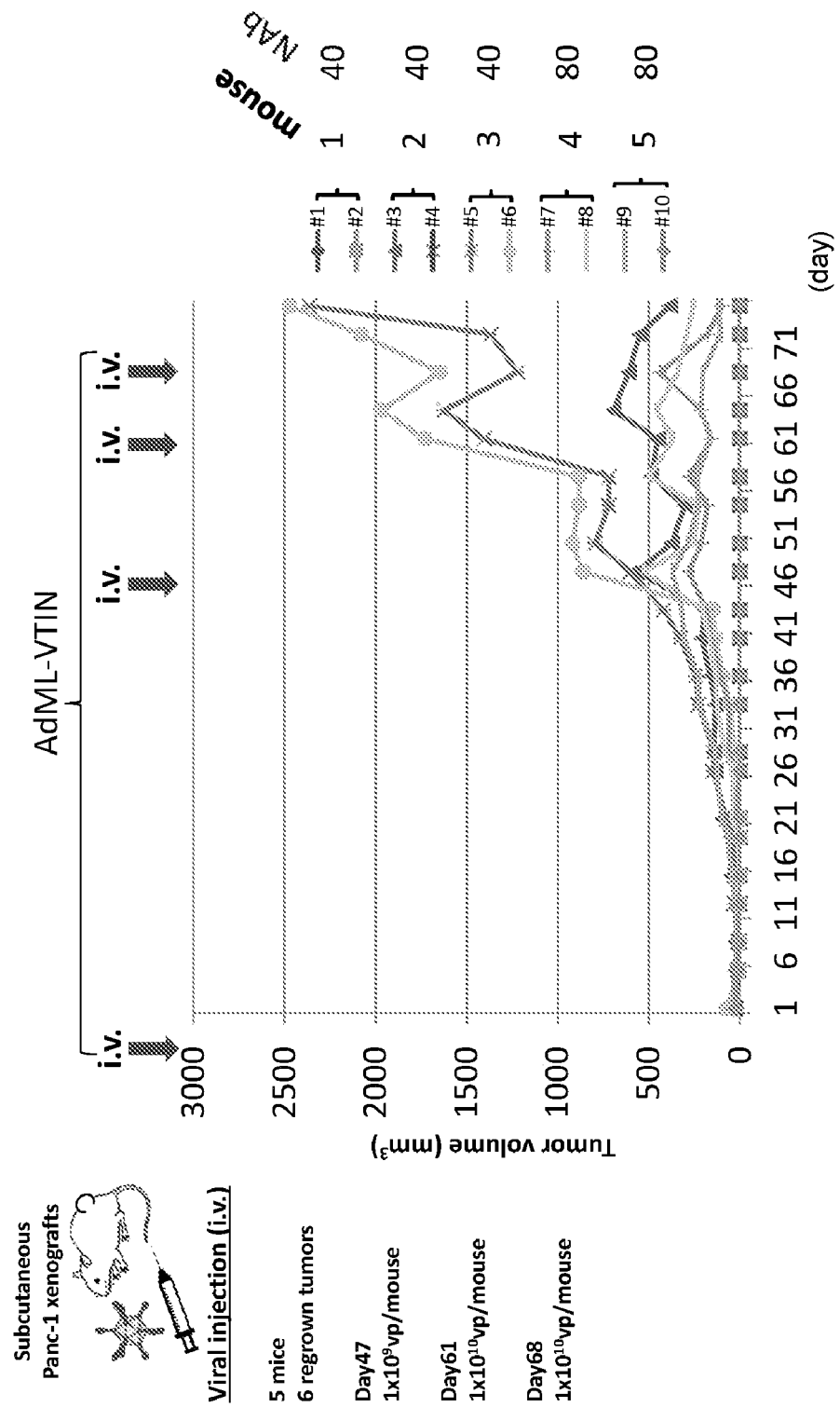

FIG. 36. The Effect of Multiple of Systemic Treatment with AdML-VTIN for Relapsing Panc-1 Tumors. The mice injected with AdML-VTIN, as described in FIG. 29, were further followed, and the tumor volume of each individual tumor was measured over time. Four out of ten tumors that showed complete remission after one injection. The remaining 6 tumors that showed regrowth around day 30. All mice received additional i.v. of infectivity-selective oncolytic adenovirus (AdML-VTIN) injection at days 47, 61, and 68. Four out of six tumors showed good tumor control by re-treatment with AdML-VTIN even though the tumor size at the time of re-treatment was relatively large. Two out of the six tumors showed a temporary response soon after re-treatment and then regrowth. Very interestingly, the efficacy of re-treatment did not correlate with neutralizing Ab (NAb) titers.

Figure 37A:
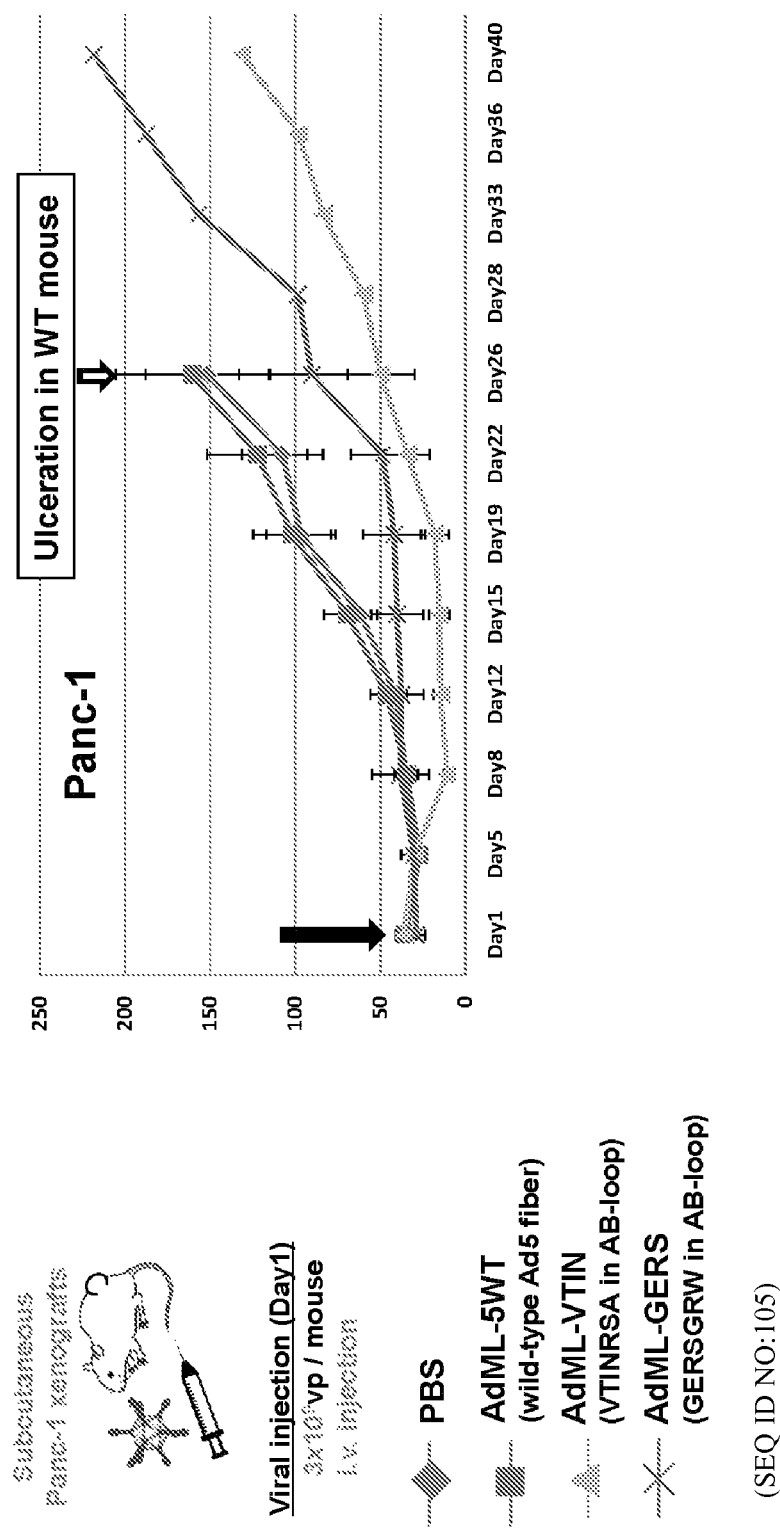
Figure 37B:
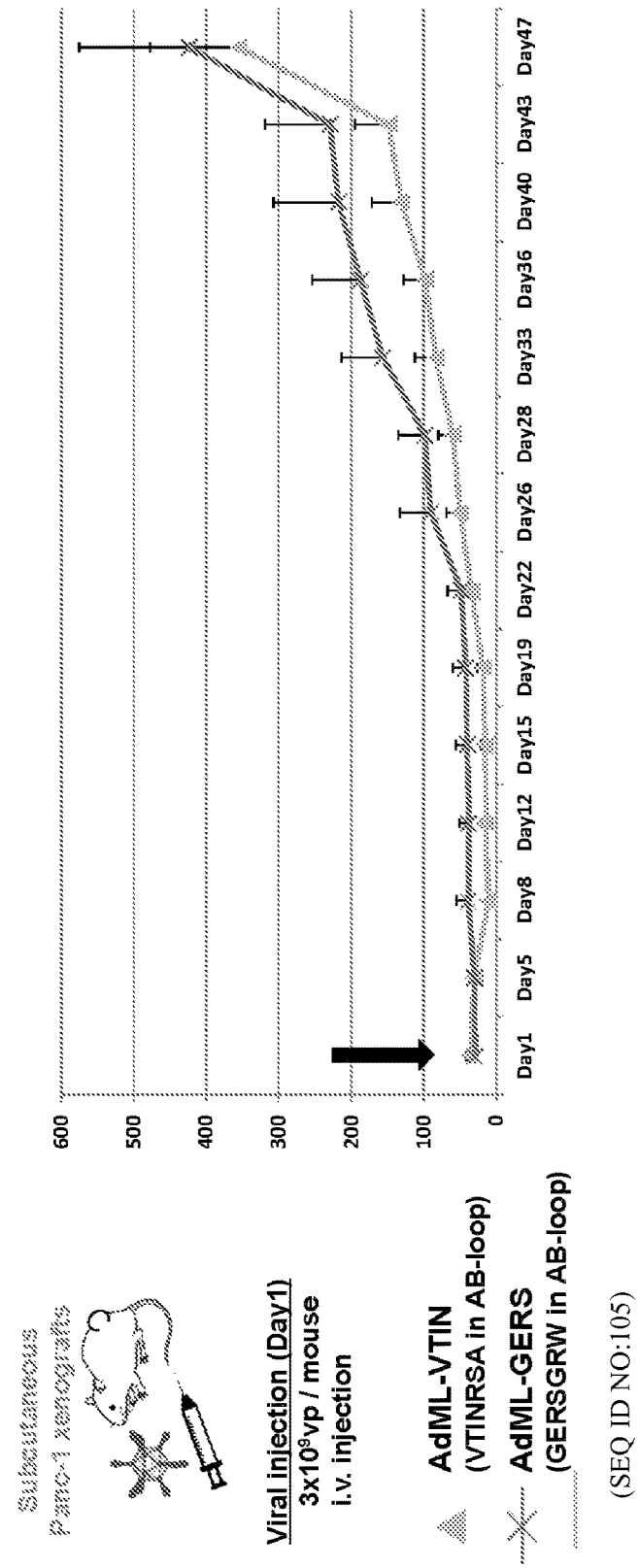

FIG. 37. Comparison of Differently Targeted Oncolytic Ad in Systemic Treatment of Panc1 Tumors (high dose). In order to prove the in vivo specificity of differently targeted oncolytic adenoviruses, we compared vectors with different targeting motifs in mesothelin-positive pancreatic cancer cell line xenografts in nude mice. Viruses ($3.0\times10^9$ vp) or PBS were injected intravenously, and the tumor size was followed. Mesothelin-targeted AdML-VTIN showed tumor suppression relative to AdML-5WT or PBS control as early as day 8. Prostate cancer-targeted AdML-GERS showed similar antitumor effect as untreated and non-targeted virus through day 15. The non-targeted virus did not show any therapeutic effect after i.v. injection. (a) 4 group comparison. (b) Longer follow up of AdML-VTIN and AdML-GERS. The therapeutic effect of these vectors correlated with viral binding affinity, as shown in FIG. 26.

Figure 38:
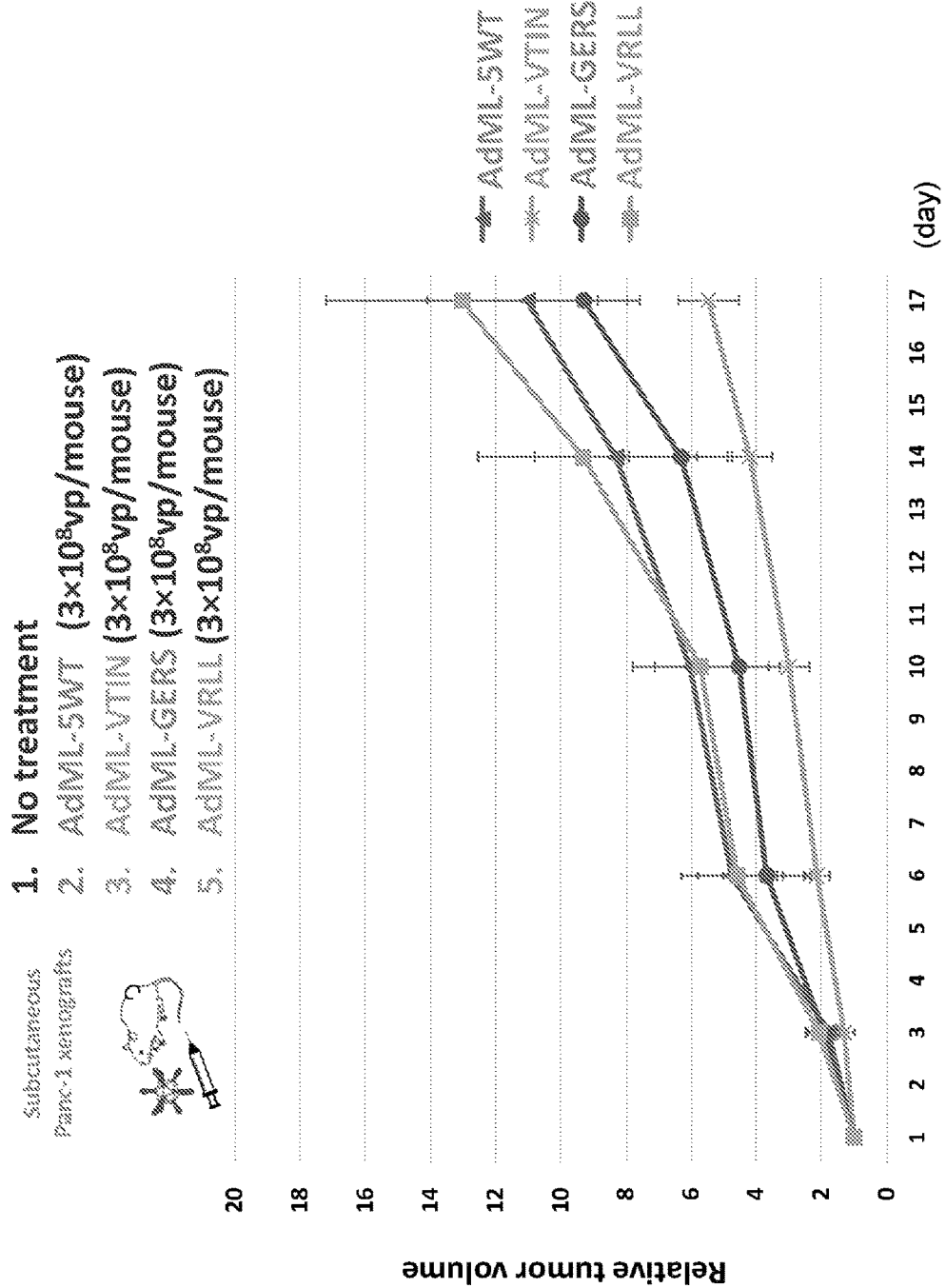

FIG. 38. Comparison of Differently Targeted Oncolytic Ad in Systemic Treatment of Panc1 Tumors (very low dose). The therapeutic effect of very low dose of targeted of infectivity-selective oncolytic adenovirus (ISOAd) was compared in the same model used in FIG. 37. No virus or 1/10 of the viral dose administered in FIG. 37 ($3.0\times10^8$ vp) was injected intravenously, and tumor size was followed. Mesothelin-targeted AdML-VTIN showed the strongest tumor suppression. Prostate cancer-targeted AdML-GERS showed some antitumor effect, but another prostate cancer-targeted virus (AdML-VRLL) and non-targeted virus (AdML-5WT) did not show therapeutic effect. The therapeutic effect of these vectors correlated with viral binding affinity shown in FIG. 26.

Figure 39A:
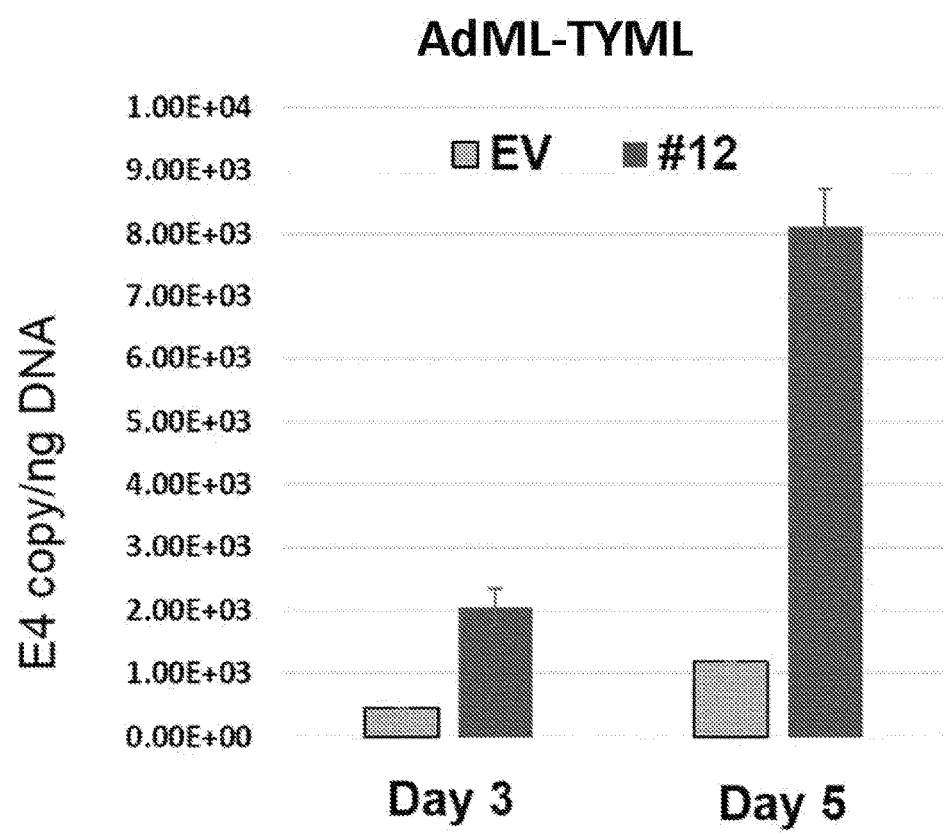
Figure 39B:
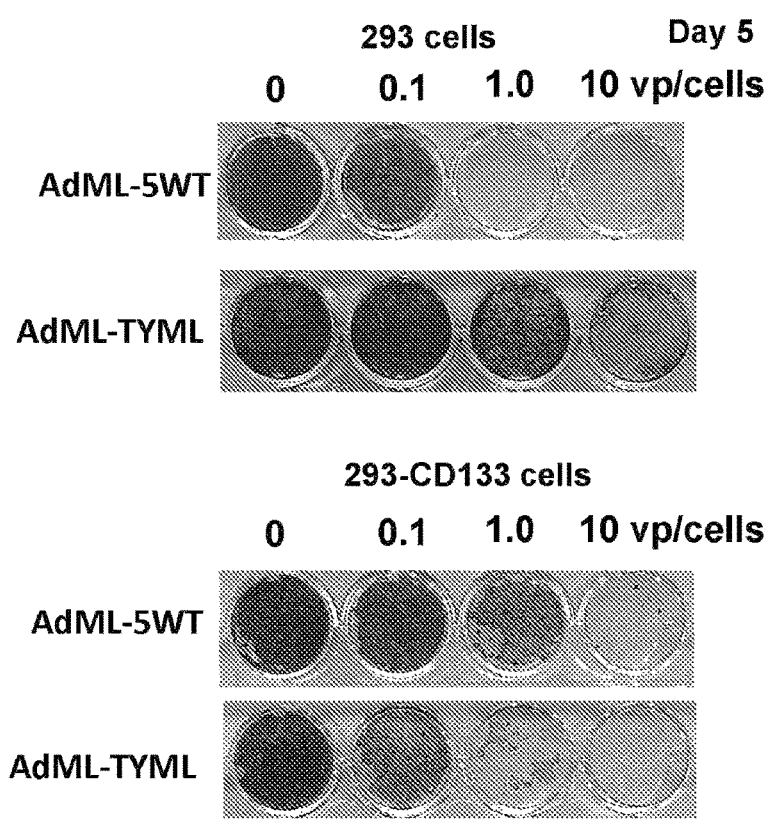

FIG. 39. Analysis of Viral Replication and Cytocidal Effect if CD133 Targeted Virus. (a) Isolated virus (AdML-TYML) replicates in CD133-expressing 293 cells (clone #12), but not in empty vector transfected 293 cells (EV), as measured at day 3 and at day 5 by qPCR for E4 region. (b) In 293 cells, the ED50 of AdML-TYML is more than one order higher than that of AdML-5WT. In contrast, the ED50 of AdML-TYML in CD133-expressing 293 cells is more than one order lower than that of AdML-WT. These data indicate the selectivity of AdL-TYML depends on CD133 expression.

Figure 40:
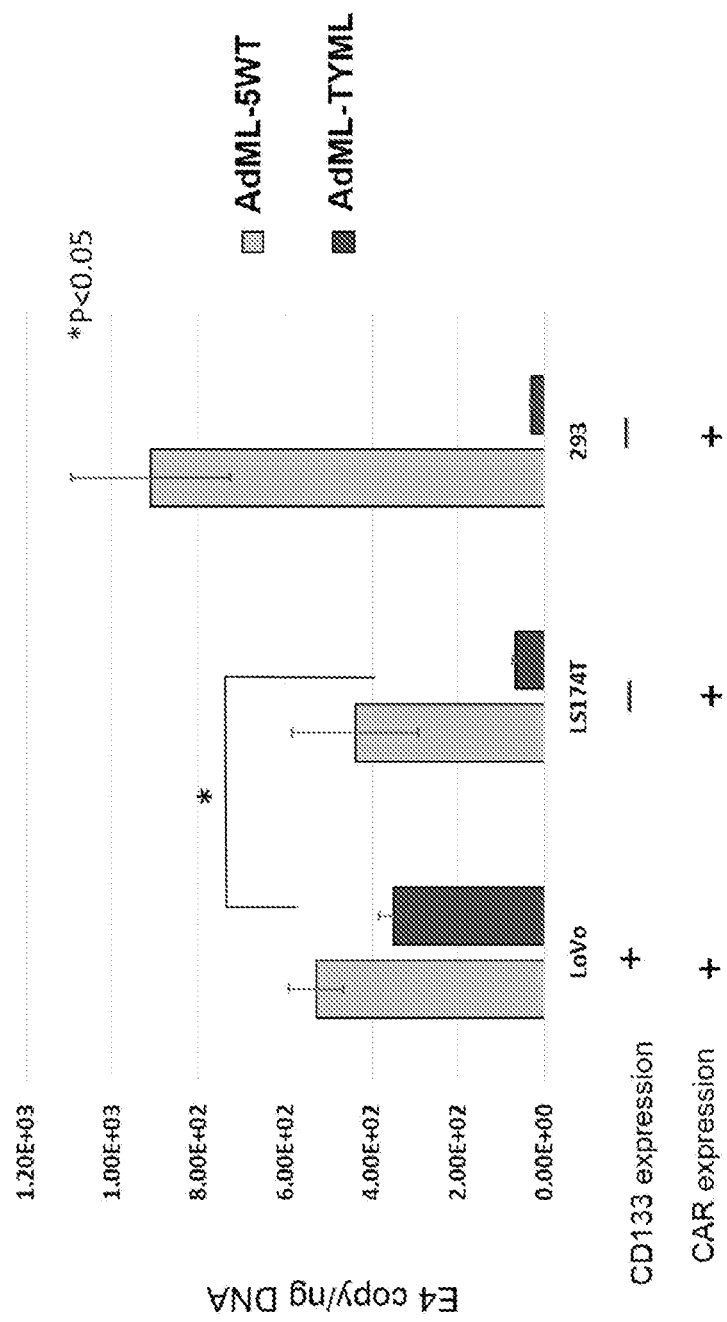

FIG. 40. Binding Ability of AdML-TYML in Colon Cancer Cell Lines. Virus binding to colon cancer cells expressing different levels of CD133 was compared between CD133-targeted AdML-TYML and non-targeted AdML-5WT by performing E4 qPCR. AdML-TYML showed strong binding to CD133-expressing LoVo, but not to low expressors of CD133 (LS174T and 293). On the other hand, AdML-5WT showed strong binding to all three cell types because each cell type highly expresses the Ad5 receptor CAR.

Figure 41:
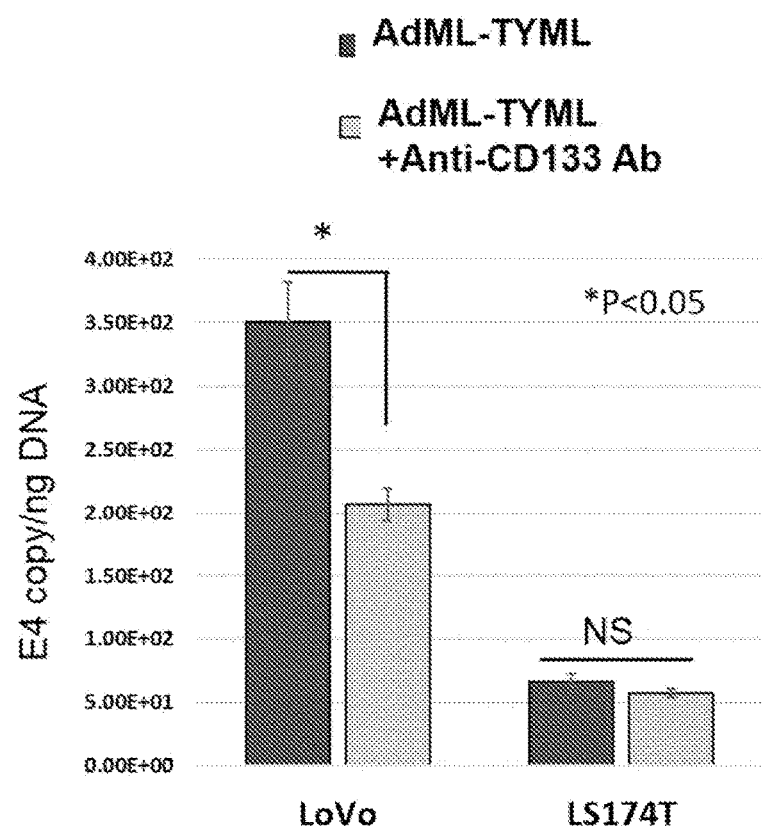

FIG. 41. Anti-CD133 Ab Inhibits the Binding of AdML-TYML to CD133-positive Colon Cancer Cell Lines. Pre-treatment with anti-CD133 Ab inhibits the binding of CD133 targeted AdML-TYML to CD133-positive cancer cells (LoVo), as measured by E4 qPCR. AdML-TYML binding to CD133-negative LS174T cells was lower and was not inhibited by anti-CD133 Ab. These data indicate that the binding of AdML-TYML is mediated specifically via binding to CD133.

Figure 42A:
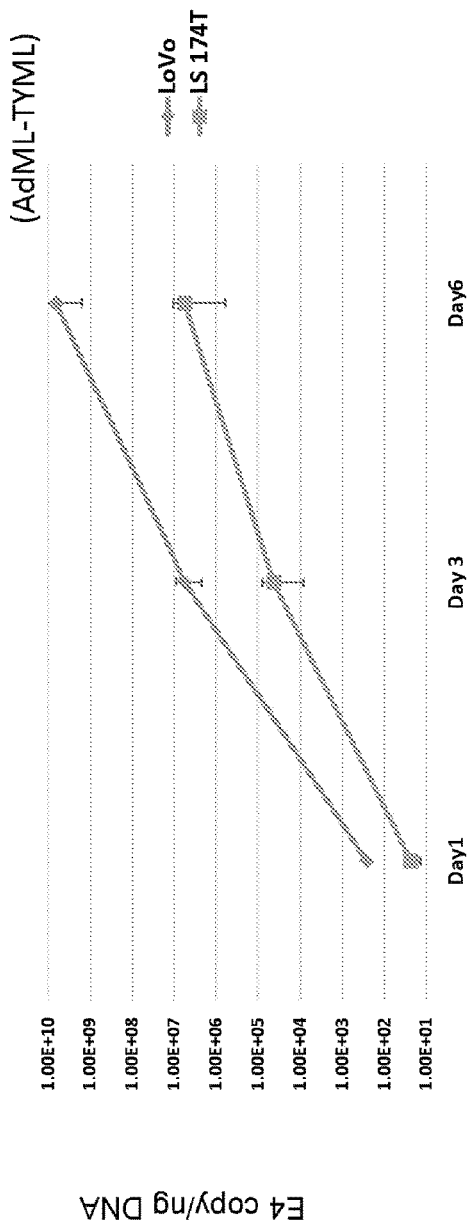
Figure 42B:
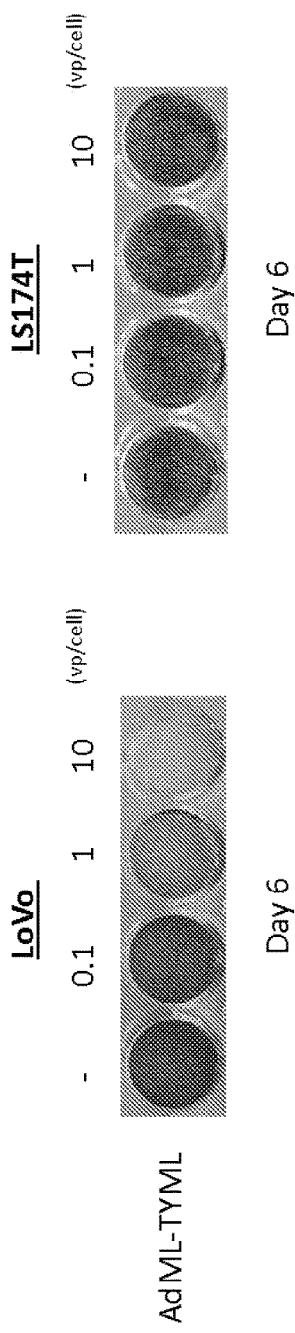

FIG. 42. Analysis of Viral Replication and Cytocidal effect on Colon Cancer Cell Lines. (a) After infection, the copy number of Ad-TYML on LoVo (CD133(+)) was one order higher than that in LS174T (CD133(−)) at day one, as measured by E4 qPCR. The difference between the vectors increased and reached three orders at day 6. Y axis is logarithmic scale. (b) AdML-TYML showed more than 50% lethality at 1 vp/cell in LoVo cell at day 6, while it did not show cytotoxicity in LS 174T cells even at 10 vp/cell. These data show selective replication and cytotoxicity of CD133-targeted oncolytic adenovirus (OAd) in CD133-positive cells.

Figure 43:
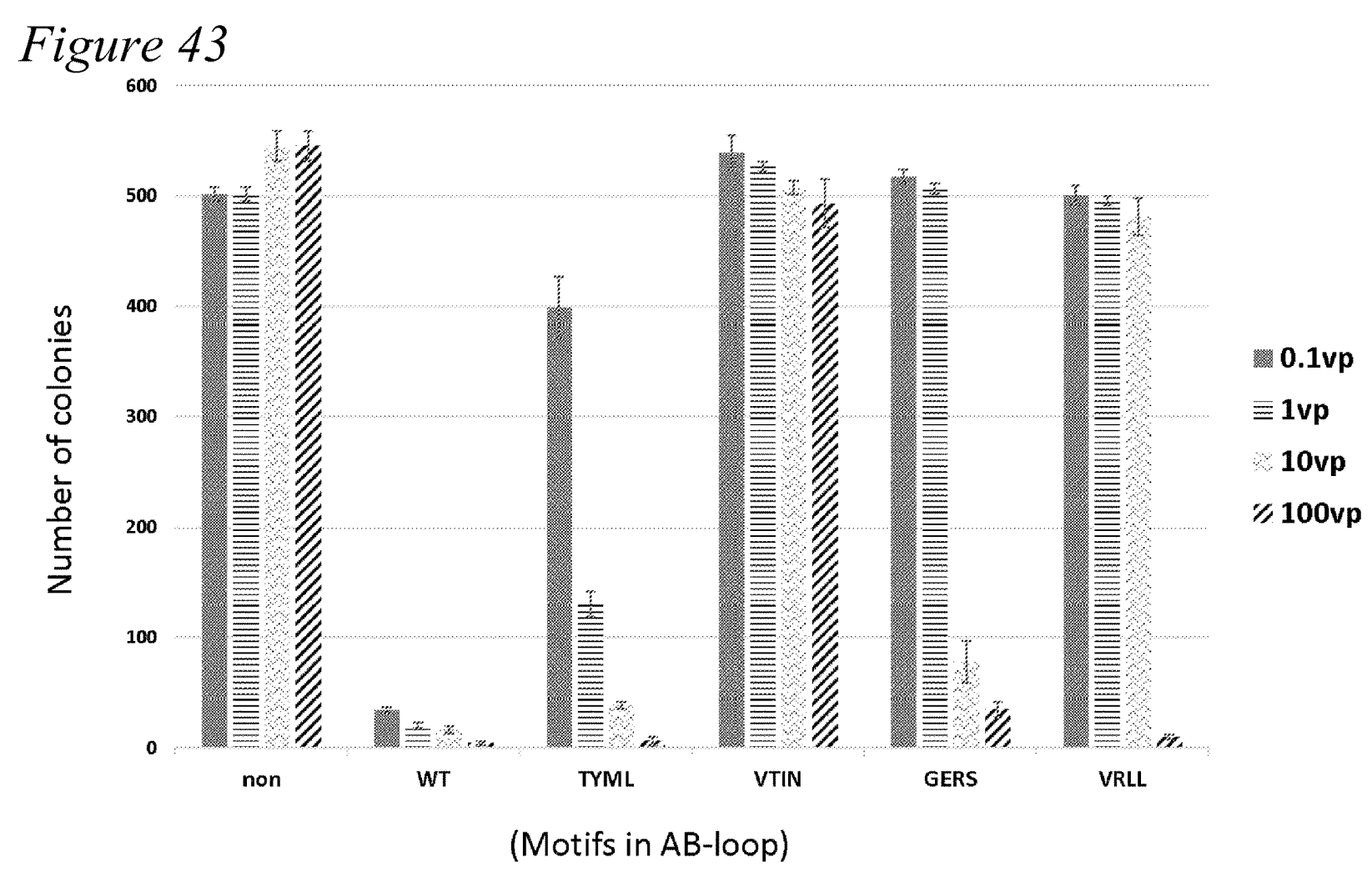

FIG. 43. In Vitro Anti-Tumor Effect Evaluation by Colony Formation Assay. The effect of targeted-oncolytic adenoviruses was assessed by Colony Formation Assay. CD133-positive LoVo cells were infected with various titers (0.1-10 vp/cell) of wild type and the infectivity-selective oncolytic adenovirus (ISOAd) (AdML-WT, AdML-TYML, AdML-VTIN, AdML-GERS, and AdML-VRLL) and 2 days later, the cells were plated at 500 cells per plate. Colonies were counted after 7 more days. The results indicate that AdML-TYML showed dose-dependent inhibition of colony formation. AdML-GERS shows some binding to LoVo cells at 10 vp/cell or higher. The effect of mesothelon-targeted VTIN and PC-3-targeted VRLL was minimal. AdML-5WT shows significant antitumor effect, but this vector itself is not currently usable in the clinic because of lack of specificity. In this sense, TYML vector is apparently the most promising vector for CD133-positive colorectal cancer cells.

Figure 44A:
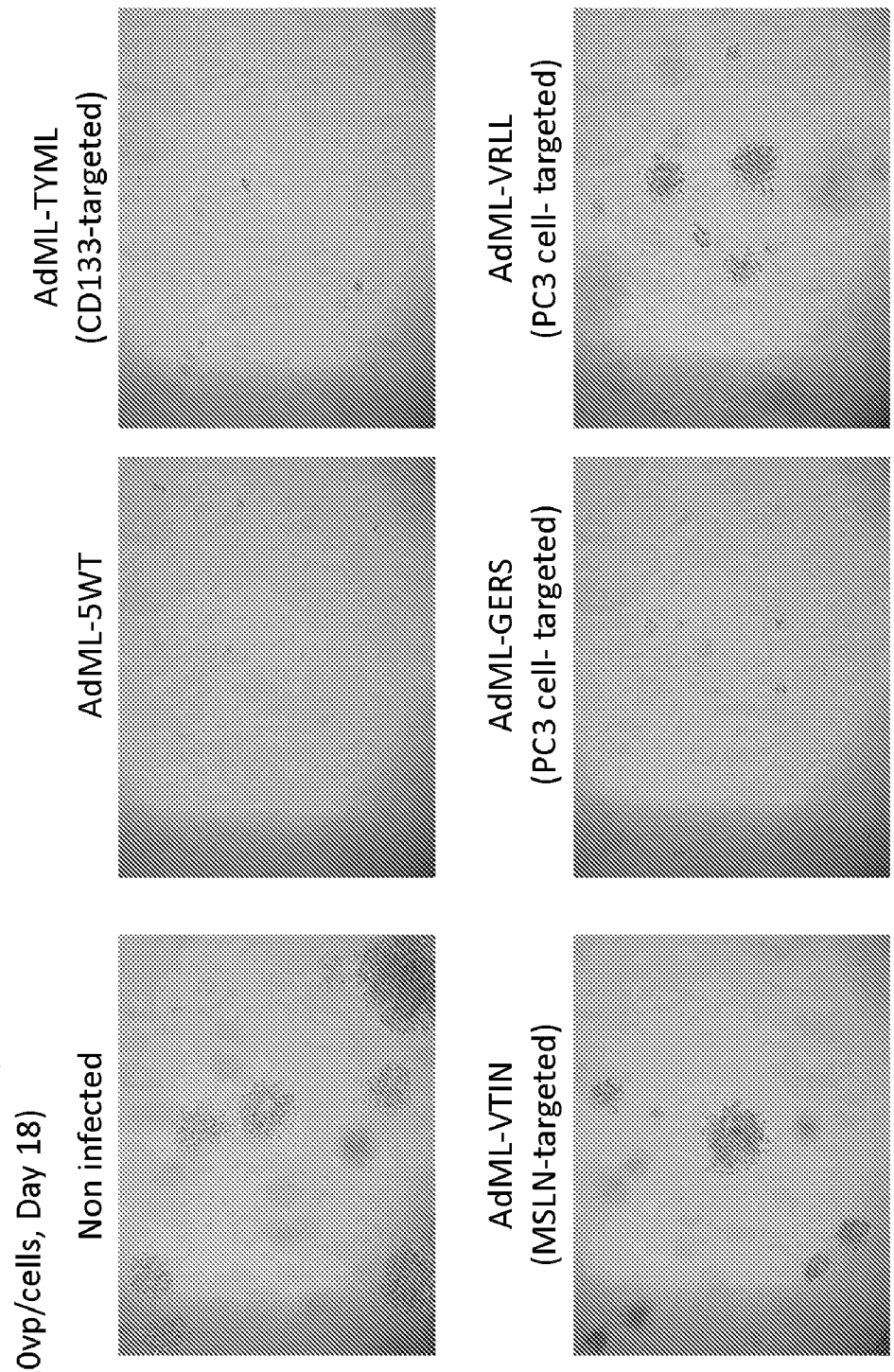
Figure 44B:
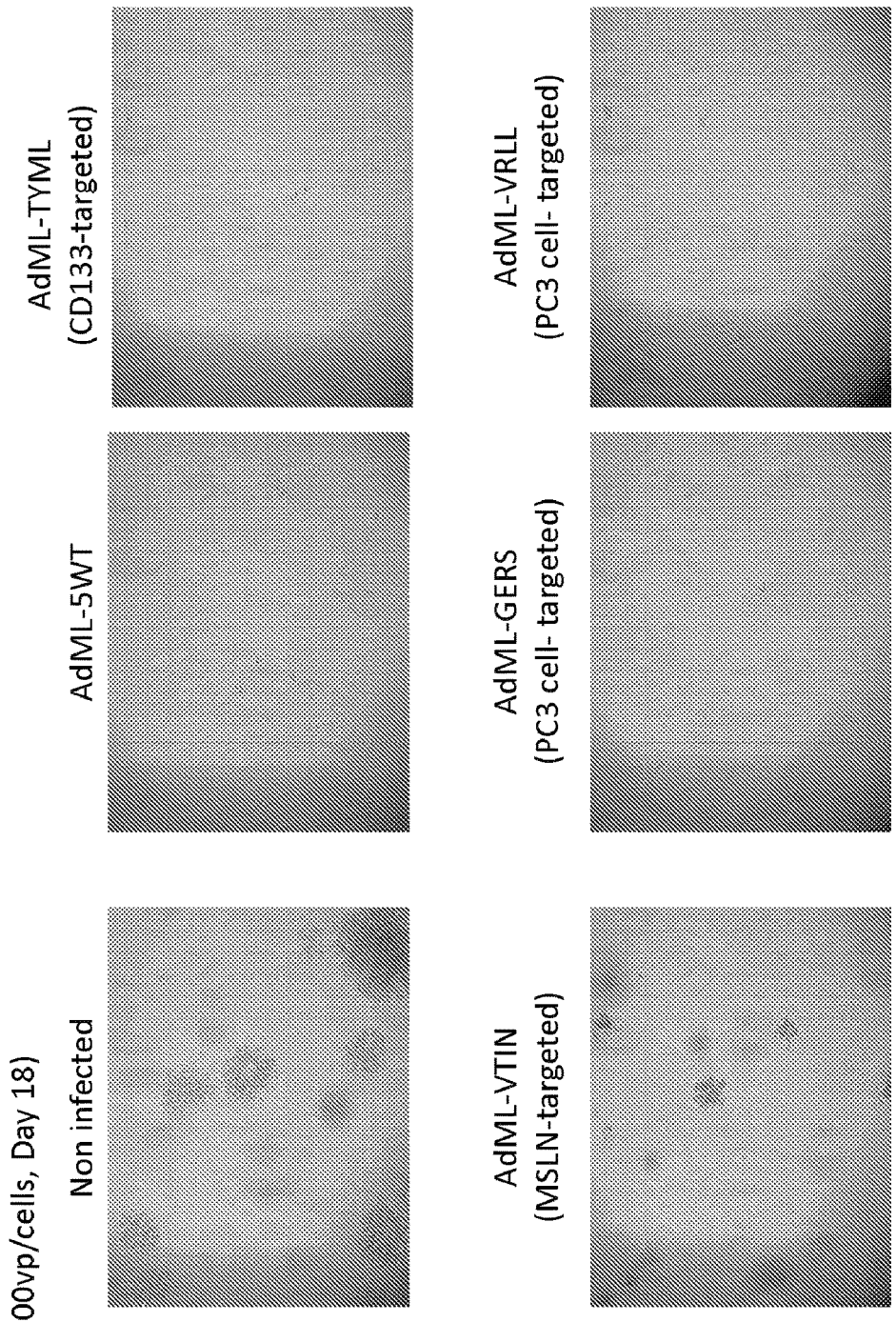

FIG. 44. In Vitro Anti-Cancer Stem Cell Effect Evaluated by Sphere Formation Assay. Anti-cancer stem cell effect was evaluated by Sphere Formation Assay. These results show that the infectivity-selective oncolytic adenovirus (ISOAd) equipped with anti-CD133 motif (TYML) has anti-cancer stem cell effect in CD133-positive colorectal cancer cell line, LoVo. (a) 10 vp/cell infection, Day 18, (b) 100 vp/cell infection, Day 18.

FIG. 45. In Vivo Anti-Cancer-Stem-Cell Assay by Tumor Formation Assay in Nude Mice. Two hours after infection with AdML-TYML virus, cells were trypsinized and counted, then inoculated ($10^4$ and $10^5$ per injection) into nude mice to assess tumorigenesis. AdML-TYML inhibited tumorigenesis of CD133 positive LoVo cells after both $10^4$ and $10^5$ cells/site injections. In contrast, the anti-tumorigenesis effect was minimal in CD133-negative LC174T cells. These data indicate that of infectivity-selective oncolytic adenovirus (ISOAd) with TYML motif demonstrates an anti-CSC effect in vivo only in CD133-positive cells.

Figure 46:
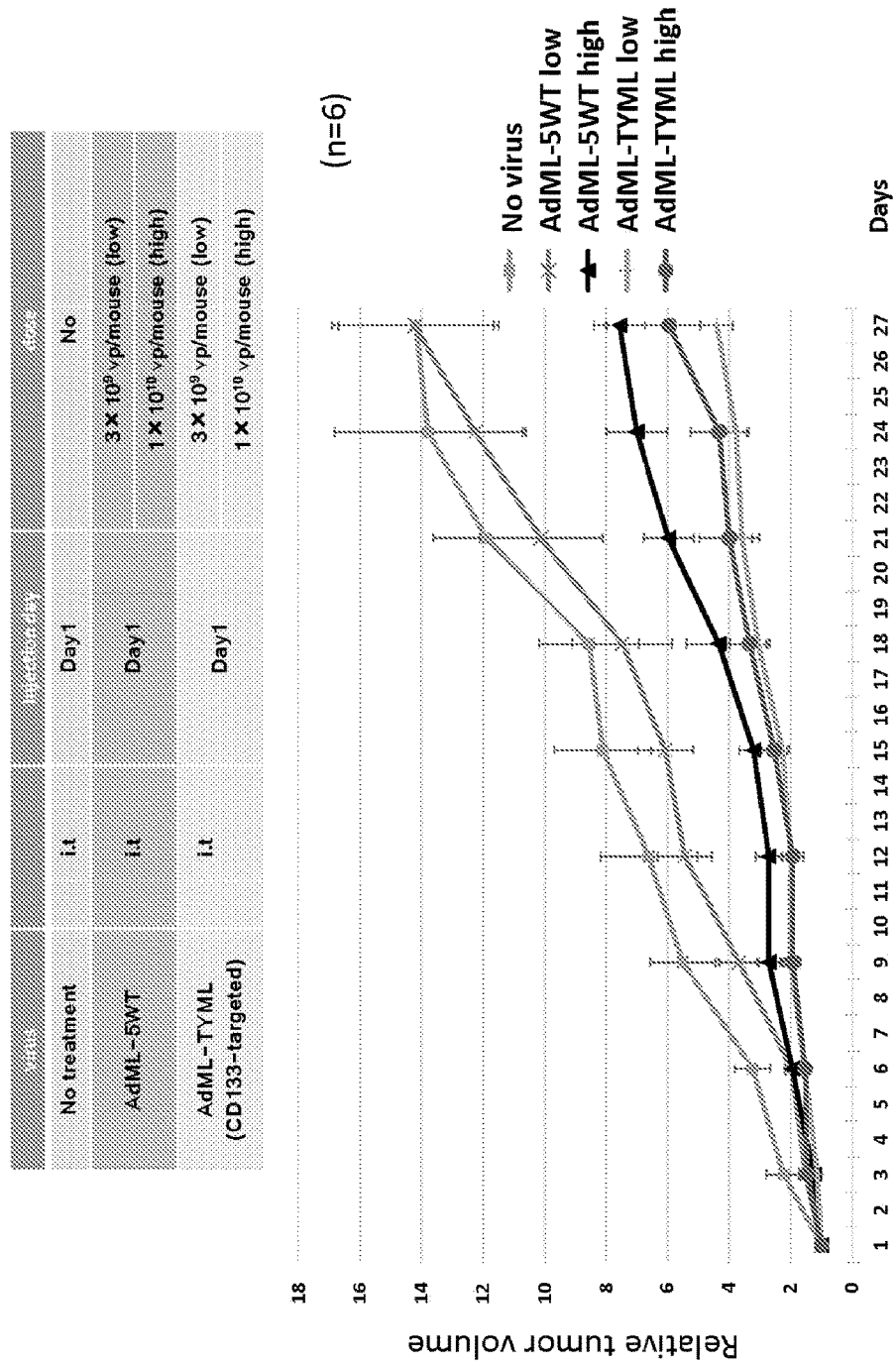

FIG. 46. Anti-tumor Effect of AdML-TYML Virus in LoVo Cells after Intratumoral Injection. The anti-tumor effect of CD133-targeted oncolytic adenovirus was tested in CD133-positive LoVo cell subcutaneous xenografts in nude mice. Virus was administered as described in the upper panel, and tumor size was followed. As shown in the lower panel, AdML-TYML exhibited strong anti-tumor effect on established tumors at both doses tested ($3.0 \times 10^9$ vp and $1.0 \times 10^{10}$ vp). On the contrary, AdML-5WT showed weak anti-tumor effect at high doses ($3.0 \times 10^9$ vp), but low doses ($1.0 \times 10^{10}$ vp) did not show significant anti-tumor effect. These data indicate the anti-tumor efficacy of CD133-targeted oncolytic adenovirus in established tumors. Relative tumor volume was calculated by using the volume immediately before injection (day 0) as the reference volume. The tumor volume was calculated as width×length/2. (Left panel: the plot of absolute volume. Right panel: the plot of relative volume.)

Figure 47:
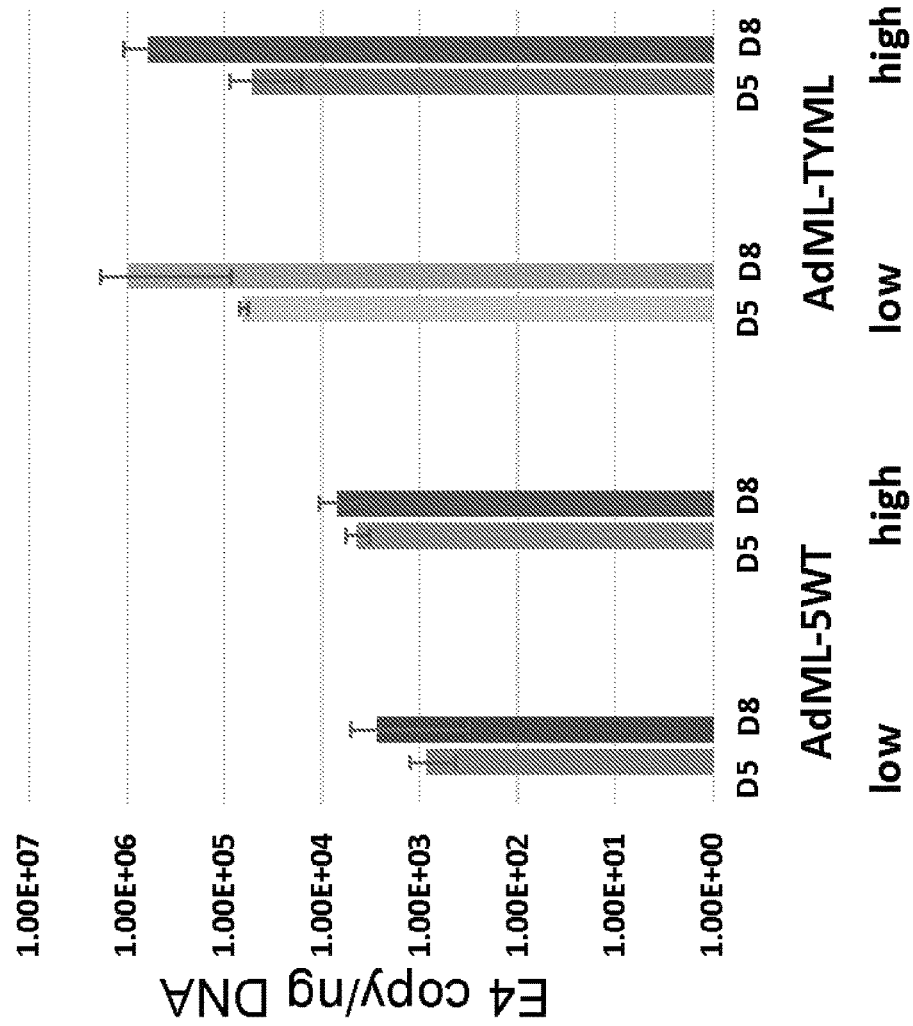

FIG. 47. Replication of AdML-TYML Virus in LoVo Cells after Intratumoral Injection. Mice were injected as described for FIG. 46, then the tumors were recovered at day 5 and day 8 to determine the viral copy number in the tumor. The AdML-TYML targeted to CD133 showed higher copy number in the tumor compared to AdML-5WT at day 5 and day 8. The copy number of AdML-TYML was similar between the two dose cohorts. The copy number after treatment with AdML-5WT was significantly lower than after treatment with AdML-TYML and showed some increase along with dose escalation. The virus copy number/replication level correlated well with the anti-tumor effect observed in FIG. 46. These data indicate the superiority of the CD133-targeted oncolytic adenovirus (OAd) for the treatment of CD133-positive colorectal cancer in vivo.

DETAILED DESCRIPTION OF ILLUSTRATIVE EMBODIMENTS

This disclosure describes adenovirus libraries and a method for producing such adenovirus libraries. The methods can exploit recombination between a rescue adenovirus and one of a plurality of shuttle polynucleotides in the host cell. The methods also can involve infecting host cells with adenovirus at a relatively low multiplicity of infection and subsequently collecting crude viral lysate and re-infecting the host cells with adenovirus in the crude viral lysate.

This disclosure further describes methods of selecting and using adenoviruses from adenovirus libraries for one or more qualities including, for example, binding to a target molecule or cell; selective replication in a particular cell type, including, for example, a tumor cell; and/or selective distribution in vivo at the tissue level, including for example, selective distribution to specific organs or selective distribution outside of specific organs.

As used herein:

"Selective" and variations thereof refer to being able to differentiate, to any degree, between two or more alternatives such as, for example, cell populations; and "Host" refers to a cell or animal in which a vector, such as a virus, or a cell, such as a tumor cell, can grow. In some embodiments, a host cell is a eukaryotic cell line that can be infected with a virus. In some embodiments, a host animal is either a rat or a mouse, such as an athymic nude mouse, hamster, or rat or a SCID (Severe Combined Immunodeficient) mouse. In some embodiments, the host animal is syngeneic with a tumor cell or is immune deficient.

Adenoviruses (Ad) can have high in vitro and in vivo transduction efficiency compared to other viral and non-viral gene transfer methods. Thus, it may be attractive to consider using an adenovirus in the construction of genetic libraries. However, such developments have been hampered by extremely low conversion from virus-coding plasmids to viruses. For example, in a conventional adenovirus vector generation method, 1 µg of plasmid ($3 \times 10^{10}$ copy) generates only 1-2 plaques of virus, resulting in a viral library yield of only $1/10^{10}$ of the diversity of the plasmid before transfection.

The methods described herein can significantly improve plasmid-to-virus conversion. Thus, such a system can allow library work for finding vector targeting motifs for specific diseases such as, for example, cancers. For example, we describe construction of a transductionally-targeted Infectivity-Selective Oncolytic Adenovirus (ISOAd) for selective cell entry into, and replication in, target tumor cells.

The system also can produce highly efficient cDNA library-expressing vectors, which can be used in various in vitro and in vivo methods such as, for example, drug screening. In addition, the methods can be an advance over conventional methods for Ad vector generation by enabling much quicker vector production and/or result in fewer mutation-prone vectors. To date, multiple groups have tried to improve the plasmid-to-virus conversion but the largest library size reported is at most on the order of $10^6$, which is minimal for cDNA library work and far less than sufficient for fiber library work for exploration of new targeting motif.

Briefly, our system uses engineered shuttle plasmids in which each shuttle plasmid in a plasmid library includes a library sequence and one loxP site. The system also uses a fiber pseudo-typed, genetically fiberless rescue adenovirus with one loxP site. These two components are introduced into specifically modified CRE recombinase-expressing vector producer cells. When our system was applied to the targeting motif library presented in HI-loop and AB-loop regions of adenovirus fiber respectively, we successfully generated libraries with a $10^{10}$ order of diversity. This can be $10^{10}$ times higher than the diversity that is routinely accomplished using conventional plasmid transfection methods and $10^4$ times higher than the largest library size reported in the field of adenovirus vector.

Our system was applied to the targeting motif library presented in AB-loop region of Ad fiber. This region is known to be responsible for the initial binding to the cellular receptor, coxackie-adenvirus receptor (CAR), and thought to be suitable for binding motif presentation. However, all previous trials have failed, presumably due to structural sensitivity of this region for virus assembly. We have, for the first time, successfully generated an adenovirus library with random targeting motifs in AB-loop, and the library size was confirmed to be in the order of $10^{10}$.

The AB-loop library virus was screened with pancreatic cancer cells and the convergence of the library sequence was observed, indicating successful selection. The isolated clone showed high infectivity and replication in the cells used for the selection process, but its infectivity and replication in another pancreatic cancer cell was negligible. This result indicates that a specific targeting motif was isolated by the screening of the adenovirus library.

Thus, we describe methods that can produce extremely high adenovirus vector production and excellent diversity of the library of targeting motif peptides presented compared to conventional methods. The methods can produce, for example, $10^{10}$ diversity of HI-loop and AB-loop libraries. The methods further permit successful identification of a targeting motif that exhibits specific binding of target cells.

The methods may have many different applications. First, the methods may be used, for example, to identify targeting motifs by screening a targeting motif library that presents various targeting motifs in the format of adenovirus. To date, many targeting motifs have been incorporated to adenoviral vector for disease-specific gene delivery such as, for example, cancer cell selective gene therapy. However, the incorporation of a pre-identified peptide motif into an adenoviral capsid has been mostly unsuccessful, and the few peptide motifs successfully incorporated into an adenovirus capsid have generally been non-specific. Our methods can permit high-throughput screening of a high diversity library presented in the form of an adenovirus. Our technology can enable the identification of such disease-specific and/or tissue-specific targeting motifs. One of the motifs we identified using such high-throughput screening showed selective binding and replication in target cells. This serves as an evidence of feasibility of such strategy for targeted vector development.

Second, methods describe herein can be used to identify vector structures useful for systemic targeting. For example, the methods described herein can lead to gene therapy treatment of cancer by administering a systemic vector carrying a therapeutic polynucleotide. Our strategy allows one to produce a highly diverse library of various portions of the adenovirus capsid including, for example, AB-loop, HI-loop, and hexon hyper-variable region (HVR). In particular, for example, hexon HVR can contribute to liver sequestration of adenovirus after systemic delivery. Thus, screening of a hexon HVR library for adenovirus with an increased circulation half-life after systemic administration can lead to the identification of a vector structure that slows and/or decreases liver sequestration, thereby extending circulation half-life and permitting targeted delivery of the vector to target cells (e.g., tumor cells) after systemic administration.

As noted above, we describe construction of a transductionally-targeted Infectivity-Selective Oncolytic Adenovirus (ISOAd) for selective cell entry into, and replication in, target tumor cells. Transductional targeting of oncolytic viruses requires the targeting moiety to be encoded by the virus genome to maintain the same infectivity profile in progeny viruses produced in the tumor. In many cases, incorporating a targeting motif into the Ad capsid can negatively affect adenovirus assembly and/or the affinity or specificity of the introduced ligand. One promising way to overcome this issue is to identify one or more targeting motifs by performing high throughput screening of a ligand library presented, from the outset of analysis, in the virus capsid.

Third, the methods may be used to generate adenovirus cDNA libraries for new drug identification. Our technique can allow one to generate a high diversity adenovirus library with cDNA as a transgene. Because adenoviruses can exhibit high in vitro and in vivo infectivity, an adenovirus cDNA library can be easily applied to the identification of disease relevant genes and high throughput screening of drugs.

Fourth, the methods described herein can be used to efficiently produce a vector that can be less prone to mutation than vectors produced using conventional methods. Conventional transfection-based methods for producing adenovirus vectors typically can generate about 1-2 plaque 10 days after transfection. Thus, amplification to one 6 cm dish can require at least two weeks. Compared to these conventional methods, our new method can induce full cytopathic effect in as little as two days after transfection. Also, since the batch does not depend on one starting plaque, our method is less prone to mutation of the clone. Thus, our method can permit one to more rapidly produce vector and/or produce vector that is less prone to mutation.

Fifth, the methods describe herein can be used to produce vectors useful for targeting cancer cells with unknown antigens. Because the adenovirus vectors can be screened in vitro or in vivo, vectors can be tested against not only known target molecules but also unknown surface molecules of intended target cancer cells.

Sixth, the methods described herein may be used to screen a library of vectors in vivo. Such in vivo screening methods can allow for more accurate identification of target motifs suitable for systemic applications. For example, in contrast to in vitro screening methods, in vivo screening methods also select for vectors that exhibit therapeutic effects when systemically administered and that are less susceptible to sequestration of the virus in certain organs. Thus, fiber-modified viruses generated using the methods described herein may reduce unwanted sequestration of the virus in certain organs and may increase virus distribution in, for example, tumor tissues. Thus, fiber-modified adenoviruses generated using the method described herein can allow targeted delivery of anti-tumor therapy.

Seventh, the methods describe herein can be used to produce vectors with in vivo therapeutic effect. Targeting of the oncolytic virus at the point of infection provides selectivity of the adenovirus vector on multiple levels: at the cellular level (e.g., selective replication), at the tissue level (e.g., cancer cell specific in situ distribution), and the organ level (e.g., reducing distribution to other organs). These three layers of selectivity can make the ISOAd more potent and more selective compared to current conditionally replicative adenoviruses, which solely depend on control during replication. In addition, vectors produced using the methods described herein are effective when administered systemically, including, for example, by intravenous injection. These results are surprising at least because vectors produced by other methods have been found to be ineffective when administered systemically.

Eighth, the adenoviruses and methods described herein may be used to provide systemic therapy of cancer by intravenous injection.

Ninth, the adenoviruses and methods described herein may be used to target hormone-therapy resistant prostate cancers. Specifically, for example, AdML-GERS and AdML-VRLL are targeted to prostate cancer cells, including for example, hormone-refractory, castration-resistant, and/or androgen receptor-negative prostate cancer cells.

Tenth, the adenoviruses and methods described herein may be used to target CD133-expressing cells, including, for example, CD133-positive cancer stem cells. Specifically, for example, AdML-TYML is targeted to CD133-expressing cells.

Construction of a Rescue Adenovirus

Figure 2A:
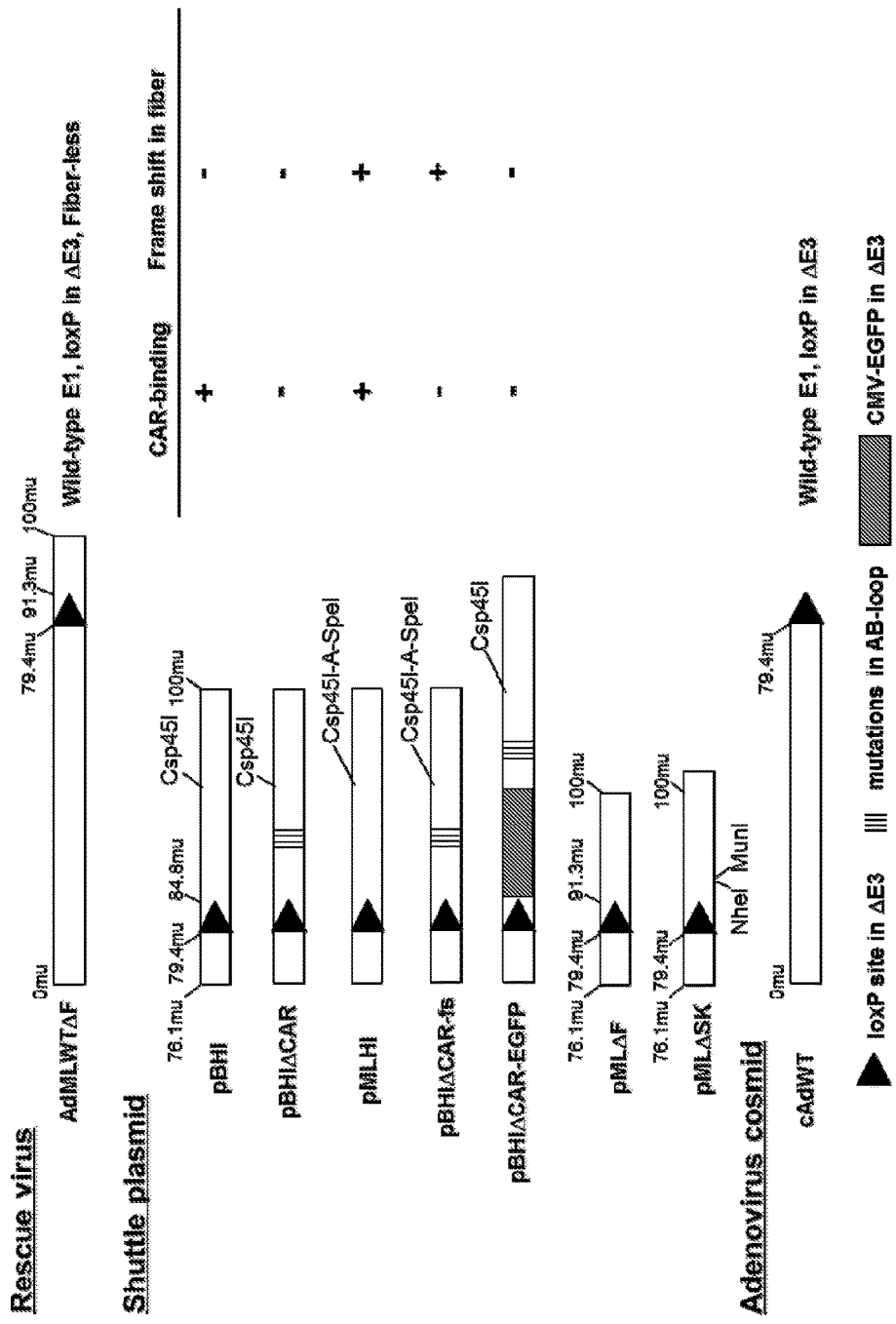
FIG. 2. Design of rescue virus, shuttle plasmid, and producer cells for recombinant adenovirus vector. Schematic presentation of adenoviral cosmids and fiber-modified shuttle plasmids. A single copy of a loxP sequence is substituted for the E3 gene (79.4-84.8 m.u.). The rescue virus has a wild-type E1 gene and a single loxP site at the E3 and fiber region deleted (79.4-91.3 m.u.). The DNA from the rescue virus was recombined with shuttle plasmid in adenovirus producer cell lines.

The rescue virus, AdMLWTΔF (FIG. 2(a)), is a fiberless adenovirus with pseudo-typed fiber, and was constructed by in vitro Cre recombination in a fiber-complementing cell line. The fiberless adenoviral shuttle plasmids, pMLΔF, includes 76.1-100 map unit (m.u.) of the adenoviral genome with a single loxP site at the E3 and a deletion of the fiber region (79.4-91.3 m.u.). The pMLΔF was recombined with cAD-WT to generate fiberless adenovirus AdMLWTΔF in vitro by Cre. After the recombination, the recombinant DNA was transfected to 644 cells, which express chimeric adenovirus fiber protein (adenovirus type 5 tail and shaft, and adenovirus type 3 knob), so that the vector can be pseudo-typed and propagated in the 644 cells.

Construction of an HI-Loop-Modified Shuttle Plasmid Library

HI-loop fiber-modified adenovirus library was described in detail in Miura et al., Gene Ther. 2007 October; 14(20):1448-60. Adenovirus libraries were based on the library backbone plasmids (pBMLHI and pBHIΔCAR-fs(+)) to display a random seven amino acid residue peptide on the HI-loop of the fiber knob domain. To generate HI-loop fiber-modified shuttle plasmid libraries, the degenerate oligonucleotide 5'-AACGGTACACAGGAAACAGGAGACA CAACTTTCGAA (NNK)$_7$ACTAGTCCAAGTGCAT ACT CTATGTCATTTTCATGG-3' (N=A, T, G or C; K=G or T; SEQ ID NO:1) served as a template for PCR with the primers 5'-GAAAC AGGAGACACAACTTTCGAA-3' (SEQ ID NO:2) and 5'-CATAGAGTATGCACTTGG ACTAGT-3' (SEQ ID NO:3). The PCR product was digested with Csp45I and SpeI (restriction sites underlined) and ligated into the same sites of pMLHI and pBHIΔCAR-fs(+) and transfected into ElectroMax DH5α-E electrocompetent cells (Invitrogen, Carlsbad, Calif.) by electroporation. The plasmid libraries constructed from pMLHI and pBHIΔCAR-fs(+) were designated as pMLHI-lib and pBHIΔCAR-lib, respectively. Both pMLHI-lib and pBHIΔCAR-lib contained 2×10$^8$ clones, excluding insertless and unsuitable clones. The complexity of plasmid libraries was estimated by the number of clones growing from a representative aliquot of the transformed bacteria on agar plates containing ampicillin. (FIG. 2(b)).

Construction of an AB-Loop-Modified Shuttle Plasmid Library

Adenovirus library with random mutations in AB-loop of the fiber knob was based on the backbone plasmid, pMLABΔSK. Two steps of PCR were performed to generate AB-loop-modified shuttle plasmid library. For the first step, three PCR products were prepared; The degenerate oligonucleotide 5'-AAGCTAACTTTGTGGACCACACCAGCT CCATCTCCTAA C(NNK)$_7$GATGCTAAACTCACTTTG-GTCTTAACAAAATGTGGCAGT-3' (N=A,T,G or C; K=G or T; SEQ ID NO:4) served as a template for PCR with the primers 5'-AAGCTAACTTT GTGGACCAC-3' (SEQ ID NO:5) and 5'-ACTGCCACATTTTGTTAAGA-3' (SEQ ID NO:6). For the upper PCR product (709 bp), adenovirus type 5 genome served as a template for PCR with the primers 5'-AATTGCTAGCCCTGCAAACATCAG-3' (AB-upper S, SEQ ID NO:7) and 5'-GGTCCACAAAGTTAGCTTATC-3' (SEQ ID NO:8). For the lower PCR product (442 bp), adenovirus type 5 genome served as a template for PCR with the primers 5'-TTAACAAAATGT GGCAGTCAA-3' (SEQ ID NO:9) and 5'-AATTCAATTGAAAAATAAACACGTT-GAA-3' (AB-lower AS, SEQ ID NO:10).

These three PCR products, which were mixed with the equal mol ratio (upper PCR:library PCR:lower PCR=1:5:2), were used for the template for first step PCR without primers. In total, 26 cycles of PCR were carried out as follows 96° C. for 5 seconds, 52° C. for 5 seconds, 68° C. for 45 seconds without primers.

The second round of PCR was carried out using a first round PCR product for the template with the primers AB-upper S and AB-lower AS in 50 μl PCR solution containing 1.5 mM MgCl$_2$, 0.2 mM dNTPs, 1 U of recombinant Taq polymerase. In total, 30 cycles of PCR were carried out as follows: 96° C. for 5 seconds, 64° C. for 5 seconds, and 68° C. for 45 seconds.

The final PCR product was digested with NheI and MunI, and then ligated into the same sites of pMLABΔSK and transfected into ElectroMAX DH5α-E electrocompetent cells (Invitrogen, Carlsbad, Calif.) by electroporation. The plasmid library constructed from pMLABΔSK was designated as pMLAB-lib. The pMLAB-lib contained 3×10$^8$ clones, excluding insertless and unsuitable clones. The complexity of plasmid libraries was estimated by the number of clones growing from a representative aliquot of the transformed bacteria on agar plates containing ampicillin (FIG. 2(c)).

Development of Basic Constructs for Generating Recombinant Adenovirus Vector

Figure 1:
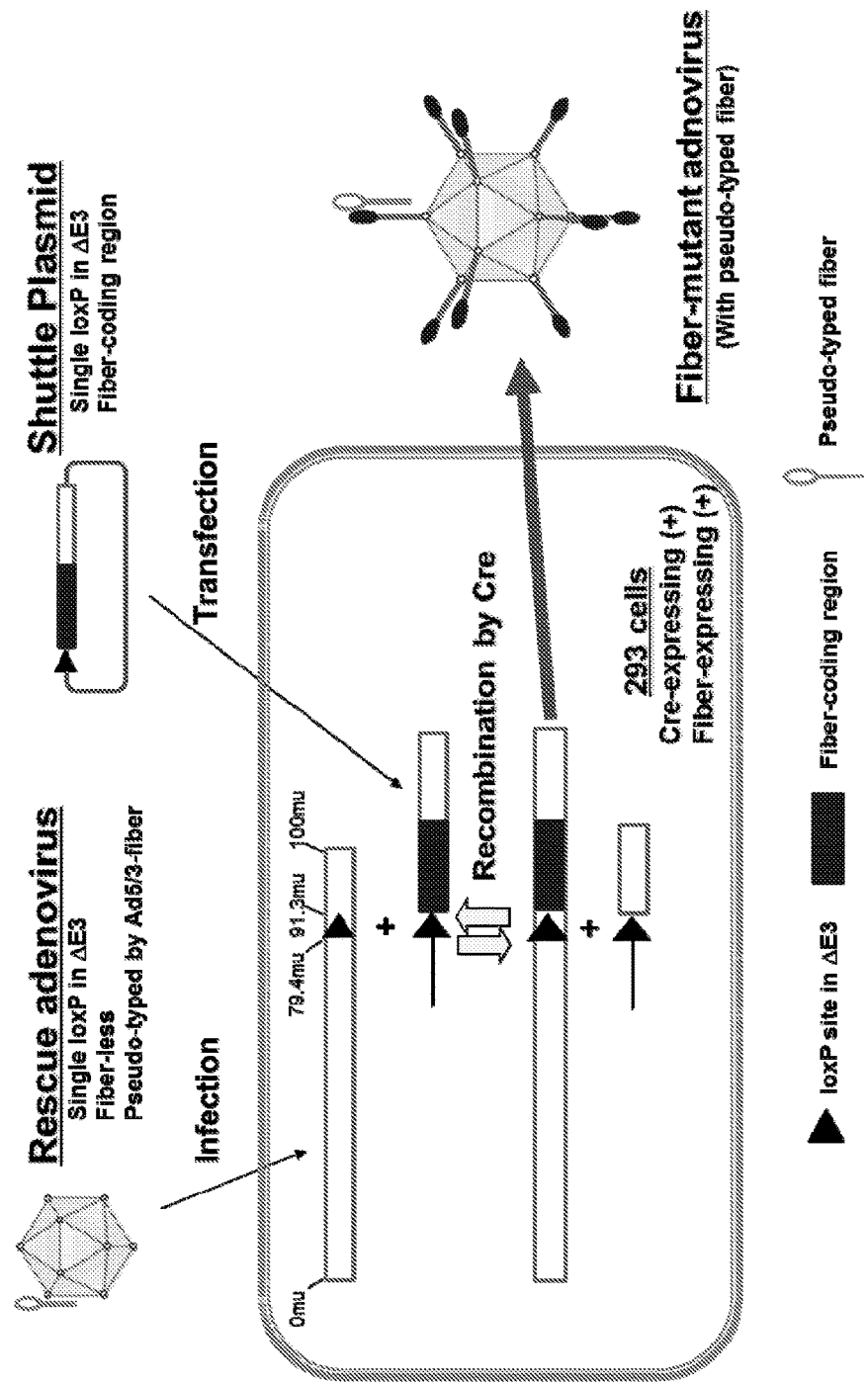
FIG. 1. Basic Strategy for Constructing Fiber-modified Adenovirus Vector. Construction of fiber-modified adenovirus vector. The vector was produced by a Cre-lox recombination system in producer cells between a fiber-modified shuttle plasmid and adenoviral DNA from the rescue virus. The resultant virus was pseudo-typed and replicated in producer cells using fiber-complementing system and could be directly applied following screening steps.

To establish a basic construct for generating recombinant adenovirus vector, we first examined whether the vectors could be produced by a Cre-lox recombination system in producer cells between a fiber-modified shuttle plasmid and adenoviral DNA from the rescue virus with fiber-complementing. (FIG. 1). For gene recombination, approximately 1×10$^6$ 293-CRE cells or 293-CRE-69 cells were infected with 10,000 vp/cell of rescue virus, AdMLWTΔF, for two hours in a 6-cm culture dish. After 24 hours incubation at 37° C., cells were transfected with 5 μg of the shuttle plasmid with fiber-coding region. After 48 hours of transfection, cells were harvested by scraping and the crude viral lysate (CVL) was eluted by 3-4 freeze per thaw cycles. First, the pBHI(Csp), CAR-binding positive shuttle plasmid, was transfected into 293-CRE cells, which had been infected with rescue virus, AdMLWTΔF, 24 hours before the transfection. Adenoviral cytopathic effect (cpe) were clearly detected four days after the transfection.

We next confirmed whether the fiber-complement system could propagate fiber-modified adenovirus vector using pBHIΔCAR(Csp) and pMLHI. In 293-CRE-69 cells, clear cytopathic effects were detected with CAR-binding negative plasmid and reading frame-shifted plasmid at day 4, and half of cells were dead after the infection of pseudo-typed fiberless adenovirus. In 293-CRE cells, however, no cytopathic effects were detected at day 7 with these fiber-modified shuttle plasmids. (Table 1).

TABLE 1

Rescue of fiber-modified adenovirus vector independent of CAR-binding

| Cells | Fiber modifications | | | |
|---|---|---|---|---|
| | wt | CAR-binding(−) | Reading frame shifted | Fiberless |
| 293-CRE Fiber-expressing(−) | + | − | − | − |
| 293-CRE-69 Fiber-expressing(+) | + | + | + | ++ |

+: clear cpe were detected at Day 4
−: no cpe were detected at Day 7
++: clear cpe were observed at Day 2

Figure 3:
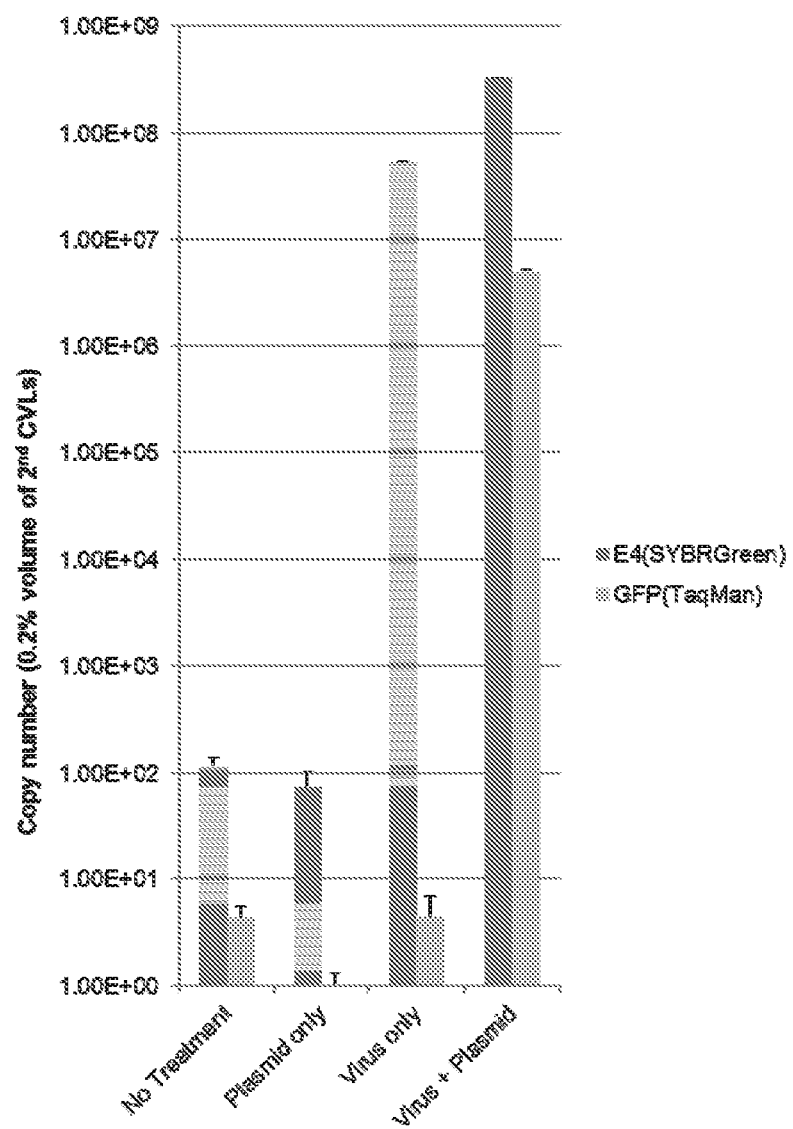
FIG. 3. Efficiency of recombinant adenovirus production. The efficiency of generating recombinant adenovirus vector was examined by quantitative PCR. 5 µg of pBHIDCAR-GFP were transfected into 293-CRE-69 cells after the infection of AdMLWTDF at 10,000 vp/cell. Two days after the transfection, first crude viral lysates were collected and 10% volumes of the first crude viral lysates were used to infect HEK293 cells. 24 hours after the HEK293 infection, second crude viral lysates were collected and 10% volumes of the second crude vial lysates were treated with DNaseI. 0.2% of the first crude viral lysates were analyzed by qPCR with E4 primers (SYBRGreen) for the total virus copy number and GFP-probe (TaqMan Probe) for the recombinant viral copy number.

We then examined the efficiency of generating recombinant adenovirus vector. 5 μg of pBHIΔCAR-GFP were transfected into 293-CRE-69 cells after the infection of AdMLWTΔF at 10000 vp/cell. Two days after the transfection, first crude viral lysates were collected and 10% volumes of the first crude viral lysates were infected to HEK293 cells. 24 hours after the infection, second crude viral lysates were collected and 10% volumes of the second crude viral lysates were treated with DNaseI. After extracting DNA, 2% volumes of the second crude viral lysates (the equivalent of 0.2% of first crude viral lysates) were analyzed by quantitative PCR with E4 primers for the total virus copy number and GFP Probe for the recombinant viral copy number. There were, at minimum, 5×10$^6$ copies in 0.2% of first crude viral lysates, so that the vector generation from this method was 10$^9$ copies in single 6-cm culture dish. (FIG. 3)

Production of a Fiber-Modified Adenovirus Library

The fiber modified plasmid libraries, pMLHI-lib and pBHIΔCAR-lib, were transfected into 293-CRE-69 cells, which had been infected AdMLWTΔF 24 hours before. Then, the genome from the rescue virus AdMLWTΔF was recombined with shuttle plasmid library in 293-CRE-69 cells by Cre. Forty-eight hours after the transfection, the first generation of the adenovirus library was produced. (FIG. 4). Since direct transfer of the adenoviral DNA from shuttle plasmid library into 293-CRE-69 cells might lead to an uptake of more than one library DNA per cell, the packaged adenovirus genome may not encode the peptide displayed on the fiber knob, impeding the selection process and subsequent identification of the library clone. In the first generation library, each adenovirus was pseudo-typed with Ad5/3 fiber, which enables one to start screening at the wide types of targeting cell. Additionally, at the beginning of screening, using the infection of the first-generated library to the targeting cells at a low multiplicity of infection avoids this problem. The virus production efficiency was highly improved by optimizing several factors such as, for example, the timeline of rescue-virus infection and shuttle plasmid transfection, the titer of rescue virus, the concentration of shuttle plasmid library.

To estimate how many different adenoviruses in HI-loop library were produced by our rescue virus system, we set up dilution experiments with shuttle plasmid library and shuttle plasmid expressing GFP, the pBHIΔCAR-GFP, were mixed with pBHIΔCAR-lib at various ratios (1:1×10$^4$, 1:1×10$^5$, 1:1×10$^6$, 1:1×10$^7$, 1:1×10$^8$, and 1×10$^9$), transfected with the rescue virus into 293-CRE-69 cells. After two days, 2% of the crude viral lysates were treated with DNaseI, the viral DNA was extracted, and then quantitative PCR was performed to determine total viral copy numbers and recombinant viral copy numbers. Total viral copy numbers were determined by SYBRGreen with E4 primers; recombinant viral copy numbers were determined by Taqman Probe for GFP gene. GFP gene was detected in a dilution range of 2×10$^6$ to 4×10$^7$ (FIG. 8). The dilution experiment suggested that the diversity of the library includes more than 5×10$^8$ per 6-cm dish. (FIG. 5(a), (b)).

We then generated a library of AB-loop mutants. The AB-loop of the fiber knob includes CAR-binding domains. If an AB-loop mutant allows the display of peptides and/or the insertion of ligands, the AB-loop may be an effective binding motif-presenting region. Introducing mutations into the AB-loop can be problematic using conventional methods, however, because mutations in the AB-loop can produce adenoviral conformation changes.

The new high-throughput library system described herein can provide a way to select new classes of adenovirus with AB-loop mutations. We performed dilution experiments for screening an adenovirus AB-loop mutant library with a shuttle plasmid library. A shuttle plasmid expressing GFP (pBHIΔCAR-GFP) was mixed with pMNAB-lib at various ratios (1:1×10$^4$, 1:1×10$^5$, 1:1×10$^6$, 1:1×10$^7$, 1:1×10$^8$, and 1×10$^9$), then transfected with the rescue virus into 293-CRE-69 cells. After two days, 2% of the crude viral lysates were treated with DNaseI, viral DNA extracted, and then subjected to quantitative PCR to determine total viral copy number and recombinant viral copy number. Total viral copy numbers were determined by SYBRGreen with E4 primers; recombinant viral copy numbers were determined by Taqman Probe for the GFP coding region. GFP coding region was detected up to the 1×10$^7$ dilution, and five copies were existing in single 6-cm culture dish at minimum. The dilution experiment suggested that the diversity of the library includes more than 1×10$^9$ per 6-cm dish. (FIG. 5(c), (d)).

Selection of AB-Loop Fiber-Modified Adenovirus Library Clones Targeting Panc1 Cells To demonstrate that in vitro screening could produce modified-fiber adenovirus clones with high transduction efficiency to target cells, the Panc1 cell line was infected at an multiplicity of infection of 1 (FIG. 6). Since the library used in the screening was collected from ten 6-cm dishes, the theoretical diversity of the fiber-modified adenoviruses in the library was estimated to be approximately 1×10$^{10}$, and final concentration of the virus library was prepared as 5×10$^8$ vp/ml. Infection at such a low multiplicity of infection allows the average chance of adenovirus exposure to be less than one virus genome per cell, reducing the likelihood of a mismatch between the phenotype and the sequence coding in the adenovirus genome. In the initial phase of the screening, many low-affinity or nonspecific viruses might bind and internalize into the Panc1 cells because each virus was pseudo-typed. However, for the viruses presenting modified-fiber that matched modified adenoviral genome, using a replication-competent adenovirus could allow for the rapid spreading of the most efficient viruses in the library in following replication steps, thereby leading to an effective enrichment of such viruses. Amplified and expanded adenoviruses were recovered and subjected to three more rounds of selection. The DNA region containing the AB-loop mutant of adenovirus recovered from three rounds of selection was then amplified by PCR. DNA sequencing of the PCR products revealed enrichment of several candidates, and the most abundant consensus sequences after two rounds of selection were VTINRSA (SEQ ID NO:12) and THLSIYA (SEQ ID NO:14) (Table 2).

The asterisks in the sequences of Tables 2-6 indicate a stop codon inserted into the oligonucleotide encoding the protein sequence. Although viruses including such a sequence would not be expected to produce a functional fiber, the viruses can still replicate if co-infecting with a virus including a functional fiber.

TABLE 2

AB-loop mutant sequences from adenovirus library on Panc1 cells

| Initial Library | Selection Round | | |
|---|---|---|---|
| | 1 | 2 | 3 |
| AAWV (SEQ ID NO: 26) | CSLNGGG (SEQ ID NO: 41) | THLSIYA (SEQ ID NO: 14) | THLSIYA (SEQ ID NO: 14) |
| AMYSTLY (SEQ ID NO: 27) | EGRRVGG (SEQ ID NO: 42) | THLSIYA (SEQ ID NO: 14) | THLSIYA (SEQ ID NO: 14) |
| DARVD*D (SEQ ID NO: 28) | ETSSLLF (SEQ ID NO: 43) | THLSIYA (SEQ ID NO: 14) | VTINRSA (SEQ ID NO: 12) |
| FLAFCFA (SEQ ID NO: 29) | GGREKKD (SEQ ID NO: 44) | THLSIYA (SEQ ID NO: 14) | VTINRSA (SEQ ID NO: 12) |
| IHSALRA (SEQ ID NO: 30) | NKAHFGN (SEQ ID NO: 45) | VTINRSA (SEQ ID NO: 12) | VTINRSA (SEQ ID NO: 12) |
| IRVWK*I (SEQ ID NO: 31) | SSILWIG (SEQ ID NO: 46) | VTINRSA (SEQ ID NO: 12) | VTINRSA (SEQ ID NO: 12) |
| IYYTIST (SEQ ID NO: 32) | TGACSWS (SEQ ID NO: 47) | VTINRSA (SEQ ID NO: 12) | VTINRSA (SEQ ID NO: 12) |
| NRRTILM (SEQ ID NO: 33) | THLSIYA (SEQ ID NO: 14) | VTINRSA (SEQ ID NO: 12) | VTINRSA (SEQ ID NO: 12) |
| PGAGWRP (SEQ ID NO: 34) | THLSIYA (SEQ ID NO: 14) | VTINRSA (SEQ ID NO: 12) | VTINRSA (SEQ ID NO: 12) |
| RNNDDTL (SEQ ID NO: 35) | THLSIYA (SEQ ID NO: 14) | VTINRSA (SEQ ID NO: 12) | VTINRSA (SEQ ID NO: 12) |
| RVSRNRL (SEQ ID NO: 36) | THLSIYA (SEQ ID NO: 14) | | |
| SERGDWA (SEQ ID NO: 37) | THLSIYA (SEQ ID NO: 14) | | |
| VEVGGGW (SEQ ID NO: 38) | THLSIYA (SEQ ID NO: 14) | | |
| WGAVFGG (SEQ ID NO: 39) | THLSIYA (SEQ ID NO: 14) | | |
| WHHCPYS (SEQ ID NO: 40) | THLSIYA (SEQ ID NO: 14) | | |
| | VGAWTGR (SEQ ID NO: 48) | | |
| | VYPTHGK (SEQ ID NO: 49) | | |

Characterization of Adenovirus with Selected Fiber

Figure 7A:
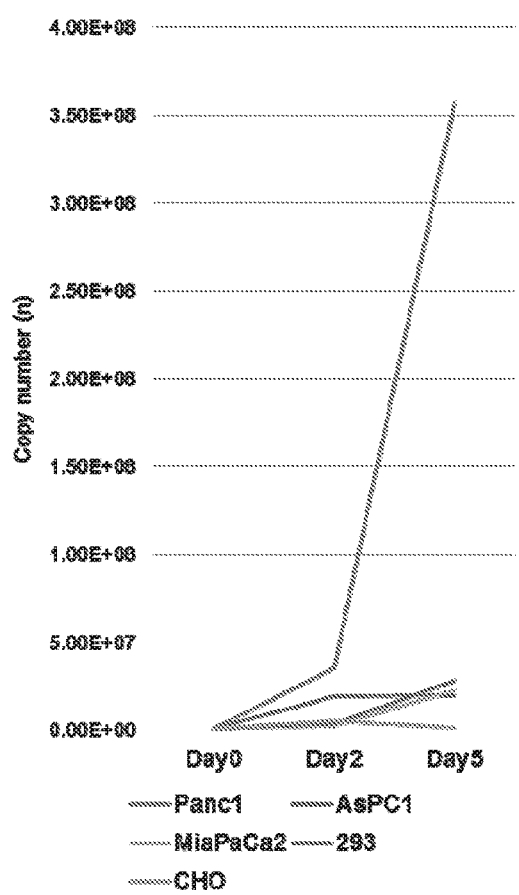
Figure 7B:
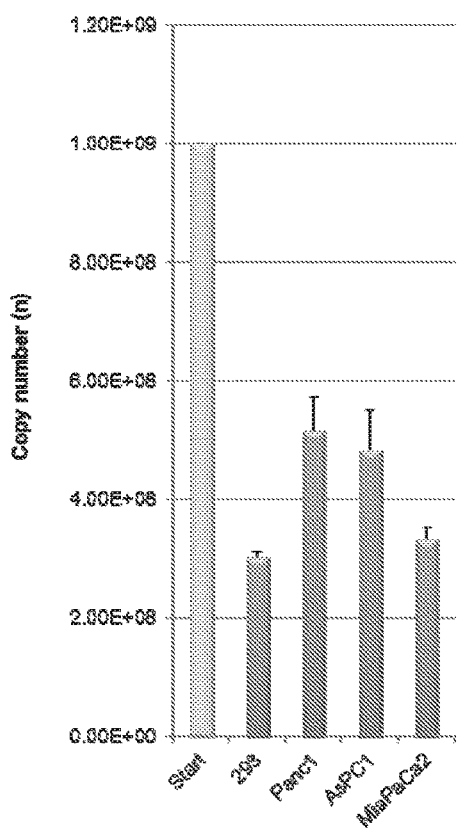

To test the binding and replication ability of the selected virus pool, we analyzed the copy number of AB-mutants virus pool from the third round of screening on Panc1 cell line by quantitative PCR (FIG. 7(a), 7(b)). The third virus pool was infected at 0.1 vp/cell at 37° C. for two hours into Panc1, AsPC1, MiaPaCa2, CHO, or HEK293 cells. The cells were intensively washed twice in PBS after the infection and incubated at 37° C. for either two days or five. Quantitative PCR was performed with the viral DNA from crude viral lysates. The quantitative PCR showed that replication ability of third virus pool was ten-fold higher in Panc1 cells than in other cell lines at day 5 (FIG. 7(a)). Next, to examine binding activity, the third virus pool was infected at 100 vp/cell at 4° C. for two hours into Panc1, AsPC1, MiaPaCa2, or HEK293 cells. The binding activity observed with Panc1 cells also was higher than that observed in the other cell lines (FIG. 7(b)). Since the replication of this virus pool in HEK293 cells, which express CAR at a higher level than do than Panc1 cells, was pretty low, these results suggest that these mutant motifs in AB-loop might inhibit native tropism, contributing to the targeting nature of the virus.

Isolation of AB-Loop-Modified Adenoviral Clones for Mesothelin Targeting

Next, we used mesothelin (MSLN) as a target cell-surface molecule for library screening. MSLN may be overexpressed in, for example, pancreatic cancer, ovarian cancer, and malignant mesothelioma, while little or no expression is typically detected in normal tissues. In order to isolate a MSLN-targeting adenovirus, we established the 293 cells over-expressing MSLN (293-MSLN), and the library screening was performed with this cell line by replication-based selection (FIG. 9). Since the library used in the screening was collected from ten 6-cm dishes, the library diversity of the fiber-modified adenoviruses was considered to be 5×10$^9$. In each round, the DNA was extracted from viral solution and the region corresponding to the AB-loop of adenovirus was sequenced after being cloned into the plasmid. The convergence of the sequence was observed as early as the first screening round and the VTINRSA (SEQ ID NO:12) sequence became dominant after the second round (Table 3).

TABLE 3

AB-loop mutant sequences from adenovirus library on 293-MSLN cells

| Initial Library | Selection Round 1 | Selection Round 2 | Selection Round 3 |
|---|---|---|---|
| AAWV (SEQ ID NO: 26) | THLSIYA (SEQ ID NO: 14) | THLSIYA (SEQ ID NO: 14) | VTINRSA (SEQ ID NO: 12) |
| AMYSTLY (SEQ ID NO: 27) | THLSIYA (SEQ ID NO: 14) | THLSIYA (SEQ ID NO: 14) | VTINRSA (SEQ ID NO: 12) |
| DARVD*D (SEQ ID NO: 28) | THLSIYA (SEQ ID NO: 14) | VTINRSA (SEQ ID NO: 12) | VTINRSA (SEQ ID NO: 12) |
| FLAFCFA (SEQ ID NO: 29) | THLSIYA (SEQ ID NO: 14) | VTINRSA (SEQ ID NO: 12) | VTINRSA (SEQ ID NO: 12) |
| IHSALRA (SEQ ID NO: 30) | THLSIYA (SEQ ID NO: 14) | VTINRSA (SEQ ID NO: 12) | VTINRSA (SEQ ID NO: 12) |
| IRVWK*I (SEQ ID NO: 31) | THLSIYA (SEQ ID NO: 14) | VTINRSA (SEQ ID NO: 12) | VTINRSA (SEQ ID NO: 12) |
| IYYTIST (SEQ ID NO: 32) | THLSIYA (SEQ ID NO: 14) | VTINRSA (SEQ ID NO: 12) | VTINRSA (SEQ ID NO: 12) |
| NRRTILM (SEQ ID NO: 33) | THLSIYA (SEQ ID NO: 14) | VTINRSA (SEQ ID NO: 12) | VTINRSA (SEQ ID NO: 12) |
| PGAGWRP (SEQ ID NO: 34) | VTIDRSA (SEQ ID NO: 50) | VTINRSA (SEQ ID NO: 12) | VTINRSA (SEQ ID NO: 12) |
| RNNDDTL (SEQ ID NO: 35) | VTINRSA (SEQ ID NO: 12) | VTINRSA (SEQ ID NO: 12) | VTINRSA (SEQ ID NO: 12) |
| RVSRNRL (SEQ ID NO: 36) | VTINRSA (SEQ ID NO: 12) | | |
| SERGDWA (SEQ ID NO: 37) | VTINRSA (SEQ ID NO: 12) | | |
| VEVGGGW (SEQ ID NO: 38) | VTINRSA (SEQ ID NO: 12) | | |
| WGAVFGG (SEQ ID NO: 39) | VTINRSA (SEQ ID NO: 12) | | |
| WHHCPYS (SEQ ID NO: 40) | VTINRSA (SEQ ID NO: 12) | | |
| | VTINRSA (SEQ ID NO: 12) | | |
| | VTINRSA (SEQ ID NO: 12) | | |
| | VTINRSA (SEQ ID NO: 12) | | |

Binding of the Isolated Adenovirus Clone to Mesothelin

Figure 10A:
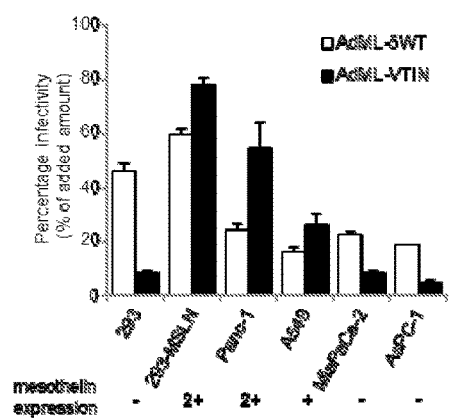
Figure 10B:
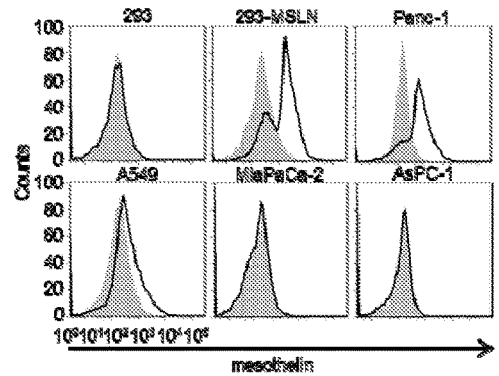
Figure 10C:
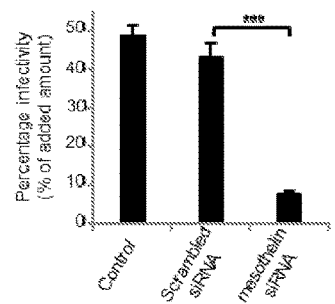
Figure 10D:
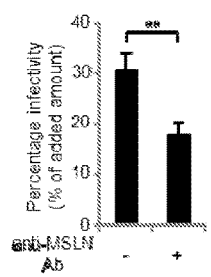

When binding of the isolated adenovirus with the VTINRSA (SEQ ID NO:12) motif (AdML-VTIN) was analyzed in 293, 293-MSLN, Panc-1, A549 and MiaPaCa-2, it corresponded to the level of cell surface MSLN-expression analyzed by flow-cytometry (FIG. 10a, b). In particular, binding of AdML-VTIN to 293-MSLN cell (showing highest MSLN expression) was significantly higher than that in any other cells. In order to further confirm the role of MSLN for AdML-VTIN infection, we analyzed the effect of MSLN inhibition on the binding of AdML-VTIN by employing siRNA and antibody against MSLN. The anti-MSLN siRNA almost completely suppressed AdML-VTIN binding to MSLN-expressing cells, 293-MSLN (FIG. 10c and FIG. 11a) and Panc-1 (FIG. 10b). The anti-MSLN antibody also significantly inhibited the binding of AdML-VTIN to 293-MSLN (FIG. 10d). This data indicated that MSLN was a receptor moiety for AdML-VTIN and provided an important evidence showing functionality of our high-throughput large-library screening for identification of the selective targeting moiety binding against the specific cell surface molecule of the target cells.

Characterization of the Identified Infectivity-Selective Oncolytic Adenovirus (ISOAd)

Figure 12A:
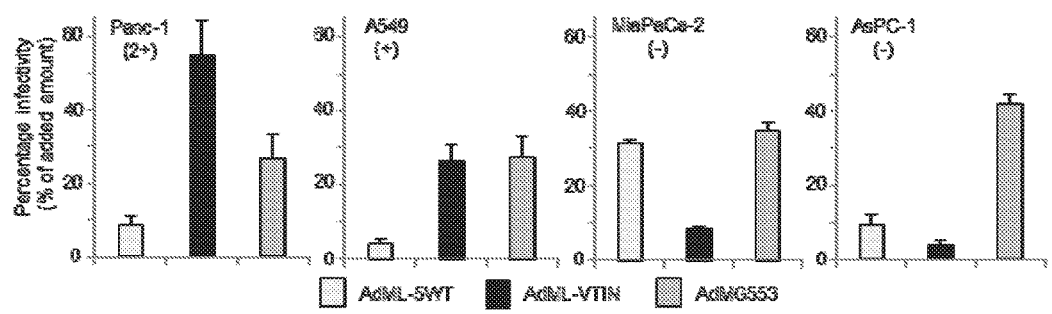
Figure 12B:
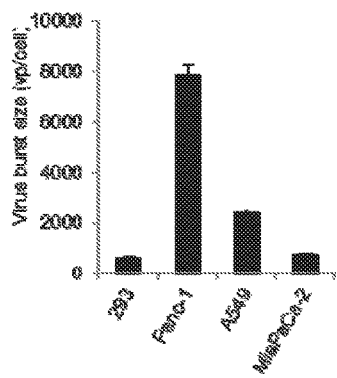

The newly identified transductionally-retargeted ISOAd (AdML-VTIN) was compared to the control adenoviruses with ether the native Ad5 fiber (AdML-5WT) or the infectivity-enhanced Ad5/Ad3 fiber (AdMG553) in the cell lines showing different levels of MSLN expression (FIG. 12a). In Panc-1 (MSLN strongly-positive pancreatic cancer), the binding ability of the AdML-VTIN was 5-fold higher than that of AdML-5WT and twice as high as that of AdMG553. The binding ability in A549 (MSLN moderately-positive) was also higher than that of AdML-5WT. Conversely, AdML-VTIN binding to MiaPaCa-2 or AsPC-1 (MSLN negative) was as low as the background level. Importantly, the binding of AdML-VTIN to Panc-1 was stronger than that with the Ad5/Ad3 modified fiber which was reported to show the strongest infectivity in many CAR-negative cancer cells including pancreatic cancer. In the context of virus replication, AdML-VTIN showed exponential amplification selectively in MSLN-positive cells and the extent of virus burst corresponded with MSLN-expression of each cell line (FIG. 12b). Therefore, the VTINRSA motif was identified as the first genetically-coded Ad targeting motif with improved potency and selectivity.

Figure 13A:
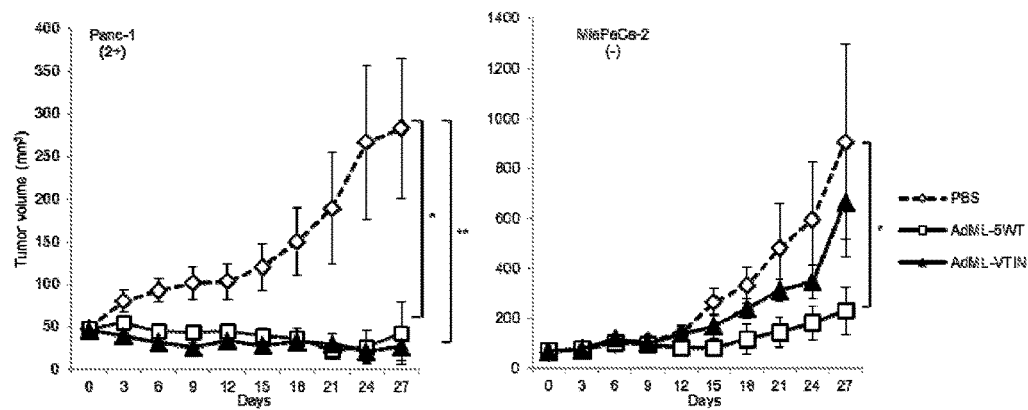

In Vivo Anti-Tumor Effect and Virus Replication of Transductionally-Retargeted Oncolytic Adenovirus The in vivo therapeutic effect of the MSLN-retargeted oncolytic Ad was analyzed in Panc-1 (MSLN-positive) and MiaPaCa-2 (MSLN-negative) pancreatic cancer subcutaneous xenografts (FIG. 13a). When tumors reached 5-7 mm, $10^{10}$ vp of AdML-VTIN or AdML-5WT were injected intratumorally. The MSLN-targeted virus (AdML-VTIN) exhibited significant tumor volume reduction in MSLN-positive Panc-1 xenografts (P=0.006 vs. PBS-treated control), while it did not show anti-tumor effect in MSLN-negative MiaPaCa-2 tumors. Disappearance of tumors was observed only in the Panc-1 xenografts treated with the MSLN-targeted AdML-VTIN virus (4 out of 8 mice).

Figure 13B:
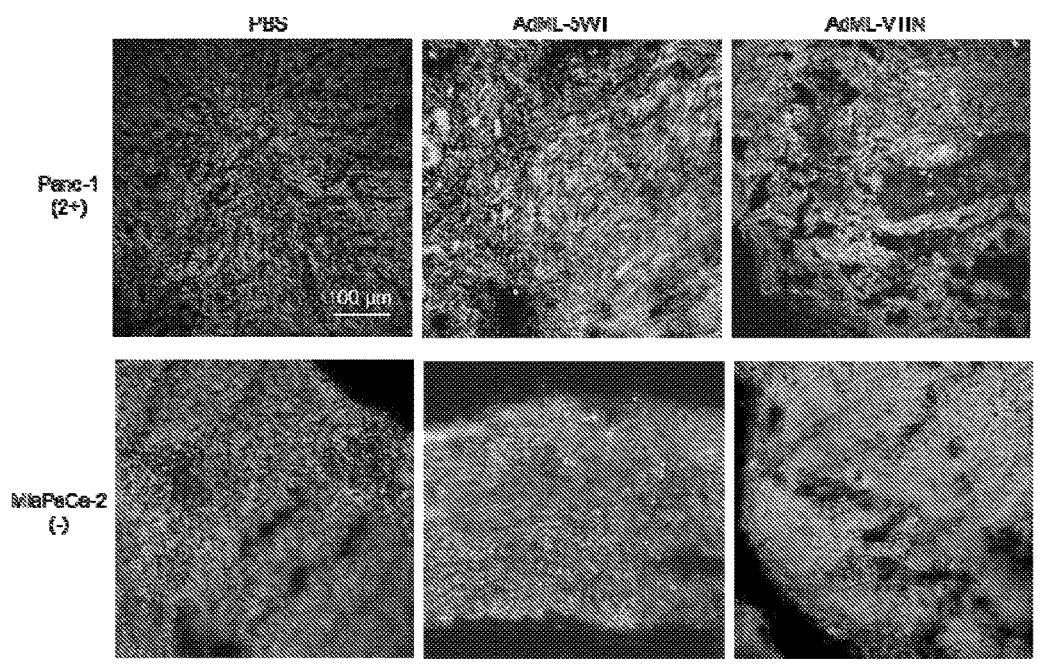

To investigate replication and intratumoral spread of the virus, we performed a separate experiment with the same setup and stained the tumor specimens for the virus structural protein, hexon, five days after infection. After treatment with AdML-VTIN, a majority of the cells in the Panc-1 tumors expressed high level of hexon protein, while there were few low-intensity hexon-positive cells in MiaPaCa-2 specimens. The non-targeted virus, AdML-5WT, resulted in moderate level of hexon expression in both Panc-1 and MiaPaCa-2 xenografts. In MSLN-positive Panc-1 tumors, the hexon immunostaining signal with AdML-VTIN was remarkably higher than that with AdML-5WT (FIG. 13b).

Figure 13C:
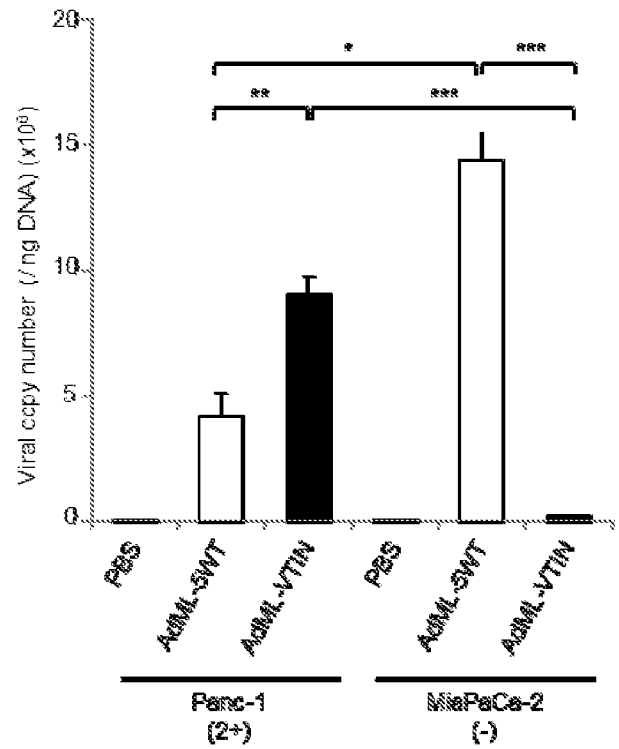

The virus copy number in the treated tumor was determined by qPCR with the primers for the Ad E4 region. In Panc-1, the virus copy number (Day 5) with AdML-VTIN was twice as high as that with AdML-5WT (P=0.002). In MiaPaCa-2, AdML-VTIN viral replication was significantly lower compared to AdML-5WT (P=0.00003). When virus replication was compared between MSLN-positive and negative xenografts, the copy number of AdML-VTIN was noticeably higher (40-fold) in Panc-1 than that in MiaPaca-2 (P=0.00003) (FIG. 13c). These data indicated the viral replication of MSLN-retargeted adenovirus correlates with the anti-tumor effect. These experiments confirmed the selectivity and potency of the oncolytic andenovirus with the VTINRSA (SEQ ID NO:12) as a targeting motif against MSLN-positive tumors.

Figure 14A:
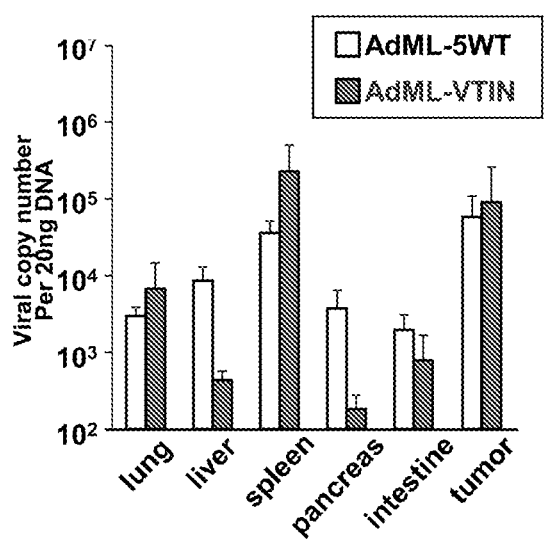
Figure 14B:
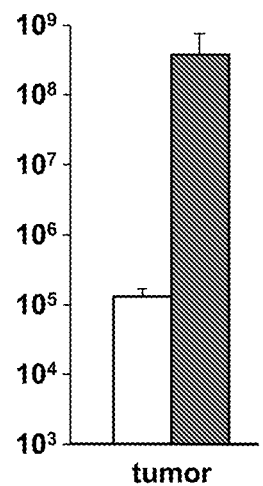

In Vivo Distribution of the Novel Fiber-Modified Virus After Systemic Administration In vivo distribution of systemically administered virus was assessed in athymic nude mice with MSLN positive xenografts. When the Panc-1 tumor became 5-7 mm, $10^{11}$ vp of viruses with the MSLN-binding VTIN motif (AdML-VTIN) or $10^{11}$ vp of viruses with the wild type fiber (AdML-5WT) were injected respectively into the tail vein of the mice. The major organs were harvested 48 hrs after injection, and DNA was isolated form them. The qPCR analyses of virus sequence revealed decrease of the VTIN-virus distribution in most of the organs and increase in the tumor, compared to the virus with wild type fiber. Particularly, the decrease in the liver was significant and more than one order of magnitude (FIG. 14a). When the virus quantity in the tumor was compared after 7 days of injection, the quantity of VTIN virus was more than 3 orders of magnitude higher than that of wild type virus (FIG. 14b).

High throughput screening of a targeting ligand library in an adenovirus format can be an attractive way to develop infectivity-selective oncolytic adenoviruses. Achieving the required library size, however, has been extremely difficult due to certain virological barriers: (i) poor transfection efficiency of a large Ad-coding plasmid; (ii) insufficient recombination efficiency; and/or (iii) unintended restriction of the clones based on the infectivity in producer cells. The novel pseudotyped rescue virus system described herein is designed to circumvent one or more of these barriers. In order to reduce the possibility of having multiple copies of one clone in the library, we determined library diversity using a limit dilution assay. Our system reproducibly achieves a level of diversity of at least $5 \times 10^9$. A library of this size can allow screening of random amino acid sequences as long as at least seven amino acids, substantiating the use of adenovirus as an expression platform for biologically meaningful library screening.

Moreover, modifying adenovirus fiber for targeted in vivo distribution of the adenovirus following systemic administration has proven difficult using conventional methods due, at least in part, to difficulty successfully coding the targeting motif into the virus genome. The fiber-modified virus generated using our new method, however, can reduce unwanted sequestration of the virus in certain organs (e.g., liver and/or pancreas, see FIG. 14a) and increase virus distribution in, for example, tumor tissues. Thus, fiber-modified adenoviruses generated using the method described herein can allow targeted delivery of anti-tumor therapy.

The position into which the targeting motif is placed in the adenovirus may be important for successful targeting. The AB-loop of adenovirus fiber can shapes the CAR-binding domain and can mediate initial viral binding for infection. However, mutations in the AB-loop can induce adenoviral conformation changes. Until now, therefore, attempts to construct adenoviral fiber-modified-library presented library peptides in the HI-loop of the fiber knob, which accepts a wide variety of inserts such as, for example, the RGD motif. In this work, we produced a large-size adenovirus library with targeting motifs successfully presented in the AB-loop of the adenovirus fiber knob region by exploiting a highly efficient vector generation system.

In order to prove the functionality of the library system and the high throughput screening, we performed a screening of the AB-loop adenoviral library for mesothelin (MSLN) as a target. MSLN is a surface glycoprotein attached to the cell membrane by a glycosylphosphatidylinositol anchor and is postulated to function in cell adhesion. MSLN shows overexpression in many malignancies including, for example, pancreatic cancer, malignant mesothelioma, and ovarian cancer. Therefore, our MSLN-targeted vector has potential for application in many MSLN expressing cancers. Although a conditionally replicative Ad with the MSLN promoter-based control has been reported (Tsuruta Y et al., 2008, *Clin Cancer Res* 14:3582-3588), the fiber in this structure does not possess specificity to the target cancer cells, and thus the adenovirus is not selective at the step of infection. Such vectors experience sequestration by non-target organs and/or cells and may impose higher risk of toxicity because they may infect non-cancer cells. Therefore, targeting at the stage of infection is critical for circumventing the aforementioned issues both by increasing infection in cancer cells and decreasing the absorption of viral particles by non-target cells around the region. The target specificity and anti-tumor potency are attributes of fully functional oncolytic viruses.

The MSLN-targeted ISOAd (Infectivity-Selective Oncolytic Adenovirus) generated in this study with the newly identified targeting motif exhibited powerful infectivity of cancer cells overexpressing MSLN. Moreover, the oncolytic activity of the virus with this targeting motif was highly selective in vitro and in vivo. These data provide a foundation for a new category of cancer therapeutics, the infectivity-selective oncolytic virus. Our new library system is an innovative technology which enables the development of the ISOAd not only for the known target molecules but also for unknown surface molecules of intended target cancer cells.

In this study, we report the construction of an Infectivity-Selective Oncolytic Adenovirus (ISOAd), showing both selectivity for and potency against the target cancer cells. The ISOAd presented here has several important applications. For non-enveloped viruses, infection steps are mediated by protein binding, which is more specific than lipid membrane fusion. In this sense, transductional targeting of non-enveloped viruses such as, for example, adenovirus offers the possibility of designing targeted oncolytic vectors. This targeting of the oncolytic virus at the point of infection provides selectivity of the adenovirus vector on multiple levels: at the cellular level (e.g., selective replication), at the tissue level (e.g., cancer cell specific in situ distribution), and the organ level (e.g., reducing distribution to other organs). These three layers of selectivity can make the ISOAd more potent and more selective compared to current conditionally replicative adenoviruses, which solely depend on control during replication. In addition, the library screening technology established in this work may have broad applications for further development of targeted gene delivery approaches.

Isolation of CD133-Targeted Adenovirus by Screening with a Fiber-Modified Adenovirus Library CD133 (Prominin-1) is a member of the transmembrane glycoprotein family. CD133 is expressed at the cell surface of multiple somatic stem cells as well as hematopoietic stem cells. It is also widely used as a cell surface marker for the isolation and characterization of cancer stem cells (CSCs). A wide variety of cancer cells expressing CD133 show more aggressive biological behavior, poor prognosis, and high recurrence. We developed CSCs-directed therapeutic strategies by employing CD 133 as a target molecule. We have been developing therapeutic approaches based on the oncolytic adenovirus. Recently, we have established a method for isolating transductionally-targeted adenovirus by high-throughput screening. We applied this method for the development of Infectivity-Selective Oncolytic Adenovirus (ISOAd) targeted to mesothelin (MSLN), which is highly over-expressed in pancreatic cancer (Miura et al., 2013, Mol Ther., 21(1):139-48). In this study, we implemented this method to isolate the CD133-specific adenovirus by using ISOAd system to develop not only CSCs-targeted therapeutic strategies but also a new tool of gene delivery to CD133-expressing cells.

To isolate the CD133-targeting Ad, we established 293 cells overexpressing CD133 (293-CD133), and the Ad library with random 7 amino acids in the AB-loop region was screened by infecting this cell line (293-CD133). Random sequences in the initial library started to converge after first round and further converged to single clone (TYMLSRN, SEQ ID NO:106) after the $4^{th}$ round. (Table 4) Ads with redesigned AB-loop, AdML-TYML targeting CD133, were successfully isolated from the high-throughput screening of the Ad library. In order to determine the specificity of AdML-TYML, we next analyzed the binding ability of AdML-TYML to CD133. The binding of AdML-TYML to 293-CD133 cell was significantly higher than 293 cells. Furthermore, the anti-CD 133 antibody inhibited the binding of AdML-TYML to 293-CD133. These data indicated that we successfully generated a fiber-modified adenovirus, AdML-TYML, that specifically targeted to CD133 expressing cells, and provided an important evidence showing functionality of ISOAd system for identification of the selective targeting moiety binding against the specific cell surface molecule of the target cell.

Taken together, the isolated adenovirus with re-targeted motif showed selective infectivity to CD133-positive cells in vitro. Therefore, CD133-targeted adenovirus may be able to bind and infect other cells, including hematopoietic cells, which are particularly difficult to infect with adenovirus. Moreover, the same approach will be possible to isolate the other CSCs-marker-targeted adenovirus. To summarize, CD133-targeted adenovirus will be a key tool for research not only in CSCs-targeted cancer therapy but also CD133-positive cells such as hematopoietic cells.

Systemic Treatment with Fiber-Redesigned Oncolytic Adenovirus Eliminates Tumors In Vivo Systemic treatment of oncolytic virus is one of the potent therapeutics against cancers. However, despite extensive efforts, systemic therapies have provided only limited efficacy for patients with malignant tumors to date. Adenovirus (Ad) has been used as a platform of oncolytic viral agents. Unlike loco-regional therapy, systemic application of cancer gene therapy mandates different level of selectivity of gene delivery. Lack of tumor selectivity at the stage of infection has hampered the in vivo efficacy of systemic therapy. The controlled vector distribution and cancer selective transduction would overcome the obstacles for systemic delivery and enable efficient systemic treatment of cancer.

AdML-VTIN was identified as a mesothelin (MSLN) targeted Ad by screening of high-diversity ($10^9$-level) Ad fiber mutant library. This AB-loop-redesigned Ad yielded a potent and selective infectivity to MSLN-positive pancreatic cancer (Panc-1) in vitro. In the examination of in vivo selectivity and anti-tumor effect, the intra-tumor injection of AdML-VTIN ($10^{10}$ vp/tumor) showed significant anti-tumor effect against Panc-1 tumors, and about half of the tumor disappeared. Contrarily, the same virus showed no anti-tumor effect in MiaPaCa-2 (MSLN-negative). Viral DNA quantitation supported the selective viral replication only in Panc-1.

Next, we compared organ distribution after intravenous injection into nude mice with subcutaneous Panc-1 xenograft among AdML-VTIN, AdML-5WT (wild type Ad5 fiber), and AdML-GERS (against PC-3, prostate cancer cell). The liver sequestration of both AB-loop redesigned Ads were more than one order of magnitude lower than that with AdML-5WT at 1 hr and 48 hrs after injection. At day 7, the viral copy number of AdML-VTIN in the tumor was more than 3 orders of magnitude higher that those with AdML-5WT.

Then, the systemic therapeutic effect against Panc-1 tumors was examined with AdML-VTIN, AdML-5WT, and AdML-GERS. In the single injection, tumor volume was significantly decreased in only AdML-VTIN injected group, and four out of ten tumors were eliminated at 15 days after the injection even though viral amount ($10^9$ vp/mouse) was significant lower than that of intra-tumor injection. Tumor growth was slightly suppressed in another AB-loop redesigned Ad group (AdML-GERS) while Ad with wild-type fiber did not show any tumor suppression. Moreover, the frequent administrations (days 47, 61, 68, and 75) of AdML-VTIN were performed in VTIN group following single injection analysis. Tumor suppression was observed in four out of six regrown tumors and all mice survived at day 75 even though the frequent injections of AdML-VTIN started after tumor volume had increased around 500 mm$^3$.

In this study, systemic injection of the AB-loop redesigned oncolytic Ad with VTIN motif that was identified by Ad library screening showed remarkable anti-tumor effect with low viral amount. Furthermore, frequent administrations suppressed tumor regrowth. Therefore, this new oncolytic Ad enabling systemic therapy may embody efficient treatment for cancers which are mostly found with spread or metastatic lesions.

Comparison of Intravenous and Intratumoral Injection on the Therapeutic Effect of ISOAds The therapeutic effect of mesothelin-targeted oncolytic adenovirus (AdML-VTIN) was compared between i.v. and i.t. administration in Panc-1 tumor-bearing nude mice. Low dose ($1 \times 10^9$ vp) AdML-VTIN showed significant anti-tumor effect in vivo, and the difference between i.v. and i.t. injection was insignificant (FIG. 30). At a higher dose ($3 \times 10^9$ vp), the therapeutic effect was stronger via both routes compared to low dose treatment, and tumor shrinkage was observed at earlier time points (FIG. 31). The difference between i.v. and i.t. remained insignificant. Using the same experimental set up as for FIG. 31, mice were sacrificed and viral copy number was measured by qPCR (FIG. 32). At day 1 and day 5, the virus amount was significantly higher after i.t. injection compared to i.v. injection. However, the virus copy number at day 8 was almost equal between i.t. and i.v. injection, meaning the virus replication after i.v. injection catches up with that of i.t. injection without about one week after injection. These data show that the therapeutic effect of intravenously-injected correctly-targeted OAd is equivalently strong as that of intratumoral injection.

The production of neutralizing antibody (nAb) was assessed after i.t. and i.v. injection (FIG. 33). Intratumoral injection did not significantly induced nAb, while i.v. injection induced anti-adenovirus nAb regardless of the single or four times of dosing.

Dose Dependence of the Antitumor Effect of ISOAds Upon Intravenous Injection.

The therapeutic effect of different dose of i.v. administration of AdML-VTIN was compared in Panc-1 tumor-bearing nude mice. As shown in FIG. 30 and FIG. 31, therapeutic effect increases between $1 \times 10^9$ and $3 \times 10^9$ vp. However, no increase in therapeutic effect was observed between $3 \times 10^9$ vp and $9 \times 10^9$ vp (3-times-higher dose) (FIG. 34).

Intratumoral Virus Replication After Intravenous Administration of ISOAds

AdML-VTIN and AdML-5WR ($3 \times 10^9$ vp) were intravenously injected into Panc-1 tumor-bearing nude mice. 5 days after injection, the tumors were harvested, and then stained with anti-adenovirus hexon antibody (FIG. 35). Hexon is one of the late genes of adenovirus, which is expressed only when the virus is replicating. (Berk, A. J. in Virology, Vol. 2, Edn. 5. (eds. D. Knipe & P. Howley) 2357-2394 (Lipponcott Williams & Wilkins, Philadelphia; 2007).) AdML-VTIN showed significant hexon staining (FITC, Green), while hexon staining with AdML-5WT was minimal. These data indicate that the intravenously-injected targeted vector showed selective and significant replication in the tumor to which the virus is targeted.

Long Term Follow Up of Treated Tumors

The i.v. treatment experiment shown in FIG. 29 had 10 tumors treated with AdML-VTIN. Although other groups were terminated due to tumor growth, we could observe the group with AdML-VTIN for an extended period of time. FIG. 36 plots tumor volume of the individual tumors. At day 47, 4 out of 10 tumors had shrunk and were not measurable, and this group did not show any relapse until the end of observation (day 75); 6 tumors showed tumor regrowth. Three additional doses of AdML-VTIN were intravenously administered (day 47: $1 \times 10^9$ vp, day 61: $1 \times 10^{10}$ vp, and day 68: $1 \times 10^{10}$ vp). Among 6 relapsed tumors, 4 tumors responded to the additional treatment and tumor volume at day 75 was smaller than that of day 47. Two tumors showed some growth arrest or temporary moderate shrinkage but eventually showed overgrowth. Applying Response Evaluation Criteria in Solid Tumors (RECIST) criteria, we observed 40% CR (complete response), 40% PR (partial response), and 20% PD (progressive disease). As shown in the right of this figure, the neutralizing antibody was measured, and the titers of neutralizing antibody did not show any correlation to the therapeutic effect.

Contribution of the Targeting Motif to the Therapeutic Effect of Intravenously Administered ISOAd To prove the contribution of the targeting motifs to the therapeutic effect of i.v. injected viruses, viruses with different targeting motifs were compared in Panc-1 tumor-bearing nude mice. AdML-5WT includes a natural fiber targeted to coxsackie-adenovirus receptor (CAR). AdML-VTIN is targeted to mesothelin. AdML-GERS and AdML-VRLL are targeted to androgen receptor negative prostate cancer cell line PC-3 (target molecule is unknown). When intravenous injection of AdML-5WT, AdML-VTIN, and AdML-GERS were compared at the dose of $3 \times 10^9$ vp, AdML-VTIN showed strong anti-tumor effect with greater tumor shrinkage than the other viruses. AdML-GERS showed a weaker effect than AdML-VTIN, while AdML-5MT did not exhibit detectable anti-tumor effect (FIG. 37). When tested in lower doses ($3 \times 10^8$ vp), the difference between AdML-VTIN and AdML-GERS was more evident (FIG. 38). Compared to AdML-VTIN, the anti-tumor effect of two PC-3-targeted ISOAds (AdML-GERS and AdML-VRLL) and AdML-5WT was significantly weaker. Of the two PC-3 targeted IsoAds (AdML-GERS and AdML-VRLL), AdML-GERS showing some binding to Panc-1 cells (FIG. 26) and showed some anti-tumor effect. Importantly, considering organ distribution data in FIG. 27, where AdML-GERS showed strong mitigation of sequestration by liver and other organs, the strong antitumor effect of AdML-VTIN cannot be achieved without strong and specific targeting motif. Also, comparison of these data with the binding data (FIG. 26) indicates that the therapeutic effect observed in FIGS. 37 & 38 directly correlates with the virus binding to the target cells. Therefore, the strong and selective effect of ISOAd was embodied by the selectivity of the bonding motif placed in the AB-loop of the fiber-knob region.

Targeting CD133 Positive Cells

AdML-TYML, targeted to CD133, shows selective binding and replication in CD133-expressing cells. When AdML-TYML was used to infect 293 cells transfected with empty plasmid (EV) and CD133 expression plasmid (293-CD133: clone #12), AdML-TYML showed more than 5 times higher copy number in clone 12 compared to EV transduced cells. and this trend was more evident at day 5 (FIG. 39($a$)). When the cytocidal effect was compared with crystal violet assay, AdML-5WT's effect was stronger in 293 cells, while AdML-TYML's effect was significantly stronger in CD133-expressing 293 (about 2 orders in $ED_{50}$) (FIG. 39($b$)). Similarly, AdML-5WT binds to colorectal cancer cell lines regardless of CD133 expression, while the binding of AdML-TYML is apparently stronger in a CD133-positive CRC cell line (LoVo) compared to a CD133-negative one (LS174T) (FIG. 40). The binding of AdML-TYML to LoVo was reduced by unti-CD133 Ab, but the binding to LS174T was unaffected (FIG. 41). In the context of viral replication, AdML-TYML shows faster replication in CD133 positive LoVo cells compared to slower and lower replication in CD133negative LS174T cells (FIG. 42($a$)). AdML-TYML shows significant cytocidal effect in LoVo cells as little as at 1 vp/cell, but it shows no cytocidal effect even at 10 vp/cell (FIG. 42($b$)). These results indicates that TYML motif-equipped oncolytic adenovirus (AdML-TYML) shows selective and efficient infection and replication in CD133 positive cells in multiple models, and actually kills CD133-positive colorectal cancer cells.

Colony and Sphere Formation Assay for AdML-TYML Treated Colorectal Cancer Cells

Colony formation assays and sphere formation assays have been used to test the stemness of the cancer stem cell population in many cancers (Gou et al. *Pancreas* 34:429-435 (2007); Rao et al. *Acta Pharmacol. Sin.* 34:793-804 (2013)). In colony formation assay (FIG. 43), ISOAd equipped with TYML motif (AdML-TYML) shows dose dependent reduction of colony formation. AdML-VTIN targeted to mesothelin did not reduce colony formation at all, while ISOAd equipped with GERS and VRLL motifs showed some effects at high doses. WT (=AdML-5WT) is the positive control because this cell line expresses CAR. The outcome of sphere formation assay (FIG. 44($a$), FIG. 44($b$)) correlates with the colony formation assay results (FIG. 43). Since CD133 has been known as a major cancer stem cell marker in colorectal cancers (Ricci-Vitiani et al. *Nature* 445:111-115 (2007)), these data likely indicate the cytolytic virus is attacking the CD133-positive cells, effectively reduced the stem(-like) colorectal cancer cells.

In Vivo Tumor Formation Assay for AdML-TYML Treated Colorectal Cancer Cells

In vivo tumor formation assay is one of the most stringent assays for the stemness of the cancer cells (Ricci-Vitiani et al. *Nature* 445:111-115 (2007)). This assay was used to assess the reduction of cancer stem cells by treatment with CD133-targeted oncolytic adenovirus (AdML-TYML) (FIG. 45). While AdML-TYML treatment completely blocked tumor formation of CD133-positive colorectal cancer cell lines (LoVo), the inhibition of tumor formation in CD133-negative colorectal cancer cell lines (LS174T) was insignificant. These data indicate that CD133-targeted oncolytic adenovirus can reduce/eliminate cancer stem cells with tumor-forming capability, and the effect is CD133 dependent.

Antitumor Effect of CD133-Targeted Oncolytic Adenovirus in LoVo Cells

The CD133-Targeted OAd (AdML-TYML) exhibited significant anti-tumor effect in established tumors (FIG. 46). When subcutaneous LoVo tumor was injected with either $1\times10^{10}$ or $3\times10^{10}$ vp of AdML-TYML, the ISOAds showed significant anti-tumor effect (significant against AdML-5WT and PBS), and there was no difference between two doses. The effect of AdML-WT (without targeting) was observed at high doses, but was weaker than low dose AdML-TYML. The viral copy number on day 5 and day 8 assessed in the parallel experiment (FIG. 47) reflects the difference of the in vivo therapeutic effect between the vectors very well. These data indicate that CD133-targeted oncolytic adenovirus embodies therapeutic effect in the established tumors.

While in several instances above the adenovirus library is described in the context of an exemplary embodiment in which the adenovirus library is an AB-loop modified library, the adenovirus libraries described herein can provide diversity at any other location or region, including for example, other locations or regions within the adenovirus fiber. Exemplary other locations within the fiber include, for example, in the HI-, IJ-, EG-, and/or CD-loop regions. Similarly, while in several instances above the targeting motifs are described in the context of an exemplary embodiment as located in an AB-loop region, the adenoviruses described herein can include targeting motifs at any other location or region, including for example, other locations or regions within the adenovirus fiber. Exemplary other locations within the fiber include, for example, in the HI-, IJ-, EG-, and/or CD-loop regions.

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Lines

In this study, a human embryonic kidney cell line (HEK293 cells), pancreatic cancer cell lines (Panc1, AsPC-1, MiaPaCa2), and Chinese hamster ovarian cell lines (CHO) were used. All the cancer cell lines were obtained from American Tissue Culture Collection (ATCC; Rockville, Md.). These cell lines were cultured in Dulbecco's modified Eagle's medium (DMEM) with 10% fetal bovine serum (FBS). 293-CRE cells, which express Cre recombinase stably, are derived from the HEK293 cell line (Palmer et al., 2003, *Mol Ther* 8:846-852). The 293-CRE-69 cells, which express 5/3-fiber and Cre recombinase, were generated by transfection of pDV69 into 293-CRE cells. The 644 cells express chimeric adenovirus fiber protein (adenovirus type 5 tail and shaft, and adenovirus type 3 knob). 644 cells and pDV69 were a generous gift of Dr. G R Nemerrow, The Scripps Research Institute, La Jolla, Calif. (Von Seggern et al. 2000. J Virol. 74(1):354-362). 293-CRE cells were grown in DMEM with 10% FBS and 100 μg/ml hygromycin (Sigma-Aldrich, St. Louis, Mo.). 293-CRE-69 cells were grown in DMEM with 10% FBS, 100 μg/mlhygromycin and Zeocin 600 μg/ml (Sigma-Aldrich, St. Louis, Mo.). 644 cells were grown in DMEM with 10% FBS and 600 μg/ml Zeocin.

Shuttle Plasmids and Recombinant Adenovirus

The fiber-modified adenoviral shuttle plasmids include 76.1-100 map units (m.u.) of the adenoviral genome with a single loxP site at the E3 region deleted (79.4-84.8 m.u.) (FIG. 2(a)). The pBHI(Csp) plasmid has a Csp45I site in the HI-loop of the fiber knob and pBHIΔCAR(Csp) includes four point mutations in the AB-loop of the fiber knob that abolish CAR binding (Miura et al. 2007. Gene Ther. 14(20): 1448-1460. Epub 2007 Aug. 16). The pBHIΔCAR-fs(+) plasmid has the four AB-loop point mutations as well (Miura et al. 2007. Gene Ther. 14(20):1448-1460. Epub 2007 Aug. 16). The pBMLHI and pBHIΔCAR-fs(+) contain two incompatible Csp45I and SpeI restriction sites in the HI-loop to display random peptides. In both plasmids, one nucleotide was inserted between the Csp45I and SpeI recognition sites to shift the reading frame of the fiber knob (Miura et al. 2007. Gene Ther. 14(20):1448-1460. Epub 2007 Aug. 16). The pBHIΔCAR-GFP was constructed by inserting a cytomegalovirus immediate early enhancer/promoter (CMV promoter) and the green fluorescent protein (GFP) gene downstream of the loxP site of pBHIΔCAR(Csp) (Miura et al. 2007. Gene Ther. 14(20):1448-1460. Epub 2007 Aug. 16). The pMLABΔSK contains the deletion of a 1.8 kb NheI-MunI fragment from pBMLHI for the AB-loop mutants-library backbone plasmids.

The pML-VTIN and pML-THLS plasmids have a GTTACTATTAATCGGTCTGCG (SEQ ID NO:11) (VTINRSA, SEQ ID NO:12) sequence and ACT-CATCTTTCTATTTATGCT (SEQ ID NO:13) (THLSIYA, SEQ ID NO:14) in the AB-loop of NheI-MunI fragment, respectively.

The adenoviral cosmid cAd-WT includes the 0-79.4 m.u. region of the adenovirus genome, which includes a wild-type E1 region and a single loxP site at 79.4 m.u. (Miura et al. 2007. Gene Ther. 14(20):1448-1460. Epub 2007 Aug. 16) (FIG. 2(a)). The cAd-WT was recombined with pBHIΔCAR (Csp), AdΔCAR-WT, or pML-VTIN to generate replication-competent adenovirus vectors with the VTINRSA sequence (AdMLWT-VTIN) and pML-THLS to generate replication-competent adenovirus vectors with the THLSIYA sequence (AdMLWT-THLS) The full-length recombinant adenovirus DNA was generated with the adenovirus cosmid and shuttle plasmid by Cre-mediated recombination in vitro. A shuttle plasmid was linearized by PacI and recombined with equal moles of an adenoviral cosmid by Cre recombinase in vitro to produce a full-length adenoviral DNA. For example, 5 μg of shuttle plasmid and 15 μg of adenoviral cosmid were mixed with 40 U of Cre (2 U per 1 mg of DNA) in 600 μl of reaction mixture at 37° C. for three hours. Then, to generate recombinant adenovirus vectors, 5 μg of recombinant adenoviral DNA was transfected by activated-dendrimer transfection reagent (Superfect Transfect Reagent; Qiagen, Valencia, Calif.) into $2\times10^6$ adenovirus-producing cells in 6-cm dish. (Miura et al. 2007. Gene Ther. 14(20): 1448-1460. Epub 2007 Aug. 16).

Quantitative Analysis for Efficiency of Library Production

For quantification of viral copy number, crude viral lysates (CVLs) were eluted. 2% volumes of CVLs were treated with 1 U of DNaseI at 37° C. for 15 minutes. The DNA from DNaseI-treated CVL were purified with QIAamp Blood kit (Qiagen, Valencia, Calif.) following the manufacture's instruction. Quantification of viral DNA copy numbers was performed by real-time PCR as follows. The total viral copy number was determined with E4 primers by SYBRGreen and the recombinant viral copy number was determined with by Taqman Probe for GFP gene. Oligonucleotide sequence were GFP forward: 5'-TGACCCT-GAAGTTCATCTGC-3' (SEQ ID NO:15); GFP reverse: 5'-GAAGTCGTGCTGCTTCATGT-3' (SEQ ID NO:16); GFP probe: 6FAM-ACCCTCGTGACCACCCTGAC-CTAC-TAMRA (SEQ ID NO:17); E4 forward: 5'-GGAGT-GCGCCGAGACAAC-3' (SEQ ID NO:18); E4 reverse: 5'-ACTACGTCCGGCGTT CCAT-3' (SEQ ID NO:19).

With optimized concentrations of primers and probes, the components of real-time PCR mixture were designed to result in a master mix with a final volume of 25 μl. The control (no template) received 2.5 μl of water. Thermal cycling conditions were as follows: two minutes at 58° C., 10 minutes at 95° C., and 40 cycles of 15 seconds at 95° C. and one minutes at 60° C.

High Throughput Screening of a Fiber-Modified Adenovirus Library Based on Replication Capability on the Target Cells The high throughput procedure of replication-based screening of adenovirus library was described in detail in. Miura et al., Gene Ther. 2007 October; 14(20):1448-60. Briefly, The $1\times10^7$ of Panc1 cells were seeded in 60-mm dishes. One day later, the cells were infected with an adenovirus library at a multiplicity of infection of 1, and two hours later the cells were washed with phosphate-buffered saline. After 5-7 days following the infection, the replicated adenoviruses were scratched from the cells. For each subsequent selection round on Panc1 cells, a 10% volume of the CVL from a preselected adenovirus library was reapplied to the target cells and the process was repeated 3-4 times.

PCR and Sequencing of Fiber-Modified Adenovirus Library

PCR and sequencing of adenovirus library clones were performed on DNA extracted from the CVL of each selection, which served as a template for PCR using primers containing upstream and downstream sequences of the AB-loop: 5'-AAGCTAACTTTGTGGACCAC-3' (SEQ ID NO:20) and 5'-ACTGCCACATTTTGTTAAGA-3' (SEQ ID NO:21), and primers containing upstream and downstream sequences of the HI-loop: 5'-GAAACAGGAGACACAA CTTTCGAA-3' (SEQ ID NO:22) and 5'-ACTAGTC-CAAGTGCATACTCTATG-3' (SEQ ID NO:23). PCR products were cloned by TA cloning using TOPO® TA Cloning® Kits for Sequencing (Invitrogen, Carlsbad, Calif.). A single colony from the transformed bacteria was picked from an agar plate containing ampicillin and examined using colony-PCR with M13 forward primer 5'-GTAAAACGACGGC-CAG-3' (SEQ ID NO:24) and M13 reverse primer 5'-CA-GGAAACAGCTATGAC-3' (SEQ ID NO:25). The PCR products were purified with QIAquick PCR purification kit (Qiagen, Valencia, Calif.) following the manufacture's instruction and the sequencing were run with M13 forward primer.

Binding Assay

The cells were seeded in 6 cm dishes at $1\times10^7$ cells/dish. The next day, the cells were infected with viruses/virus pool at a multiplicity of infection of 100 vp/cell. The dishes were then incubated at 4° C. to allow viruses to bind to the cells while preventing them from entering into the cells. After incubation for two hours, the cells were harvested and washed with PBS two times. DNA was isolated from cells according to a standard protocol using QIAamp Blood mini kit. pPCR assay for E4 genes was performed with SYBR-Green.

Quantitative Analysis of Viral Replication

The cells were seeded in 6-cm dishes at $1\times10^7$ cells/dish. The next day, the cells were infected with viruses/virus pool at a multiplicity of infection of 0.1 vp/cell. After incubation at 37° C. for two hours, cells were washed with PBS and added to 2.5 ml of DMEM medium with 5% FBS. For replication analysis on Day 2 and Day 5, DNA from CVL of the infected cells were isolated using QIAamp Blood mini kit. pPCR assay for E4 genes was performed with SYBR-Green.

Example 2

Cells

A human embryonic kidney cell line (293 cells) and cancer cell lines (Panc-1, AsPC-1, MiaPaCa-2 and A549) were obtained from American Type Culture Collection (ATCC, Manassas, Va.). 293CRE cell line, which stably expresses the CRE recombinase, was an isolated single clone from the 116 cell line (Palmer et al., 2003, *Mol Ther* 8: 846-852). The 293CRE-69 cells expressing both the Ad5/Ad3-fiber and the CRE recombinase were generated by transfecting 293CRE cells with the Ad5/Ad3-fiber expressing plasmid, pDV69. The 644 cells express the Ad5/Ad3 fiber. All cells were maintained in Dulbecco's modified Eagle medium (DMEM) with 4.5 g/L glucose, L-glutamine, and sodium pyruvate (Mediatech, Manassas, Va.) with 10% fetal bovine serum (Hyclone Thermo Scientific, Logan, Utah). All cells were cultured at 37° C. and 5% $CO_2$. The 293CRE cells were grown with 100 μg/ml of hygromycin (Invitrogen, Carlsbad, Calif.). 293CRE-69 cells were grown with hygromycin (100 μg/ml) and Zeocin (600 μg/ml, Invitrogen, Carlsbad, Calif.). 293-MSLN cells over-expressing mesothelin were established by transfection of mesothelin-expressing plasmid, pcDNA3.1-MSLN (mesothelin cDNA cloned into pcDNA3.1), and were grown with G418 (600 μg/ml, Invitrogen, Carlsbad, Calif.).

Rescue Virus and Shuttle Plasmids

The rescue virus (AdMLΔF), generated with the shuttle plasmid pMLΔF, has a wild-type E1 gene, a single loxP site replacing the E3 gene, and a deletion of its fiber region (79.4-91.3 m.u.). This virus was produced and propagated in 644 cells for pseudotyping with the Ad5/Ad3-modified adenovirus fiber. pMLABΔSK, starting plasmids for AB-loop mutants, has the 1.8 kb NheI-MunI fragment of the fiber region (87.6-91.3 m.u.) deleted. The shuttle plasmids of the fiber library (pMLAB-lib) included a 76.1-100 map unit (m.u.) of the adenoviral genome with a single loxP site and library sequences in the AB-loop region of the fiber in place of the E3 region deleted (79.4-84.8 m.u.). The reporter shuttle, pBΔCAR-GFP, was constructed by inserting a CMV-promoter-driven green fluorescent protein (GFP) expression cassette at the downstream of a loxP site in the E3 region, and the AB-loop of the fiber-knob region possesses four point-mutations for ablating CAR-binding.

Shuttle Plasmid for AB-Loop Library

The AB-loop random library was generated via three steps of PCR. The library sequence was generated as a synthetic oligonucleotide, 5'-AAGCTAACTTTGTGGACCACAC-CAGCTC CATCTCCTAAC(NNK)₇GATGCTAAACT-CACTTTGGTCTTAACAAAATGTGGCAGT-3' (N=A,T,G or C, K=G or T; SEQ ID NO:1). This fragment was amplified and ligated with the PCR-amplified adenovirus DNA fragments (upper-PCR: nt31508-32256, and lower-PCR: nt32324-32830). The resultant fragment was then amplified with the primers AB-upper-S (5'-AATTGCTAGC-CCTGCAAACATCAG-3'; SEQ ID NO:7) and AB-lower-AS (5'-AATTCAATTGAAAAATAAACACGTTGAA-3'; SEQ ID NO:10), and then cloned into pMLABΔSK.

Quantitative Analysis for the Adenoviral Copy Number Determination

Crude viral lysates (CVLs) were analyzed as described in Example 1.

Screening of a Fiber-Modified Adenovirus Library

Ten dishes of 293-MSLN cells ($1\times10^7$ cells/6 cm dish) were infected with an Ad library at low multiplicity of infection (approximately 1 MOI) for two hours and then washed with PBS. After 5-7 days following the infection, the viral solution was rescued. For each subsequent round of screening, a ten to twenty percent of the viral solution volume from the previous round was re-infected to the target cells, and the screening processes were repeated 2-3 times. The DNA extracted from the viral solution of each round served as a template for a PCR amplification of the AB-loop region with the following primers; AB-loop-S 5'-AAGCTAACTTTGTGGACCAC-3' (SEQ ID NO:20) and AB-loop-AS 5'-ACTGCCACATTTTGTTAAGA-3' (SEQ ID NO:21). The PCR products were cloned with TOPO TA Cloning Kits for Sequencing (Invitrogen, Carlsbad, Calif.).

Binding and Replication Assay

One day after the cells were seeded ($1\times10^7$ cells/6 cm dish), the cells were infected with virus at 100 vp/cell. The dishes for binding assay were incubated at 4° C. for two hours to allow viruses to bind to cells while preventing internalization of the virus into the cells, and DNA was isolated after extensive wash with PBS. For analyzing virus replication, the dishes were incubated at 37° C. for 5 days. DNA isolation and qPCR for E4 genes were performed as described.

Binding Inhibition of Isolated Adenovirus with siRNA/Antibody

The 293-MSLN and Panc-1 cells were transfected with either a mesothelin siRNA oligonucleotide or a nonspecific scrambled siRNA at a final concentration of 100 nmol/L, using Lipofectamine2000 (Invitrogen, Carlsbad, Calif.). Mock transfection controls received only the transfection reagent. After 72 hours of siRNA transfection, the binding assay was performed. For antibody based inhibition, the 293-MSLN cells were treated with the monoclonal anti-mesothelin antibody at a final concentration of 5 μg/ml. After two hours of incubation at 4° C., the binding assay was performed.

Flow-Cytometry

Cultured cells ($2\times10^5$) were dissociated with Dissociation Buffer (Sigma-Aldrich, St Louis, Mo.). Primary antibody (100 μl, mouse anti-mesothelin monoclonal antibody (k1, Invitrogen, Carlsbad, Calif.) diluted 1:100) was added to the cells and incubated for 1 hour at 4° C. The cells were then washed, resuspended in 100 μl of a secondary antibody (FITC conjugated goat anti-mouse IgG diluted 1:100 for Panc1 cells, PE conjugated goat anti-mouse IgG (Jackson Immuno Research, West Grove, Pa.) diluted 1:100 for 293, 293-MSLN, A549, MiaPaCa-2, and AsPC-1 cells), and incubated for another half an hour at 4° C. Finally, cells were washed twice and analyzed on flow-cytometer (BD FACS Canto II: BD Biosciences, Franklin Lakes, N.J.).

In Vivo Experiment

To analyze the anti-tumor effect in an in vivo model, $2\times10^7$ of Panc-1 and MiaPaCa-2 cells were inoculated subcutaneously into the flank of the female nude mice, and 10^10 vp of the selected virus or control virus was intratumorally injected when the diameter reached 5-7 mm. The condition of the mice was monitored daily, and the tumor diameter was measured twice a week. The tumor volume was calculated as width×length/2. The animal experiments were performed in accordance with the institutionally-approved animal experimental protocol. In a separate experiment under same conditions, the mice were sacrificed at Day 5. The tumor specimens were cut in half; the first half was quickly frozen and kept at −80° C. until used, and the second half was fixed with buffered formaldehyde for immunostaining The DNA was purified from frozen tumor tissue by using DNeasy Blood & Tissue Kit (Qiagen, Valencia, Calif.), and the adenoviral DNA copy number of the E4 region was quantified by qPCR starting from 20 ng DNA. The expression of adenoviral hexon protein in the tumor was analyzed by immunostaining. All slides were scanned at ×100, ×200, and ×400 magnification using a Nikon Eclipse TS100 microscope.

In Vivo Distribution of the Systemically Injected Viruses.

The Panc-1 cell line (10^6 cells) were injected subcutaneously into athymic nude mice. When the tumors grew 5-7 mm in diameter, the mice were treated with 10^11 vp/10 μl PBS of either AdML-VTIN (with targeted fiber) or AdML-5WT (with wild type fiber) injected into the tail vein. After 48 hours, major organs and tumors were harvested. DNA was purified using DNeasy Blood & Tissue Kit (Qiagen, Valencia, Calif.), and the adenoviral DNA copy number of the E4 region was quantified by qPCR starting from 20 ng DNA. In addition, tumor DNA was analyzed at Day 7 after virus injection.

Statistical Analysis.

Statistical comparisons between two groups were evaluated by Student's t-test. Continuous variables were compared by Mann-Whitney-U test. All P-values were 2-sided, and a value of P<0.05 was considered to indicate statistically significant.

Example 3

In this study, we implemented isolated a CD133-specific adenovirus by using ISOAd system to develop CSCs-targeted therapeutic strategies and a new tool of gene delivery to CD133-expressing cells.

To isolate CD133-targeting Ad, we established 293 cells overexpressing CD133 (293-CD133) (FIG. 20). Using the high throughput screening and other methods described in Examples 1 and 2 and Miura et al., 2013, Mol Ther., 21(1):139-48, the Ad library with 7 random amino acids in the AB-loop region was screened by infecting this cell line (293-CD133). Random sequences in the initial library started to converge after first round and further converged to single clone (TYMLSRN, SEQ ID NO:106) after the 4th round. (FIG. 15, Table 4)

As shown in Table 4, sequence convergence was observed in CD133-expressing 293 cells. When 293 cells permanently transfected with CD133 expressing and empty vectors were infected with adenoviral library, sequence convergence to YTMLSRN was observed in 3 rounds of replication based high-throughput screening. YTML was not observed in the CD133-negative cells infected with the Ad library.

TABLE 4

|  | 1st Round | 2nd Round |
|---|---|---|
| Empty Vector (EV) | LSGEPLV (SEQ ID NO: 108) | NK*CNKR (SEQ ID NO: 62) |
|  | QDVNR*Q (SEQ ID NO: 109) | FVMFVNP (SEQ ID NO: 63) |
|  | GEEGSGR (SEQ ID NO: 110) | ACAHGDG (SEQ ID NO: 64) |
|  | ASLFVLR (SEQ ID NO: 111) | TTTHQTT (SEQ ID NO: 65) |
|  | AMIATAA (SEQ ID NO: 112) | IQLQGCN (SEQ ID NO: 66) |
| CD133 (Mix) | ACFTCPS (SEQ ID NO: 113) | AMIATAA (SEQ ID NO: 112) |
|  | LNWHCVG (SEQ ID NO: 114) | IRNHMKD (SEQ ID NO: 67) |
|  | LNWHCVG (SEQ ID NO: 114) | IQLQGRN (SEQ ID NO: 68) |
|  | ALSSTLD (SEQ ID NO: 61) | TYMLSRN (SEQ ID NO: 106) |
|  |  | TKLQSGE (SEQ ID NO: 69) |
|  | 3rd Round | 4th Round |
| Empty Vector (EV) | VQAGTQP (SEQ ID NO: 70) | IQLQGCN (SEQ ID NO: 66) |
|  | NDSKTWS (SEQ ID NO: 71) | VTGYLYL (SEQ ID NO: 74) |
|  | PGWYSY (SEQ ID NO: 72) | ASLFVLR (SEQ ID NO: 111) |
|  | GPCPRLK (SEQ ID NO: 73) | ASLFVLR (SEQ ID NO: 111) |
|  | ASLFVLR (SEQ ID NO: 111) | ASLFVLR (SEQ ID NO: 111) |
| CD133 (Mix) | TYMLSRN (SEQ ID NO: 106) | TYMLSRN (SEQ ID NO: 106) |
|  | TYMLSRN (SEQ ID NO: 106) | TYMLSRN (SEQ ID NO: 106) |
|  | TYMLSRN (SEQ ID NO: 106) | TYMLSRN (SEQ ID NO: 106) |

TABLE 4-continued

TYMLSRN (SEQ ID NO: 106) TYMLSRN (SEQ ID NO: 106)

TYMLSRN (SEQ ID NO: 106) TYMLSRN (SEQ ID NO: 106)

Ads with redesigned AB-loop, AdML-TYML targeting CD133, were successfully isolated from the high-throughput screening of the Ad library. In order to determine the specificity of AdML-TYML, we next analyzed the binding ability of AdML-TYML to CD133. (FIG. 16) The binding of AdML-TYML to 293-CD 133 cell was significantly higher than the binding to wild type 293 cells. Furthermore, the anti-CD 133 antibody inhibited the binding of AdML-TYML to 293-CD133. (FIG. 17) These data indicated that we successfully generated a fiber-modified adenovirus, AdML-TYML, that specifically targeted to CD133 expressing cells, and provided an important evidence showing functionality of ISOAd system for identification of the selective targeting moiety binding against the specific cell surface molecule of the target cell.

Colon cancer cell lines expressing CD133 (LoVo, WiDr and HCT116) (FIG. 21) show good transduction with TYML virus, and pre-incubation with anti-CD133 Ab lower the binding by 45-90% (FIG. 18). On the other hand, CD133-negative LS174T (FIG. 21) shows less transduction with TYML virus and the binding was not effected by anti-CD133 Ab (FIG. 18).

293 cells with/without overexpression of CD133 were infected with TYML virus and virus with wild type fiber. TYML virus showed strong cytocidal effect only in CD133 overexpressing 293 cells. On the other hand, the virus with wild type fiber eliminated 293 cells regardless of CD133 expression. (FIG. 19)

The isolated adenovirus with re-targeted motif showed selective infectivity to CD133-positive cells in vitro. Therefore, CD133-targeted adenovirus may be able to bind and infect to other cells including hematopoietic cells which are particularly difficult to infect with adenovirus. Moreover, the same approach will be possible to isolate the other CSCs-marker-targeted adenovirus. To summarize, CD133-targeted adenovirus will be a key tool for research not only in CSCs-targeted cancer therapy but also CD133-positive cells such as hematopoietic cells.

Example 4

AdML-VTINRSA (AdML-VTIN) was identified as mesothelin (MSLN) targeted Ad by screening of high-diversity ($10^9$-level) Ad fiber mutant library, using the methods described in Examples 1 and 2 and Miura et al., 2013, Mol Ther., 21(1):139-48, on MSLN-overexpressing 293-meso cell line. AdML-VRLLFYP and AdML-GERS-GRW (AdML-GERS) were identified in the same way by the screening with PC-3 anti-androgen therapy-resistant cell line (FIG. 23). The 4th round crude viral lysate (CVL) was collected 5 days after re-infection and either 10 µl (Table 5, column 5th-#1) or 100 µl (Table 5, column 5th-#2) of 2 ml CVL was used to reinfect PC-3 cells for a 5th round of selection. As shown in Table 5, the targeting sequences show convergence to mainly three sequences GERSGRW (SEQ ID NO:105), VRLLFYP (SEQ ID NO:106), and VTINRSA (SEQ ID NO:12).

We have performed library screening directly in an in vivo model. PC-3 cells ($2 \times 10^7$) were inoculated subcutaneously into the flank of the female nude mice, and $10^9$ vp of the adenovirus library was intravenously injected when the tumor diameter reached 5-7 mm. The mice were sacrificed at day 5 and day 10. The DNA was purified from tumor tissue by using DNeasy Blood & Tissue Kit (QIAGEN). The DNA from each tumor (250 ng) served as a template for a PCR amplification of the AB-loop region with the following primers; AB-loop-S 5'-AAGCTAACTTTGTGGACCAC-3' (SEQ ID NO:20) and AB-loop-AS 5'-ACTGCCACATTTT-GTTAAGA-3' (SEQ ID NO:21). The PCR products were cloned with TOPO TA cloning Kits for Sequencing (Invitrogen) and Sanger sequencing were performed for each clone. The library injected intravenously for in vivo screening with PC-3 xenografts in nude mice converged to one of the sequences observed in in vitro screening, VRLLFYP (SEQ ID NO:107). (FIG. 24, Table 6.) Although this sequence was observed during in vitro screening, in vitro screening resulted in convergence to a different sequence (GERSGR (SEQ ID NO:105)) than in vivo screening.

Referring to Tables 4, 5 and 6, VTINRSA (SEQ ID NO:12) is a mesothelin (MSLN) targeted Ad AB-loop variant sequence; VRLLFYP (SEQ ID NO:107) and GERS-GRW (SEQ ID NO:105) are PC3-targeted Ad AB-loop variant sequences; CRLNAEK (SEQ ID NO:96) is a wild-type Ad5 AB-loop variant sequence; CSLNGGG (SEQ ID NO:41) is a variant form of CRLNAEK (SEQ ID NO:96); and TYMLSRN (SEQ ID NO:106) is a CD133-candidate targeted Ad AB-loop variant sequence.

TABLE 5

| | | | Selection Round | | |
|---|---|---|---|---|---|
| Initial Library | 2nd | 3rd | 4th | 5th-#1 | 5th-#2 |
| AAWV (SEQ ID NO: 26) | AGGGGGK (SEQ ID NO: 75) | AKRRAWE (SEQ ID NO: 83) | THLSIYA (SEQ ID NO: 14) | AMIATAA (SEQ ID NO: 112) | ENPKTRV (SEQ ID NO: 91) |
| AMYSTLY (SEQ ID NO: 27) | GHR*VVR (SEQ ID NO: 76) | AKRRAWE (SEQ ID NO: 83) | VLIGDGG (SEQ ID NO: 87) | AVSCIIT (SEQ ID NO: 89) | FRLLFYP (SEQ ID NO: 92) |
| DARVD*D (SEQ ID NO: 28) | GVLDG (SEQ ID NO: 77) | GFVFLVG (SEQ ID NO: 84) | VLTGEGG (SEQ ID NO: 88) | GERSGRW (SEQ ID NO: 105) | GERSGRW (SEQ ID NO: 105) |

TABLE 5-continued

| Initial Library | Selection Round | | | | |
|---|---|---|---|---|---|
| | 2nd | 3rd | 4th | 5th-#1 | 5th-#2 |
| FLAFCFA (SEQ ID NO: 29) | NKHTTMS (SEQ ID NO: 78) | GGVDEE (SEQ ID NO: 85) | VRLLFYP (SEQ ID NO: 107) | GERSGRW (SEQ ID NO: 105) | GERSGRW (SEQ ID NO: 105) |
| IHSALRA (SEQ ID NO: 30) | S*GHHPT (SEQ ID NO: 79) | GGVDEE (SEQ ID NO: 85) | VRLLFYP (SEQ ID NO: 107) | GERSGRW (SEQ ID NO: 105) | GERSGRW (SEQ ID NO: 105) |
| IRVWK*I (SEQ ID NO: 31) | SPLVLYL (SEQ ID NO: 80) | SLTAHLA (SEQ ID NO: 86) | VRLLFYP (SEQ ID NO: 107) | GERSGRW (SEQ ID NO: 105) | IMPMPTT (SEQ ID NO: 93) |
| IYYTIST (SEQ ID NO: 32) | VKKSNDA (SEQ ID NO: 81) | VRLLFYP (SEQ ID NO: 107) | VRLLFYP (SEQ ID NO: 107) | GERSGRW (SEQ ID NO: 105) | VRLLFYP (SEQ ID NO: 107) |
| NRRTILM (SEQ ID NO: 33) | WSVIGRY (SEQ ID NO: 82) | VRLLFYP (SEQ ID NO: 107) | VRLLFYP (SEQ ID NO: 107) | VRLLFYA (SEQ ID NO: 90) | VRLLFYP (SEQ ID NO: 107) |
| PGAGWRP (SEQ ID NO: 34) | WSVIGRY (SEQ ID NO: 82) | VTINRSA (SEQ ID NO: 12) | VRLLFYP (SEQ ID NO: 107) | VRLLFYP (SEQ ID NO: 107) | VRLLFYP (SEQ ID NO: 107) |
| RNNDDTL (SEQ ID NO: 35) | | VTINRSA (SEQ ID NO: 12) | VTINRSA (SEQ ID NO: 12) | VTINRSA (SEQ ID NO: 12) | VSINRSA (SEQ ID NO: 94) |
| RVSRNRL (SEQ ID NO: 36) | | | | VTINRSA (SEQ ID NO: 12) | VTINRSA (SEQ ID NO: 12) |
| SERGDWA (SEQ ID NO: 37) | | | | VTINRSA (SEQ ID NO: 12) | VTINRSA (SEQ ID NO: 12) |
| VEVGGGW (SEQ ID NO: 38) | | | | VTINRSA (SEQ ID NO: 12) | VTINRSA (SEQ ID NO: 12) |
| WGAVFGG (SEQ ID NO: 39) | | | | VTINRSA (SEQ ID NO: 12) | VTINRSA (SEQ ID NO: 12) |
| WHHCPYS (SEQ ID NO: 40) | | | | VTINRSA (SEQ ID NO: 12) | VTINRSA (SEQ ID NO: 12) |
| | | | | VTINRSA (SEQ ID NO: 12) | VTINRSA (SEQ ID NO: 12) |

TABLE 6

| 5 days after i.v. | | | 10 days after i.v. | |
|---|---|---|---|---|
| Run #1 | Run #2 | Run #3 | Run #1 | Run #2 |
| AWGGVVR (SEQ ID NO: 95) | CRLNAEK (SEQ ID NO: 96) | CSLNGGG (SEQ ID NO: 41) | FQRGNCD (SEQ ID NO: 97) | FHRGNCD (SEQ ID NO: 102) |
| CSLNGGG (SEQ ID NO: 41) | CSLNGGG (SEQ ID NO: 41) | VRLLFYP (SEQ ID NO: 107) | VRLLFYP (SEQ ID NO: 107) | FHRGNCD (SEQ ID NO: 102) |
| VRLLFYP (SEQ ID NO: 107) | FQRGNCD (SEQ ID NO: 97) | VRLLFYP (SEQ ID NO: 107) | VRLLFYP (SEQ ID NO: 107) | FQRGNCD (SEQ ID NO: 97) |
| VTINRSA (SEQ ID NO: 12) | MKQ*PVV (SEQ ID NO: 98) | VTINRSA (SEQ ID NO: 12) | VRLLFYP (SEQ ID NO: 107) | THLSIYA (SEQ ID NO: 14) |
| VTINRSA (SEQ ID NO: 12) | VRLLFYP (SEQ ID NO: 107) | VTINRSA (SEQ ID NO: 12) | VRLLFYP (SEQ ID NO: 107) | VKLLFYP (SEQ ID NO: 103) |
| VTINRSA (SEQ ID NO: 12) | VRLLLYP (SEQ ID NO: 99) | VTINRSA (SEQ ID NO: 12) | VRLLFYP (SEQ ID NO: 107) | VRLLFYP (SEQ ID NO: 107) |
| VTINRSA (SEQ ID NO: 12) | VTINRSA (SEQ ID NO: 12) | VTINRSA (SEQ ID NO: 12) | VRLLFYP (SEQ ID NO: 107) | VRLLFSP (SEQ ID NO: 104) |
| | VTINRSA (SEQ ID NO: 12) | VTINRSA (SEQ ID NO: 12) | VRLLFYP (SEQ ID NO: 107) | VRLLFYP (SEQ ID NO: 107) |
| | VTINRSA (SEQ ID NO: 12) | VTINRSA (SEQ ID NO: 12) | VRLLFYP (SEQ ID NO: 107) | VRLLFYP (SEQ ID NO: 107) |

TABLE 6-continued

| 5 days after i.v. | | | 10 days after i.v. | |
|---|---|---|---|---|
| Run #1 | Run #2 | Run #3 | Run #1 | Run #2 |
| | VTINRSA (SEQ ID NO: 12) | YLPQPPS (SEQ ID NO: 100) | VRLLFYP (SEQ ID NO: 107) | VRLLFYP (SEQ ID NO: 107) |
| | | | VRLLFYP (SEQ ID NO: 107) | VRLLFYP (SEQ ID NO: 107) |
| | | | VRLLFYP (SEQ ID NO: 107) | VRLLFYP (SEQ ID NO: 107) |
| | | | VRLLFYP (SEQ ID NO: 107) | VRLLFYP (SEQ ID NO: 107) |
| | | | VRLLFYP (SEQ ID NO: 107) | VRLLFYP (SEQ ID NO: 107) |
| | | | VRLLSYP (SEQ ID NO: 101) | VRLLFYP (SEQ ID NO: 107) |
| | | | VTINRSA (SEQ ID NO: 12) | VRLLFYP (SEQ ID NO: 107) |

AdML-VTIN is an AB-loop-redesigned Ad that yields a potent and selective infectivity to MSLN-positive pancreatic cancer (Panc-1) in vitro. (FIG. 26) In the examination of in vivo selectivity and anti-tumor effect, the intra-tumor injection of AdML-VTIN ($10^{10}$ vp/tumor) showed significant anti-tumor effect against Panc-1 tumors, and about half of the tumor disappeared. (FIG. 29) Contrarily, the same virus showed no anti-tumor effect in MiaPaCa-2 (MSLN-negative). Viral DNA quantitation supported the selective viral replication only in Panc-1.

Next, we compared organ distribution after intravenous injection into nude mice with subcutaneous Panc-1 xenograft among AdML-VTIN, AdML-5WT (wild type Ad5 fiber), and AdML-GERS (against PC-3, prostate cancer cell). The liver sequestration of both AB-loop redesigned Ads were more than one order of magnitude lower than that with AdML-5WT at 1 hr and 48 hrs after injection. At day 7, the viral copy number of AdML-VTIN in the tumor was more than 3 orders of magnitude higher that those with AdML-5WT.

Then, systemic therapeutic effect against Panc-1 tumors was examined with AdML-VTIN, AdML-5WT, and AdML-GERS. (FIG. 29) In the single injection, tumor volume was significantly decreased in only AdML-VTIN injected group, and four out of ten tumors were eliminated at 15 days after the injection even though viral amount ($10^9$ vp/mouse) was significant lower than that of intra-tumor injection. Tumor growth was slightly suppressed in another AB-loop redesigned Ad group (AdML-GERS) while Ad with wild-type fiber didn't show any tumor suppression. Moreover, the frequent administration (days 47, 61, 68, and 75) of AdML-VTIN was performed in VTIN group following single injection analysis. Tumor suppression was observed in four out of six regrown tumors and all mice survived at day 75 even though the frequent injections of AdML-VTIN started after tumor volume had increased around 500 mm³.

In this study, systemic injection of the AB-loop redesigned oncolytic Ad with VTIN motif that was identified by Ad library screening showed remarkable anti-tumor effect with low viral amount. Furthermore, frequent administrations enabled to suppress regrown tumor. Therefore, this new oncolytic Ad enabling systemic therapy may embody efficient treatment for cancers which are mostly found with spread or metastatic lesions.

Example 5

AdML-VTINRSA (AdML-VTIN), AdML-VRLLFYP, and AdML-GERSGRW (AdML-GERS) were identified as mesothelin (MSLN) targeted Ad by screening of high-diversity ($10^9$-level) Ad fiber mutant library, using the methods described in Examples 1 and 2 and Miura et al., 2013, Mol Ther., 21(1):139-48. (FIG. 23) AdML-GERS is an AB-loop-redesigned Ad that shows enhanced cytocidal effect in PC-3 prostate cancer cell. (FIG. 25) GERS virus showed high binding on PC-3 cells compared to other cells, and its binding is stronger than wild type fiber virus or mesothelin-targeted VTIN virus. (FIG. 26) In the mesothelin-positive pancreatic cancer cell line (Panc-1) and natural Ad receptor (coxsackie adenovirs receptoe, CAR)-abundant cell line (293), VTIN and wild type fiber virus showed better binding. None of the viruses showed high binding to mesothelin-negative or CAR-negative pancreatic cancer cell line (MiaPaca-2).

In order to assess systemic persistence, GERS virus was injected to tumor-bearing mice intravenously. (FIG. 27) Vector distribution was measured at 1 hour after injection. GERS and VTIN viruses showed more than 1 order reduction of liver sequestration, and GERS virus showed significant reduction of lung sequestration after systemic injection. GERS showed best intratumoral delivery, which is supposed to be due to lower systemic trap by liver and lung. In this sense, GERS virus possesses beneficial profile for systemic therapy.

The antitumor effect of GERS virus was comparably assessed in PC-3 subcutaneous xenografts. (FIG. 28) GERS virus showed significant effect compared to PBS group and the group injected with the virus with wild type fiber. (Ad with wild type is known to be usable intratumorally, but not feasible to use in clinic because of non-discretionary replication in the human body.) GERS virus showed antitumor effect after intratumoral injection. GERS virus was injected i.v. as a control in pancreatic cancer experiments and showed decent antitumor effect even in a pancreatic cancer model. (FIG. 29)

Example 6

Treatment Effect of AdML-VTIN for Panc-1 Xenograft (Medium Dose) (FIG. 31)

To analyze the antitumor effect in an in vivo model, $2\times10^7$ of Panc1 cells were inoculated subcutaneously into the flank of the female nude mice. When the diameter of tumor reached 5-7 mm, $3\times10^9$ vp of the selected virus (AdML-VTIN) was injected intratumorally (i.t.) or intravenously (i.v.). The tumor diameter was measured twice a week. The tumor volume was calculated as width$^2\times$length/2.

Viral Neutralizing Antibody in AdML-VTIN Injected Nude Mice (FIG. 33)

Neutralizing antibodies against AdML-VTIN were measured in Panc1 cells in 96-well plates by a reduction in virus-induced cell killing. Serum samples were incubated at 56° C. for 30 min to inactivate complement. Serum samples (in six replicate wells) were diluted twofold across a 96-well plate in DMEM with 5% fetal bovine serum. One row contained no serum sample to observe the effect of virus only. AdML-VT1N (10 vp/cells) and serial dilutions of test serum were incubated at 37° C. for 1 hour. After incubation, the serum-virus mixtures (100 µl total volume) were transferred to the 96-well plate containing Panc1 cells ($2\times10^4$/well) and incubated. At 7 days post-infection, the wells were individually scored (+/−) for cytopathic effect. Neutralizing titers were determined by the highest dilution of serum that resulted in at least 50% inhibition of cytopathic effect (≥3 of 6 wells positive for cytopathic effect). (Dhar et al. *Mol. Ther.* 17:1724-1732 (2009).)

Example 7

Colony Formation Assay (FIG. 43)

LoVo cells ($1\times10^5$ cells) were plated in 6-well plates then infected with AdML-TYML or control virus at 0.1 to 100 vp/cells in 1 ml of DMEM with 5% fetal bovine serum, and incubated 37° C. for 2 hours. After incubation, the cells were washed and the medium was replaced with fresh growth medium. Two days after the infection, the cells were trypsinized and counted. Five hundred treated cells were plated per 10-cm culture dish. Ten days later, cells were fixed in 4% PFA and stained with 0.5% crystal violet and colonies were manually counted. (Gou et al. *Pancreas* 34:429-435 (2007).)

Sphere Formation Assay (Stemness) (FIG. 44)

LoVo cells ($1\times10^5$ cells) was plated in 6-well plates then infected with AdML-TYML or control virus at 10 and 100 vp/cells in 1 ml of DMEM with 5% fetal bovine serum, and incubated 37° C. for 2 hours. After incubation, the cells were washed and the medium was replaced with fresh growth medium. Two days after the infection, the cells were trypsinized and counted. For the soft-agar colony formation assay, $5\times10^4$ infected LoVo cells were plated per 6-cm culture dish as a suspension in 3 ml of DMEM containing 10% fetal bovine serum and 0.4% agar on a layer of 5 ml of the same medium containing 0.7% agar. Plates were incubated at 37° C. for 3-4 weeks until colonies were formed. Colonies were stained with 3-(4,5-dimethylthiazol-2-yl)-2,5-diphenyltetrazolium bromide, and photographs of the stained colonies were taken. Total number of spheroid colonies were counted under a light microscope. (Rao et al. *Acta Pharmacol Sin.* 34:793-804 (2013).)

Summary of Tumor Formation Derived From Virus Treated Colon Cancer Cells (FIG. 45)

For studies comparing the tumor-initiating capacity of virus-treated CD 133$^+$ cells versus non-treated CD133$^+$ cells, LoVo and LS174T cells were infected with AdML-TYML at 10 vp/cell. After two hours incubation, the cells were trypsinized and cells ($1\times10^5$ or $1\times10^4$) were inoculated subcutaneously into the flank of the female nude mice. The mice were maintained under standard conditions according to the institutionally approved animal experimental protocol. Tumor appearance was inspected weekly by visual observation and palpation. Animal experiments were terminated one month after cell injection. (Ricci-Vitiani et al. *Nature* 445:111-115 (2007).)

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

What is claimed is:

1. An adenovirus comprising an AB-loop comprising a targeting motif, wherein the targeting motif:
   selectively binds to a tumor cell; and
   comprises the amino acid sequence GERSGRW (SEQ ID NO:105).

2. An adenovirus comprising an AB-loop comprising a targeting motif, wherein the targeting motif:
   selectively binds to a tumor cell that expresses CD133; and
   comprises the amino acid sequence TYMLSRN (SEQ ID NO:106).

3. An adenovirus comprising an AB-loop comprising a targeting motif, wherein the targeting motif:
   selectively binds to a tumor cell; and
   comprises the amino acid sequence VRLLFYP (SEQ ID NO:107).

* * * * *